US010050304B2

(12) United States Patent
Onozuka et al.

(10) Patent No.: US 10,050,304 B2
(45) Date of Patent: Aug. 14, 2018

(54) ADDITIVE FOR NONAQUEOUS ELECTROLYTE, NONAQUEOUS ELECTROLYTE, AND ELECTRICITY STORAGE DEVICE

(75) Inventors: Tomohiro Onozuka, Hyogo (JP); Shohei Fujimoto, Hyogo (JP); Koji Fujita, Hyogo (JP)

(73) Assignee: Sumitomo Seika & Chemicals Co., Ltd., Hyogo (JP)

( * ) Notice: Subject to any disclaimer, the term of this patent is extended or adjusted under 35 U.S.C. 154(b) by 611 days.

(21) Appl. No.: 14/131,132

(22) PCT Filed: Jul. 6, 2012

(86) PCT No.: PCT/JP2012/067324
§ 371 (c)(1),
(2), (4) Date: Feb. 26, 2014

(87) PCT Pub. No.: WO2013/005828
PCT Pub. Date: Jan. 10, 2013

(65) Prior Publication Data
US 2014/0199601 A1      Jul. 17, 2014

(30) Foreign Application Priority Data

Jul. 7, 2011   (JP) ................................ 2011-150945
Jan. 27, 2012  (JP) ................................ 2012-014829
(Continued)

(51) Int. Cl.
*H01M 10/0567*   (2010.01)
*H01G 11/64*     (2013.01)
(Continued)

(52) U.S. Cl.
CPC ....... *H01M 10/0567* (2013.01); *C07C 309/65* (2013.01); *C07C 311/03* (2013.01);
(Continued)

(58) Field of Classification Search
None
See application file for complete search history.

(56) References Cited

U.S. PATENT DOCUMENTS

| 2004/0043300 A1* | 3/2004 | Utsugi .............. H01M 10/0567 429/329 |
| 2227/0154815 | 7/2007 | Kawasaki et al. |

FOREIGN PATENT DOCUMENTS

| JP | 63-102173 | 5/1988 |
| JP | 04-087156 | 3/1992 |

(Continued)

OTHER PUBLICATIONS

Yagupolskii, et al., "Aryl esters of tris(fluorosulphonyl) methane aci form" Tetrahedron Letters, vol. 24, No. 1, 1983, pp. 87-90.
(Continued)

*Primary Examiner* — Jonathan Crepeau
(74) *Attorney, Agent, or Firm* — Hamre, Schumann, Mueller & Larson, P.C.

(57) ABSTRACT

The present invention aims to provide an additive for a non-aqueous electrolyte solution with excellent storage stability capable of forming a stable SEI on the surface of an electrode to improve cell performance such as a cycle performance, a discharge/charge capacity, and internal resistance, when the additive is used for electrical storage devices such as non-aqueous electrolyte solution secondary cells and electric double layer capacitors. The present invention also aims to provide a non-aqueous electrolyte solution containing the additive for a non-aqueous electrolyte solution and to provide an electrical storage device using the non-aqueous electrolyte solution. The present invention is an additive for a non-aqueous electrolyte solution, comprising a compound that has a structure represented by the formula (1-1) or (1-2):

(Continued)

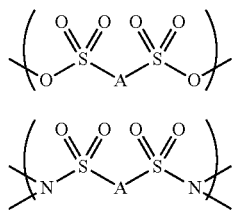

in which A represents $C_mH_{(2m-n)}Z_n$, m being an integer of 1 to 6, n being an integer of 0 to 12, and Z representing a substituted or unsubstituted alkyl group, a silyl group, a phosphonic acid ester group, an acyl group, a cyano group, or a nitro group, the compound having a lowest unoccupied molecular orbital energy of −3.0 to 0.4 eV, a standard enthalpy of formation of −220 to −40 kcal/mol, and an enthalpy change with hydrolysis reaction of −5 to 5 kcal/mol.

12 Claims, 1 Drawing Sheet

(30) Foreign Application Priority Data

| Mar. 9, 2012 | (JP) | 2012-052834 |
|---|---|---|
| Mar. 28, 2012 | (JP) | 2012-074513 |
| Mar. 28, 2012 | (JP) | 2012-074514 |
| Mar. 28, 2012 | (JP) | 2012-074515 |
| Mar. 28, 2012 | (JP) | 2012-074516 |
| Jul. 5, 2012 | (JP) | 2012-151425 |
| Jul. 5, 2012 | (JP) | 2012-151426 |
| Jul. 5, 2012 | (JP) | 2012-151427 |
| Jul. 5, 2012 | (JP) | 2012-151428 |
| Jul. 5, 2012 | (JP) | 2012-151429 |

(51) Int. Cl.

| C07F 9/6544 | (2006.01) |
|---|---|
| C07F 9/655 | (2006.01) |
| C07C 309/65 | (2006.01) |
| C07C 311/03 | (2006.01) |
| C07C 311/08 | (2006.01) |
| C07F 7/21 | (2006.01) |
| C07F 9/40 | (2006.01) |
| H01G 11/58 | (2013.01) |
| C07C 311/13 | (2006.01) |
| C07D 285/36 | (2006.01) |
| C07D 295/26 | (2006.01) |
| C07D 327/04 | (2006.01) |
| C07D 285/01 | (2006.01) |

(52) U.S. Cl.
CPC .......... *C07C 311/08* (2013.01); *C07C 311/13* (2013.01); *C07D 285/01* (2013.01); *C07D 285/36* (2013.01); *C07D 295/26* (2013.01); *C07D 327/04* (2013.01); *C07F 7/21* (2013.01); *C07F 9/4006* (2013.01); *C07F 9/6544* (2013.01); *C07F 9/6552* (2013.01); *H01G 11/58* (2013.01); *H01G 11/64* (2013.01); *Y02E 60/13* (2013.01)

(56) References Cited

FOREIGN PATENT DOCUMENTS

| JP | 05-074486 | 3/1993 |
|---|---|---|
| JP | 05-258753 | 10/1993 |
| JP | 08-045545 | 2/1996 |
| JP | 10-050342 | 2/1998 |
| JP | 11339850 | 12/1999 |
| JP | 2000-003724 | 1/2000 |
| JP | 2001-006729 | 1/2001 |
| JP | 2001-052735 | 2/2001 |
| JP | 2004-281325 | 10/2004 |
| JP | 2005-203341 | 7/2005 |
| JP | 2005-203343 | 7/2005 |
| JP | 2005-228631 | 8/2005 |
| JP | 2006-278106 | 10/2006 |
| JP | 2007-328992 | * 12/2007 |
| JP | 2009-038018 | 2/2009 |
| JP | 2009-054287 | 3/2009 |
| JP | 2009-252545 | 10/2009 |
| JP | 2010-219011 | 9/2010 |
| WO | WO 2005/57715 | * 6/2005 |

OTHER PUBLICATIONS

Schroeter, et al., "Ueber die Methionsäure", Berichte der Duetschen Chemischen Gesellschaft, vol. 38, No. 3, Jul. 1905, pp. 3389-3393—See sheet 3 of the EESR for a concise explanation.

Campbell, et al., "Elimination—addition. Part VI. Elimination of sulphonamido-groups", Journal of the Chemical Society, 1964, pp. 5869-5875.

Vincent, et al., "Condensation du méthane disulfochlorure avec quelques diamines 1,2 et 1,3: études des hétérocycles obtenus", Journal of Heterocyclic Chemistry, vol. 14, No. 3, May 1977, pp. 493-495—See sheet 3 of the EESR for a concise explanation.

Backer, "Nitramides de l'acide méthionique", Recueil des Travaux Chimiques des Pays-Bas, vol. 47, No. 11, Sep. 1928, pp. 942-949—See sheet 3 of the EESR for a concise explanation.

Opitz, et al., "Folgereaktionen von Sulfenen aus Sulfonylchloriden und tertiären Aminen, 3. Kristallstrukturanalyse von Bis(trimethylammoniosulfonyl)methanidtetra phenylborat.—n-σ°-Wechselwirkungen (Hyperkonjugation und Homohyperkonjugation) in Sulfen—Amin-S, N-Addukten", Chemische Berichte, vol. 125, No. 7, Jul. 1992, pp. 1621-1626—See sheet 3 of the EESR for a concise explanation.

Kessler, et al., "Synthesis of N-Substituted Methanedisulfonamides and N'-Subsituted Methanedisulfonylureas" Journal of Pharmaceutical Sciences, vol. 50, No. 10, Oct. 1961, pp. 842-844.

Su, et al., "Synthesis of fluorinated phosphonic, sulfonic, and mixed phosphonic/sulfonic acids" Canadian Journal of Chemistry, vol. 67, No. 11, Nov. 1989, pp. 1795-1799.

* cited by examiner

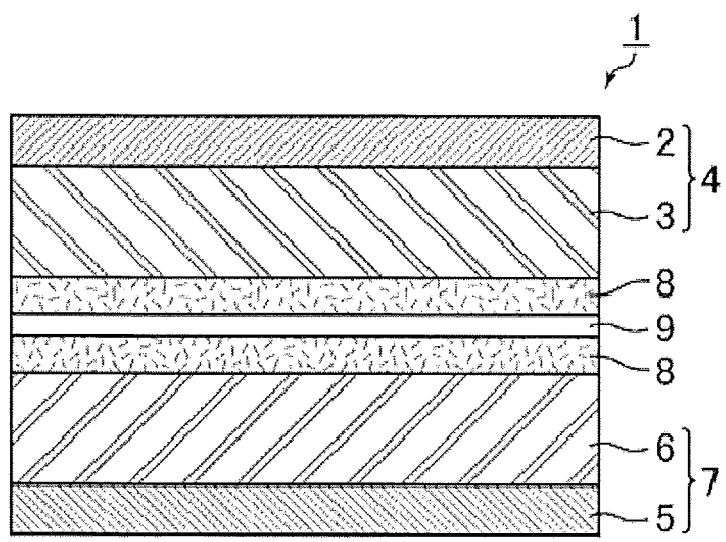

ADDITIVE FOR NONAQUEOUS ELECTROLYTE, NONAQUEOUS ELECTROLYTE, AND ELECTRICITY STORAGE DEVICE

TECHNICAL FIELD

The present invention relates to an additive for a non-aqueous electrolyte solution with excellent storage stability capable of forming a stable solid electrolyte interface on the surface of an electrode to improve cell performance such as a cycle performance, a discharge/charge capacity, and internal resistance, when the additive is used for electrical storage devices such as non-aqueous electrolyte solution secondary cells and electric double layer capacitors. The present invention also relates to a non-aqueous electrolyte solution that contains the additive for a non-aqueous electrolyte solution and relates to an electrical storage device using the non-aqueous electrolyte solution.

BACKGROUND ART

In recent years, electrical storage devices such as non-aqueous electrolyte solution secondary cells and electric double layer capacitors have been widely studied with the increase in demand for solving environmental problems or establishing a sustainable recycling-based society. For example, lithium-ion batteries have high working voltage and energy density, and are therefore used as power sources of laptops, mobile phones, and the like. Such lithium-ion batteries are promising because they have higher energy density than lead batteries and nickel-cadmium batteries to achieve higher capacity.

However, lithium-ion batteries have a problem in that the battery capacity is reduced after repeating a charge/discharge cycle. This is because repeating a charge/discharge cycle over a long period of time causes, for example, decomposition of an electrolyte solution due to electrode reaction, reduction of impregnation of an electrolyte into an electrode active material layer, or reduction of intercalation efficiency of lithium ions.

In order to suppress reduction of a battery capacity due to repeating a charge/discharge cycle, addition of a variety of additives to an electrolyte solution is considered. An additive decomposes during an initial charge/discharge cycle and forms a solid electrolyte interface (SEI) as a film on the surface of an electrode.

Since an SEI is formed during an initial charge/discharge cycle, electricity is not consumed for decomposition of a solvent of an electrolyte solution, and lithium ions can transfer between electrodes through the SEI. That is, formation of an SEI prevents degradation of electrical storage devices such as non-aqueous electrolyte solution secondary cells after repeating a charge/discharge cycle, and contributes to an improvement of cell performance, storage characteristics, load characteristics, and the like.

Patent Literatures 1 to 3 disclose, for example, a cyclic mono-sulfonic acid ester as an additive for an electrolyte solution capable of forming an SEI. Patent Literature 4 discloses a sulfur-containing aromatic compound. Patent Literature 5 discloses a disulfide compound. Further, Patent Literatures 6 to 9 disclose disulfonic acid esters.

Patent Literatures 10 to 13 disclose an electrolyte solution containing vinylene carbonate and vinyl ethylene carbonate. Patent Literatures 14 and 15 disclose an electrolyte solution containing 1,3-propane sultone and butane sultone.

CITATION LIST

Patent Literature

Patent Literature 1: JP-S63-102173 A
Patent Literature 2: JP 2000-003724 A
Patent Literature 3: JP-H11-339850 A
Patent Literature 4: JP-H05-258753 A
Patent Literature 5: JP 2001-052735 A
Patent Literature 6: JP 2009-038018 A
Patent Literature 7: JP 2005-203341 A
Patent Literature 8: JP 2004-281325 A
Patent Literature 9: JP 2005-228631 A
Patent Literature 10: JP-H04-87156 A
Patent Literature 11: JP-H05-74486 A
Patent Literature 12: JP-H08-45545 A
Patent Literature 13: JP 2001-6729 A
Patent Literature 14: JP-S63-102173 A
Patent Literature 15: JP-H10-50342 A

SUMMARY OF INVENTION

Technical Problem

For an indicator of the adaptability of an additive for a non-aqueous electrolyte solution for electrochemical reduction on an electrode of non-aqueous electrolyte solution secondary cells, use of an energy level of the LUMO (lowest unoccupied molecular orbital) energy of a compound composing the additive for a non-aqueous electrolyte solution has been reported, for example, in "Geun-Chang, Hyung-Jin Kim, Seung-ll Yu, Song-Hui Jun, Jong-Wook Choi, Myung-Hwan Kim, Journal of The Electrochemical Society, 147, 12,4391 (2000)". Such a literature states that a compound having a low LUMO energy is an excellent electron acceptor, and is used as an additive for a non-aqueous electrolyte solution capable of forming a stable SEI on the surface of an electrode of non-aqueous electrolyte solution secondary cells or the like. Therefore, measurement of the LUMO energy of a compound allows easy evaluation of whether the compound has a capability to form a stable SEI on the surface of an electrode of electrical storage devices such as non-aqueous electrolyte solution secondary cells. Such measurement is now used as a very useful means.

Meanwhile, the compounds disclosed in Patent Literatures 1 to 9 have problems in that they have a high LUMO energy and are therefore poor in a performance as an additive for a non-aqueous electrolyte solution, or in that they are chemically unstable even when a LUMO energy is low. In particular, a disulfonic acid ester compound shows a low LUMO energy, but is unstable for moisture to be easily degraded. Therefore, in order to store it for a long period of time, the moisture content and the temperature need to be tightly controlled. In addition, for example, since, in general, lithium-ion batteries need to have heat resistance of about 60° C. and lithium ion capacitors need to have heat resistance of about 80° C., one of important subjects is to improve the stability of an additive for a non-aqueous electrolyte solution to be used in an electrical storage device at high temperatures.

Further, the performance of an SEI formed on the surface of an electrode is different depending on an additive to be used and is deeply involved in cell performance such as a cycle performance, a discharge/charge capacity, and internal resistance. However, use of conventional additives causes difficulty in forming an SEI with a sufficient performance and maintaining the cell performance at a high level for a long period of time.

For example, Patent Literatures 10 to 15 disclose electrolyte solutions using vinylene carbonate compounds or sultone compounds such as 1,3-propane sultone as an additive. Such electrolyte solutions form SEI on the surface of an anode by electrochemical reduction decomposition to allow suppression of irreversible reduction of capacity. Such SEI formed from these additives has a great ability to protect an electrode, but has low lithium ion conductivity. Therefore, such SEI has a poor ability to reduce the internal resistance. In addition, such formed SEI does not have enough strength to withstand long term use, and specifically decomposes or cracks during use. As a result, the surface of an anode is exposed, which leads to decomposition of an electrolyte solution solvent to reduce cell performance.

Such conventional additives for a non-aqueous electrolyte solution with insufficient abilities have room for improvement. Therefore, novel additives for a non-aqueous electrolyte solution with excellent storage stability are desired to be developed which is capable of forming a stable SEI on the surface of an electrode to improve cell performance of electrical storage devices such as non-aqueous electrolyte solution secondary cells and electric double layer capacitors.

The present invention aims to provide an additive for a non-aqueous electrolyte solution with excellent storage stability capable of forming a stable SEI on the surface of an electrode to improve cell performance such as a cycle performance, a discharge/charge capacity, and internal resistance, when the additive is used for electrical storage devices such as non-aqueous electrolyte solution secondary cells and electric double layer capacitors. The present invention also aims to provide a non-aqueous electrolyte solution containing the additive for a non-aqueous electrolyte solution and to provide an electrical storage device using the non-aqueous electrolyte solution.

Solution to Problem

One aspect of the present invention is an additive for a non-aqueous electrolyte solution, comprising a compound that has a structure represented by the formula (1-1) or the formula (1-2):

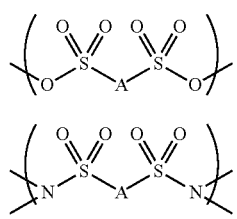

wherein A represents $C_mH_{(2m-n)}Z_n$, m being an integer of 1 to 6, n being an integer of 0 to 12, and Z representing a substituted or unsubstituted alkyl group, a silyl group, a phosphonic acid ester group, an acyl group, a cyano group, or a nitro group, the compound having a lowest unoccupied molecular orbital energy of −3.0 to 0.4 eV, a standard enthalpy of formation of −220 to −40 kcal/mol, and an enthalpy change with hydrolysis reaction of −5 to 5 kcal/mol.

The present invention is described in detail below.

The present inventors found that an additive for a non-aqueous electrolyte solution including a compound (hereinafter, also referred to as a disulfonyl compound according to the present invention) that has a structure represented by the formula (1-1) or (1-2) and has a lowest unoccupied molecular orbital energy of −3.0 to 0.4 eV, a standard enthalpy of formation of −220 to −40 kcal/mol, and an enthalpy change with hydrolysis reaction of −5 to 5 kcal/mol can form a stable SEI on the surface of an electrode to improve cell performance such as a cycle performance, a discharge/charge capacity, and internal resistance when the additive is added to a non-aqueous electrolyte solution and the resulting non-aqueous electrolyte solution is used for an electrical storage device such as a non-aqueous electrolyte solution secondary cell. Thus, the present invention is completed.

The disulfonyl compound according to the present invention has a structure represented by the formula (1-1) or (1-2).

In the formulas (1-1) and (1-2), A represents $C_mH_{(2m-n)}Z_n$ in which m is an integer of 1 to 6, n is an integer of 0 to 12, and Z represents a substituted or unsubstituted alkyl group, a silyl group, a phosphonic acid ester group, an acyl group, a cyano group, or a nitro group. m is preferably up to 4 and more preferably up to 2. A is preferably a methylene group or an ethylene group. In cases where Z is a substituted alkyl group, at least one or all of the hydrogen atoms of the alkyl group are preferably substituted by a fluorine atom.

The disulfonyl compound according to the present invention is preferably a compound represented by the formula (2):

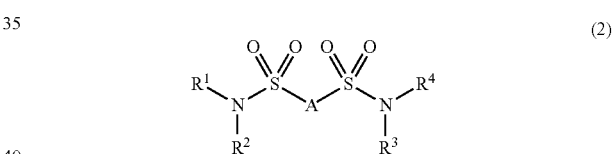

wherein A represents $C_mH_{(2m-n)}Z_n$, m being an integer of 1 to 6, n being an integer of 0 to 12, and Z representing a substituted or unsubstituted alkyl group, a silyl group, a phosphonic acid ester group, an acyl group, a cyano group, or a nitro group; and $R^1$, $R^2$, $R^3$, and $R^4$ each independently represent a hydrogen atom, a substituted or unsubstituted C1-C6 alkyl group, a substituted or unsubstituted phenyl group, or $-R^5X^1$ in which $R^5$ represents a substituted or unsubstituted C1-C6 alkylene group and $X^1$ represents a substituted or unsubstituted phenyl group or a substituted or unsubstituted phenoxy group, $R^2$ and $R^3$ may form a ring together and represent a substituted or unsubstituted C1-C6 alkylene group, a substituted or unsubstituted phenylene group, a carbonyl group, a sulfinyl group, or a C2-C6 divalent group containing alkylene or fluoroalkylene units joined by an ether linkage to each other, and $R^1$ and $R^4$, which form no ring, each represent $-R^6X^2$ in which $R^6$ represents a substituted or unsubstituted C0-C6 alkylene group and $X^2$ represents a hydrogen atom, a halogen atom, a substituted or unsubstituted C1-C6 alkyl group, or a substituted or unsubstituted phenyl group, or a combination of $R^1$ and $R^2$ and a combination of $R^3$ and $R^4$ may form a ring together and represent a C1-C6 alkylene group or a C1-C6 alkylene group optionally having an oxygen atom, a nitrogen atom which may have a substituent, or a sulfur atom, in a carbon chain or at an end of a chain.

The compound represented by the formula (2) is preferably a disulfonic acid amide compound represented by the formula (3):

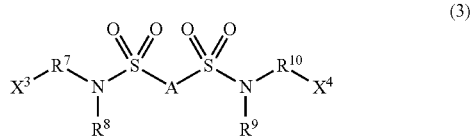

(3)

wherein A represents $C_mH_{(2m-n)}Z_n$, m being an integer of 1 to 6, n being an integer of 0 to 12, Z representing a substituted or unsubstituted C1-C4 alkyl group, a silyl group, an acyl group, a cyano group, or a nitro group; $R^7$ and $R^{19}$ each independently represent a substituted or unsubstituted C0-C6 alkylene group; $X^3$ and $X^4$ each independently represent a substituted or unsubstituted phenyl group; and $R^8$ and $R^9$ each independently represent a hydrogen atom, a substituted or unsubstituted C1-C6 alkyl group, or $—R^{11}X^5$ in which $R^{11}$ represents a substituted or unsubstituted C1-C6 alkylene group and $X^5$ represents a substituted or unsubstituted phenyl group or a phenoxy group.

In the formula (3), $R^7$ and $R^{10}$ each independently represent a substituted or unsubstituted C0-C6 alkylene group. If $R^7$ and/or $R^{10}$ is an alkylene group having seven or more carbon atoms, the compound represented by the formula (3) may become less soluble in a non-aqueous solvent. The number of carbon atoms of the alkylene group represented by $R^7$ or $R^{10}$ is preferably up to 3.

In the formula (3), in cases where $R^7$ is a C0 alkylene group, a nitrogen atom bonded to $R^8$ is directly bonded to $X^3$, and in cases where $R^{10}$ is a C0 alkylene group, a nitrogen atom bonded to $R^9$ is directly bonded to $X^4$.

In the formula (1), in cases where $R^7$ is a C0 alkylene group, a nitrogen atom bonded to $R^8$ is directly bonded to $X^3$, and in cases where $R^{10}$ is a C0 alkylene group, a nitrogen atom bonded to $R^9$ is directly bonded to $X^4$.

In the formula (3), examples of the C1-C6 alkylene group represented by $R^7$ or $R^{10}$ include methylene, ethylene, n-propylene, isopropylene, n-butylene, 1-methylethylene, 1-ethylethylene, n-pentylene, and n-hexylene. In particular, methylene is preferred.

In the formula (3), $X^3$ and $X^4$ each independently represent a substituted or unsubstituted phenyl group. The compound represented by the formula (3) in which $X^3$ and $X^4$ are each a substituted or unsubstituted phenyl group shows a low LUMO energy so that the compound is susceptible to electrochemical reduction.

In the formula (3), examples of the substituted or unsubstituted phenyl group represented by $X^3$ or $X^4$ include phenyl, 2-methylphenyl, 3-methylphenyl, 4-methylphenyl, 2-ethylphenyl, 3-ethylphenyl, 4-ethylphenyl, 2-methoxyphenyl, 3-methoxyphenyl, 4-methoxyphenyl, 2-ethoxyphenyl, 3-ethoxyphenyl, 4-ethoxyphenyl, 2-(dimethylamino)phenyl, 3-(dimethylamino)phenyl, 4-(dimethylamino)phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, and 4-bromophenyl. In particular, preferred are phenyl, 2-fluorophenyl, 3-fluorophenyl, and 4-fluorophenyl because they provide a compound susceptible to electrochemical reduction and showing a low LUMO energy.

In the formula (3), $R^8$ and $R^9$ each independently represent a hydrogen atom, a substituted or unsubstituted C1-C6 alkyl group, or $—R^{11}X^5$ in which $R^{11}$ represents a substituted or unsubstituted C1-C6 alkylene group and $X^5$ represents a substituted or unsubstituted phenyl group or a phenoxy group.

In the formula (3), if the substituted or unsubstituted alkyl group represented by $R^8$ or $R^9$ is an alkyl group having seven or more carbon atoms, the compound represented by the formula (3) may become less soluble in a non-aqueous solvent. The number of carbon atoms of the alkyl group represented by $R^8$ or $R^9$ is preferably up to 3.

In the formula (3), examples of the substituted or unsubstituted C1-C6 alkyl group represented by $R^8$ or $R^9$ include methyl, ethyl, n-propyl, isopropyl, n-butyl, isobutyl, t-butyl, n-pentyl, and n-hexyl. In particular, methyl is preferred. In cases where the alkyl group represented by $R^8$ or $R^9$ is a substituted alkyl group, at least one or all of the hydrogen atoms of the substituted alkyl group are preferably substituted by a halogen atom and more preferably substituted by a fluorine atom.

In the formula (3), in cases where $R^8$ and $R^9$ are each independently $—R^{11}X^5$, $R^{11}$ represents a substituted or unsubstituted C1-C6 alkylene group. If $R^{11}$ is an alkylene group having seven or more carbon atoms, the compound represented by the formula (3) may become less soluble in a non-aqueous solvent. The number of carbon atoms of the alkylene group represented by $R^{11}$ is preferably up to 3.

Examples of the alkylene group represented by $R^{11}$ include methylene, ethylene, n-propylene, isopropylene, n-butylene, 1-methylethylene, 1-ethylethylene, n-pentylene, and n-hexylene. In particular, methylene is preferred.

Further, in the formula (3), $X^5$ of $—R^{11}X^5$ as $R^8$ or $R^9$ represents a substituted or unsubstituted phenyl group or a substituted or unsubstituted phenoxy group. Examples of $X^5$ include phenyl, 2-methylphenyl, 3-methylphenyl, 4-methylphenyl, 2-ethylphenyl, 3-ethylphenyl, 4-ethylphenyl, 2-methoxyphenyl, 3-methoxyphenyl, 4-methoxyphenyl, 2-ethoxyphenyl, 3-ethoxyphenyl, 4-ethoxyphenyl, 2-(dimethylamino)phenyl, 3-(dimethylamino)phenyl, 4-(dimethylamino)phenyl, phenoxy, 2-methylphenoxy, 3-methylphenoxy, 4-methylphenoxy, 2-ethylphenoxy, 3-ethylphenoxy, 4-ethylphenoxy, 2-methoxyphenoxy, 3-methoxyphenoxy, 4-methoxyphenoxy, 2-ethoxyphenoxy, 3-ethoxyphenoxy, 4-ethoxyphenoxy, 2-(dimethylamino)phenoxy, 3-(dimethylamino)phenoxy, and 4-(dimethylamino)phenoxy. In particular, phenyl is preferred.

In the formula (3), A represents $C_mH_{(2m-1)}Z_n$ in which m is an integer of 1 to 6, n is an integer of 0 to 12, and Z represents a substituted or unsubstituted C1-C4 alkyl group, a silyl group, an acyl group, a cyano group, or a nitro group. m is preferably up to 2. In cases where Z is a substituted alkyl group, at least one or all of the hydrogen atoms of the alkyl group are preferably substituted by a fluorine atom.

Examples of the compound represented by the formula (3) include methanedisulfonic acid bis(phenylamide), methanedisulfonic acid bis(methylphenylamide), methanedisulfonic acid bis(ethylphenylamide), methanedisulfonic acid bis(n-propylphenylamide), methanedisulfonic acid bis(n-butylphenylamide), methanedisulfonic acid bis(n-pentylphenylamide), methanedisulfonic acid bis(n-hexylphenylamide), methanedisulfonic acid bis(dibenzylamide), methanedisulfonic acid bis(benzylmethylamide), methanedisulfonic acid bis(benzylethylamide), methanedisulfonic acid bis(benzylpropylamide), methanedisulfonic acid bis(benzyl-n-butylamide), methanedisulfonic acid bis(benzylpentylamide), methanedisulfonic acid bis(benzylhexylamide), methanedisulfonic acid bis(diphenylamide), methanedisulfonic acid bis(benzylphenylamide), methanedisulfonic acid bis(phenethylphenylamide), methanedisulfonic acid bis(phenyl(3-phenylpropyl)amide), methanedisulfonic acid bis(phenyl(4-phenylbutyl)amide), methanedisulfonic acid bis(phenyl(5-phenylpentyl)amide), methanedisulfonic acid bis(phenyl(6-phenylhexyl)amide), methanedisulfonic acid bis(phenyl(3-phenylpropyl)amide), methanedisulfonic acid bis(4-fluorophenylamide), methanedisulfonic acid bis[(4-fluorophenyl)methylamide], methanedisulfonic acid bis[(4-fluorophenyl)ethylamide], methanedisulfonic acid bis[(4-fluorophenyl)propylamide], methanedisulfonic acid bis[(4-fluorophenyl) n-butylamide], methanedisulfonic acid bis[(4-fluorophenyl)pentylamide], methanedisulfonic acid bis[(4-fluorophenyl)hexylamide], methanedisulfonic acid bis[(4-fluorobenzyl)methylamide], methanedisulfonic acid bis[(4-fluorobenzyl)ethylamide], methanedisulfonic acid bis[(4-fluorobenzyl)propylamide], methanedisulfonic acid bis[(4-fluorobenzyl) n-butylamide], methanedisulfonic acid bis[(4-fluorobenzyl)pentylamide], methanedisulfonic acid bis[(4-fluorobenzyl)hexylamide], methanedisulfonic acid bis[(4-fluorophenyl)phenylamide], methanedisulfonic acid bis[(4-fluorobenzyl)phenylamide], methanedisulfonic acid bis[(4-fluorophenethyl)phenylamide], methanedisulfonic acid bis[phenyl(3-(4-fluorophenyl)propylamide)], methanedisulfonic acid bis[phenyl(4-(4-fluorophenyl)butyramide)], methanedisulfonic acid bis[phenyl(5-(4-fluorophenyl)pentylamide)], 1,1-ethanedisulfonic acid bis(methylphenylamide), 1,1-ethanedisulfonic acid bis(benzylmethylamide), 1,2-ethanedisulfonic acid bis(methylphenylamide), 2-oxopropane-1,1-disulfonic acid bis(methylphenylamide), α,α-bis((methylphenylamino)sulfonyl)acetophenone, 2,2-bis((methylphenylamino)sulfonyl)acetonitrile, bis((methylphenylamino)sulfonyl)nitromethane, and trimethyl bis((methylphenylamino)sulfonyl)methylsilane.

In particular, the disulfonic acid amide compound represented by the formula (3) is preferably a disulfonic acid amide compound represented by the formula (4) because it is easily produced and has a low LUMO energy and excellent storage stability.

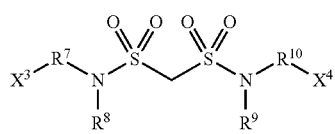

(4)

$R^7$, $R^8$, $R^9$, $R^{10}$, $X^3$, and $X^4$ in the formula (4) are the same as $R^7$, $R^8$, $R^9$, $R^{10}$, $X^3$ and $X^4$ in the formula (3), respectively.

In particular, the disulfonic acid amide compound represented by the formula (4) is more preferably a disulfonic acid amide compound represented by any of the formulas (5) to (8).

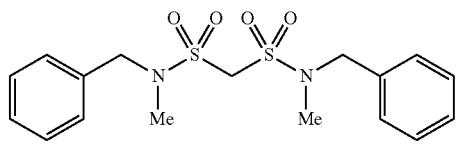

(5)

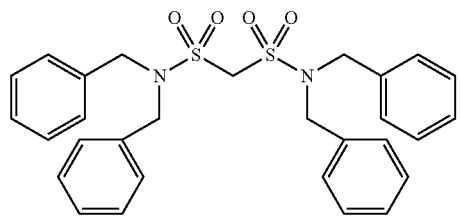

(6)

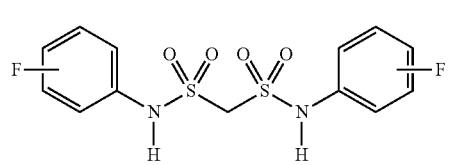

(7)

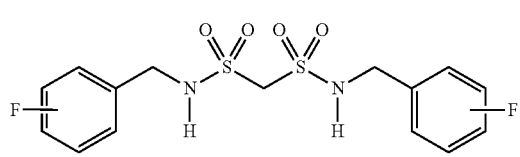

(8)

The disulfonic acid amide compound represented by the formula (3) is produced, for example, by reacting a primary or secondary amine having —$R^7X^3$ and $R^8$ as a substituent and a primary or secondary amine having —$R^{10}X^4$ and $R^9$ as substituents ($R^7$, $R^8$, $R^9$, $R^{10}$, $X^3$, and $X^4$ are the same as those in the formula (3)) with a compound having a group represented by A (A is the same as that in the formula (3)) between two chlorosulfonyl groups.

Specifically, the disulfonic acid amide compound represented by the formula (5) is produced by first adding methanedisulfonyl chloride dropwise to N,N-benzylmethylamine, followed by dropwise addition of triethylamine, then stirring them to complete the reaction, then extracting a target compound into an organic phase, and finally recovering the crystalized compound by filtration. In the production of the compound, a reaction solvent such as 1,2-dimethoxyethane may be optionally used.

Further, the disulfonic acid amide compounds represented by the formulas (6), (7), and (8) are produced by reacting N,N-dibenzylamine, monofluoroaniline, and monofluorobenzylamine with methanedisulfonyl chloride, respectively, by the same method as the disulfonic acid amide compound represented by the formula (5). N,N-dibenzylamine, monofluoroaniline, and monofluorobenzylamine are used instead of the N,N-benzylmethylamine.

The compound represented by the formula (2) is preferably a cyclic disulfonic acid amide compound represented by the formula (9):

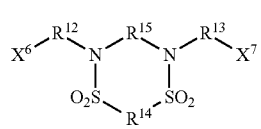

(9)

wherein $R^{12}$ and $R^{13}$ each independently represent a substituted or unsubstituted C0-C6 alkylene group, $R^{14}$ represents a substituted or unsubstituted C1-C5 alkylene group, $R^{15}$ represents a substituted or unsubstituted C1-C5 alkylene group, a substituted or unsubstituted phenylene group, a carbonyl group, a sulfinyl group, or a C2-C6 divalent group containing alkylene or fluoroalkylene units joined by an ether linkage to each other, and $X^6$ and $X^7$ each independently represent a hydrogen atom, a halogen atom, a substituted or unsubstituted C1-C6 alkyl group, or a substituted or unsubstituted phenyl group.

In the formula (9), $R^{12}$ and $R^{13}$ each independently represent a substituted or unsubstituted C0-C6 alkylene group. If $R^{12}$ and/or $R^{13}$ are an alkylene group having seven or more carbon atoms, the compound represented by the formula (9) may become less soluble in a non-aqueous solvent. The number of carbon atoms of the alkylene group represented by $R^{12}$ or $R^{13}$ is preferably up to 3.

In the formula (9), in cases where $R^{12}$ is a C0 alkylene group, a nitrogen atom bonded to $R^{12}$ is directly bonded to $X^6$, and in cases where $R^{13}$ is a C0 alkylene group, a nitrogen atom bonded to $R^{13}$ is directly bonded to $X^7$.

In the formula (9), examples of the C1-C6 alkylene group represented by $R^{12}$ or $R^{13}$ include methylene, ethylene, n-propylene, isopropylene, n-butylene, ethylidene, 1-methylethylene, 1-ethylethylene, n-pentylene, and n-hexylene. In particular, methylene is preferred.

In cases where the alkylene group represented by $R^{12}$ or $R^{13}$ is a substituted alkylene group, the substituted alkylene group preferably has a halogen atom and more preferably has a fluorine atom as a substituent.

In the formula (9), $R^{14}$ represents a substituted or unsubstituted C1-C5 alkylene group. If $R^{14}$ is an alkylene group having six or more carbon atoms, the compound represented by the formula (9) may become less soluble in a non-aqueous solvent. The number of carbon atoms of the alkylene group represented by $R^{14}$ is preferably up to 4.

In the formula (9), examples of the C1-C5 alkylene group represented by $R^{14}$ include methylene, ethylene, n-propylene, isopropylene, n-butylene, ethylidene, 1-methylethylene, 1-ethylethylene, and n-pentylene. In particular, methylene is preferred.

In cases where $R^{14}$ is a substituted alkylene group, the substituted alkylene group preferably has a halogen atom and more preferably has a fluorine atom as a substituent.

In the formula (9), $R^{15}$ represents a substituted or unsubstituted C1-C5 alkylene group, a substituted or unsubstituted phenylene group, a carbonyl group, a sulfinyl group, or a C2-C6 divalent group containing alkylene or fluoroalkylene units joined by an ether linkage to each other.

If $R^{15}$ is an alkylene group having six or more carbon atoms, the compound represented by the formula (9) may become less soluble in a non-aqueous solvent. The number of carbon atoms of the alkylene group represented by $R^{15}$ is preferably up to 4.

In the formula (9), examples of the C1-C5 alkylene group represented by $R^{15}$ include methylene, ethylene, n-propylene, isopropylene, n-butylene, ethylidene, 1-methylethylene, 1-ethylethylene, and n-pentylene. In particular, methylene is preferred.

In cases where $R^{15}$ is a substituted alkylene group, the substituted alkylene group preferably has a halogen atom and more preferably has a fluorine atom as a substituent.

In the formula (9), in cases where $R^{15}$ is a substituted phenylene group, the substituted phenylene group preferably has a halogen atom and more preferably has a fluorine atom as a substituent.

In the formula (9), in case where $R^{15}$ is a divalent group containing alkylene or fluoroalkylene units joined by an ether linkage to each other, if $R^{15}$ is a divalent group having seven or more carbon atoms containing alkylene or fluoroalkylene units joined by an ether linkage to each other, the compound represented by the formula (9) may become less soluble in a non-aqueous solvent. The number of carbon atoms of the C2-C6 divalent group containing alkylene or fluoroalkylene units joined by an ether linkage to each other is preferably up to 4.

The alkylene units in the C2-C6 divalent group are preferably a methylene unit, and the fluoroalkylene units in the C2-C6 divalent group are preferably a fluoromethylene unit.

In the formula (9), $X^6$ and $X^7$ each independently represent a hydrogen atom, a halogen atom, a substituted or unsubstituted C1-C6 alkyl group, or a substituted or unsubstituted phenyl group.

In cases where at least one of $X^6$ and $X^7$ is a substituted or unsubstituted alkyl group, if the alkyl group represented by $X^6$ or $X^7$ has seven or more carbon atoms, the compound represented by the formula (9) may become less soluble in a non-aqueous solvent. The number of carbon atoms of the alkyl group represented by $X^6$ or $X^7$ is preferably up to 4.

In the formula (9), examples of the C1-C6 alkyl group represented by $X^6$ or $X^7$ include methyl, ethyl, n-propyl, isopropyl, n-butyl, 1-methyl ethyl, n-pentyl, and n-hexyl. In particular, methyl is preferred.

In cases where the alkyl group represented by $X^6$ or $X^7$ is a substituted alkyl group, the substituted alkyl group preferably has a halogen atom and more preferably has a fluorine atom as a substituent.

In the formula (9), in cases where at least one of $X^6$ and $X^7$ is a substituted or unsubstituted phenyl group, examples of the substituted or unsubstituted phenyl group include phenyl, 2-methylphenyl, 3-methylphenyl, 4-methylphenyl, 2-ethylphenyl, 3-ethylphenyl, 4-ethylphenyl, 2-methoxyphenyl, 3-methoxyphenyl, 4-methoxyphenyl, 2-ethoxyphenyl, 3-ethoxyphenyl, 4-ethoxyphenyl, 2-(dimethylamino) phenyl, 3-(dimethylamino)phenyl, 4-(dimethylamino) phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, and 4-bromophenyl. In particular, preferred are phenyl, 2-fluorophenyl, 3-fluorophenyl, and 4-fluorophenyl because they provide a compound with a low LUMO energy susceptible to electrochemical reduction.

In particular, the cyclic disulfonic acid amide compound represented by the formula (9) is preferably a cyclic disulfonic acid amide compound represented by any of the formulas (10) to (13) because such a compound is chemically stable, forms an SEI film to prevent cell degradation due to decomposition of an electrolyte solution solvent or the like, and shows a low LUMO energy. Cyclic disulfonic acid amide compounds represented by the formulas (12) and (13) are more preferred.

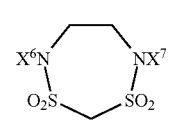

(10)

$X^6$ and $X^7$ in the formula (10) are the same as $X^6$ and $X^7$ in the formula (9), respectively.

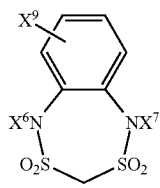

(11)

$X^6$ and $X^7$ in the formula (11) are the same as $X^6$ and $X^7$ in the formula (9), respectively. $X^8$ represents a hydrogen atom, a halogen atom, or a substituted or unsubstituted C1-C6 alkyl group.

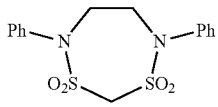

(12)

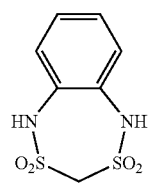

(13)

The cyclic disulfonic acid amide compound represented by the formula (9) is produced, for example, by reacting a primary or secondary diamine having —$R^{12}X^6$, —$R^{13}X^7$, and —$R^{15}$—($R^{12}$, $R^{13}$, $R^{15}$, $X^6$, and $X^7$ are the same as those in the formula (9)) with an alkylenemethanedisulfonyl chloride.

For example, the cyclic disulfonic acid amide compound represented by the formula (12) is produced by adding triethylamine dropwise to a mixture of N,N'-diphenylethylenediamine and methanedisulfonyl chloride, stirring them to complete the reaction, and then recovering the crystalized compound by filtration. In the production of the compound, a reaction solvent such as 1,2-dimethoxyethane and dichloromethane may optionally be used. The cyclic disulfonic acid amide compound represented by the formula (13) is produced by the same method as the cyclic disulfonic acid amide compound represented by the formula (12), except that o-phenylenediamine instead of N,N'-diphenylethylenediamine is allowed to react with methanedisulfonyl chloride.

The compound represented by the formula (2) is preferably a phosphorus-containing sulfonic acid amide compound represented by the formula (14):

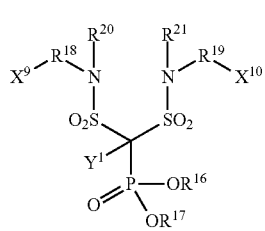

(14)

wherein $R^{16}$ and $R^{17}$ each independently represent a substituted or unsubstituted C1-C6 alkyl group or a substituted or unsubstituted phenyl group, $R^{18}$ and $R^{19}$ each independently represent a substituted or unsubstituted C0-C6 alkylene group, and $X^9$ and $X^n$ each independently represent a hydrogen atom, a substituted or unsubstituted C1-C6 alkyl group, or a substituted or unsubstituted phenyl group; and $R^{20}$ and $R^{21}$ each independently represent a hydrogen atom, a substituted or unsubstituted C1-C6 alkyl group, or —$R^{22}X^{11}$ in which $R^{22}$ represents a substituted or unsubstituted C1-C6 alkylene group and $X^{11}$ represents a substituted or unsubstituted phenyl group or a substituted or unsubstituted phenoxy group, or $R^{20}$ and $R^{21}$ may form a ring together and represent a substituted or unsubstituted C1-C6 alkylene group or a substituted or unsubstituted phenylene group, and $Y^1$ represents a hydrogen atom, a substituted or unsubstituted C1-C6 alkyl group, a substituted or unsubstituted phenyl group, or a halogen atom.

In the formula (14), $R^{16}$ and $R^{17}$ each independently represent a substituted or unsubstituted C1-C6 alkyl group or a substituted or unsubstituted phenyl group.

In the formula (14), in cases where at least one of $R^{16}$ and $R^{17}$ is an alkyl group, if the alkyl group has seven or more carbon atoms, the compound represented by the formula (9) may become less soluble in a non-aqueous solvent. The number of carbon atoms in the alkyl group represented by $R^{16}$ or $R^{17}$ is preferably up to 3.

In the formula (14), examples of the C1-C6 alkyl group represented by $R^{16}$ or $R^{17}$ include methyl, ethyl, n-propyl, isopropyl, n-butyl, 1-methyl ethyl, n-pentyl, and n-hexyl. In particular, ethyl is preferred.

In cases where the alkyl group represented by $R^{16}$ or $R^{17}$ is a substituted alkyl group, the substituted alkyl group preferably has a halogen atom and more preferably has a fluorine atom as a substituent.

In the formula (14), in cases where at least one of $R^{16}$ and $R^{17}$ is a substituted or unsubstituted phenyl group, examples of the substituted or unsubstituted phenyl group include phenyl, 2-methylphenyl, 3-methylphenyl, 4-methylphenyl, 2-ethylphenyl, 3-ethylphenyl, 4-ethylphenyl, 2-methoxyphenyl, 3-methoxyphenyl, 4-methoxyphenyl, 2-ethoxyphenyl, 3-ethoxyphenyl, 4-ethoxyphenyl, 2-(dimethylamino)phenyl, 3-(dimethylamino)phenyl, 4-(dimethylamino)phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, and 4-bromophenyl. In particular, preferred are phenyl, 2-fluorophenyl, 3-fluorophenyl, and 4-fluorophenyl because they provide a compound with a low LUMO energy susceptible to electrochemical reduction.

In the formula (14), $R^{18}$ and $R^{19}$ each independently represent a substituted or unsubstituted C0-C6 alkylene group. If $R^{18}$ and $R^{19}$ is an alkylene group having seven or more carbon atoms, the compound represented by the formula (14) may become less soluble in a non-aqueous solvent. The number of carbon atoms of the alkylene group represented by $R^{18}$ or $R^{19}$ is preferably up to 3.

In the formula (14), in cases where $R^{18}$ is a C0 alkylene group, a nitrogen atom bonded to $R^{20}$ is directly bonded to $X^9$, and in cases where $R^{19}$ is a C0 alkylene group, a nitrogen atom bonded to $R^{21}$ is directly bonded to $X^{10}$.

In the formula (14), examples of the C1-C6 alkylene group represented by $R^{18}$ or $R^{19}$ include methylene, ethylene, n-propylene, isopropylene, n-butylene, 1-methylethylene, 1-ethylethylene, n-pentylene, and n-hexylene. In particular, methylene is preferred.

In cases where the alkylene group represented by $R^{18}$ or $R^{19}$ is a substituted alkylene group, the substituted alkylene group preferably has a halogen atom and more preferably has a fluorine atom as a substituent.

In the formula (14), $X^9$ and $X^{10}$ each independently represent a hydrogen atom, a substituted or unsubstituted C1-C6 alkyl group, or a substituted or unsubstituted phenyl group.

In the formula (14), if at least one of $X^9$ and $X^{10}$ is a substituted or unsubstituted alkyl group having seven or more carbon atoms, the compound represented by the formula (14) may become less soluble in a non-aqueous solvent. The number of carbon atoms of the alkyl group represented by $X^9$ or $X^{10}$ is preferably up to 3.

In the formula (14), examples of the C1-C6 alkyl group represented by $X^9$ or $X^{10}$ include the same groups listed above as $R^{16}$ and $R^{17}$.

In cases where the alkyl group represented by $X^9$ or $X^{10}$ is a substituted alkyl group, the substituted alkyl group preferably has a halogen atom and more preferably has a fluorine atom as a substituent.

In cases where at least one of $X^9$ and $X^{10}$ is a substituted or unsubstituted phenyl group, examples of the substituted or unsubstituted phenyl group include the same groups listed above as $R^{16}$ and $R^{17}$. In particular, preferred are phenyl, 2-fluorophenyl, 3-fluorophenyl, and 4-fluorophenyl because they provide a compound with a low LUMO energy susceptible to electrochemical reduction.

In the formula (14), $R^{20}$ and $R^{21}$ each independently represent a hydrogen atom, a substituted or unsubstituted C1-C6 alkyl group, or —$R^{22}X^{11}$ which $R^{22}$ represents a substituted or unsubstituted C1-C6 alkylene group and $X^{11}$ represents a substituted or unsubstituted phenyl group or a substituted or unsubstituted phenoxy group, or $R^{20}$ and $R^{21}$ in the formula (14) may form a ring together and represent a substituted or unsubstituted C1-C6 alkylene group or a substituted or unsubstituted phenylene group.

In the formula (14), in cases where at least one of $R^{20}$ and $R^{21}$ is a substituted or unsubstituted alkyl group having seven or more carbon atoms, the compound represented by the formula (14) may become less soluble in a non-aqueous solvent. The number of carbon atoms of the alkyl group represented by $R^{20}$ or $R^{21}$ is preferably up to 3.

In the formula (14), examples of the C1-C6 alkyl group represented by $R^{20}$ or $R^{21}$ include the same groups listed above as $R^{16}$ and $R^{17}$.

In cases where the alkyl group represented by $R^{20}$ or $R^{21}$ is a substituted alkyl group, the substituted alkyl group preferably has a halogen atom and more preferably has a fluorine atom as a substituent.

In the formula (14), in cases where at least one of $R^{20}$ and $R^{21}$ is —$R^{22}X^{11}$ in which $R^{22}$ represents a substituted or unsubstituted C1-C6 alkylene group and $X^{11}$ represents a substituted or unsubstituted phenyl group or a substituted or unsubstituted phenoxy group, if $R^{22}$ is an alkylene group having seven or more carbon atoms, the compound represented by the formula (14) may become less soluble in a non-aqueous solvent. The number of carbon atoms of the alkylene group represented by $R^{22}$ is preferably up to 3.

Examples of the alkylene group represented by $R^{22}$ include the same groups listed above as $R^{18}$ and $R^{19}$.

In cases where the alkylene group represented by $R^{22}$ is a substituted alkylene group, the substituted alkylene group preferably has a halogen atom and more preferably has a fluorine atom as a substituent.

In cases where $X^{11}$ is a substituted or unsubstituted phenyl group, examples of the substituted or unsubstituted phenyl group include the same groups listed above as $R^{16}$ and $R^{17}$. In particular, preferred are phenyl, 2-fluorophenyl, 3-fluorophenyl, and 4-fluorophenyl because they provide a compound with a low LUMO energy susceptible to electrochemical reduction.

In cases where $X^{11}$ is a substituted or unsubstituted phenoxy group, examples of the substituted or unsubstituted phenoxy group include phenoxy, 2-methylphenoxy, 3-methylphenoxy, 4-methylphenoxy, 2-ethylphenoxy, 3-ethylphenoxy, 4-ethylphenoxy, 2-methoxyphenoxy, 3-methoxyphenoxy, 4-methoxyphenoxy, 2-ethoxyphenoxy, 3-ethoxyphenoxy, 4-ethoxyphenoxy, 2-(dimethylamino)phenoxy, 3-(dimethylamino)phenoxy, 4-(dimethylamino)phenoxy, 2-fluorophenoxy, 3-fluorophenoxy, 4-fluorophenoxy, 2-chlorophenoxy, 3-chlorophenoxy, 4-chlorophenoxy, 2-bromophenoxy, 3-bromophenoxy, and 4-bromophenoxy. In particular, preferred are phenoxy, 2-fluorophenoxy, 3-fluorophenoxy, and 4-fluorophenoxy because they provide a compound with a low LUMO energy susceptible to electrochemical reduction.

In the formula (14), in case where $R^{20}$ and $R^{21}$ may together represent a substituted or unsubstituted alkylene group, if the alkylene group is an alkylene group having seven or more carbon atoms, the compound represented by the formula (14) may become less soluble in a non-aqueous solvent. The number of carbon atoms of the alkylene group is preferably up to 3.

Examples of the alkylene group represented by $R^{20}$ and $R^{21}$ together include the same groups listed above as $R^{18}$ and $R^{19}$.

In cases where the alkylene group represented by $R^{20}$ and $R^{21}$ together is a substituted alkylene group, the substituted alkylene group preferably has a halogen atom and more preferably has a fluorine atom as a substituent.

In the formula (14), in cases where $R^{20}$ and $R^{21}$ together represent a substituted phenylene group, the substituted phenylene group preferably has a halogen atom and more preferably has a fluorine atom.

In the formula (14), $Y^1$ represents a hydrogen atom, a substituted or unsubstituted C1-C6 alkyl group, a substituted or unsubstituted phenyl group, or a halogen atom.

Examples of the C1-C6 alkyl group represented by $Y^1$ include the same groups listed above as $R^{16}$ and $R^{17}$.

In cases where $Y^1$ is a substituted alkyl group, the substituted alkyl group preferably has a halogen atom and more preferably has a fluorine atom as a substituent.

In the formula (14), in cases where $Y^1$ is a substituted or unsubstituted phenyl group, examples of the substituted or unsubstituted phenyl group include the same groups listed above as $R^{16}$ and $R^{17}$. In particular, preferred are phenyl, 2-fluorophenyl, 3-fluorophenyl, and 4-fluorophenyl because they provide a compound with a low LUMO energy susceptible to electrochemical reduction.

In the formula (14), in cases where $Y^1$ is a halogen atom, the halogen atom is preferably a fluorine atom.

The phosphorus-containing sulfonic acid amide compound represented by the formula (14) is particularly preferably a phosphorus-containing sulfonic acid amide compound represented by any of the formulas (15) and (16) because such a compound is chemically stable, forms an SEI film to prevent cell degradation due to decomposition of an electrolyte solution or the like, and shows a low LUMO energy.

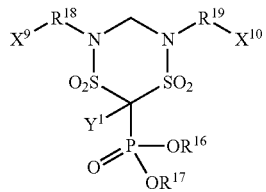

(15)

$R^{16}$, $R^{17}$, $R^{18}$, $R^{19}$, $X^9$, $X^{10}$, and $Y^1$ in the formula (15) are the same as $R^{16}$, $R^{17}$, $R^{18}$, $R^{19}$, $X^9$, $X^{10}$, and $Y^1$ in the formula (14), respectively.

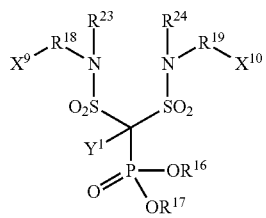

(16)

$R^{16}$, $R^{17}$, $R^{18}$, $R^{19}$, $X^9$, $X^{10}$, and $Y^1$ in the formula (16) are the same as $R^{16}$, $R^{17}$, $R^{18}$, $R^{19}$, $X^9$, $X^{10}$, and $Y^1$ in the formula (14), respectively. $R^{23}$ and $R^{24}$ each independently represent a hydrogen atom, a substituted or unsubstituted C1-C6 alkyl group, or —$R^{22}X^{11}$ in which $R^{22}$ represents a substituted or unsubstituted C1-C6 alkylene group and $X^{11}$ represents a substituted or unsubstituted phenyl group or a substituted or unsubstituted phenoxy group.

In the formula (16), examples of the substituted or unsubstituted C1-C6 alkyl group represented by $R^{23}$ or $R^{24}$, the substituted or unsubstituted C1-C6 alkylene group represented by $R^{22}$, and the substituted or unsubstituted phenyl group and the substituted or unsubstituted phenoxy group each represented by $X^{11}$ include the same groups listed above as $R^{20}$ and $R^{21}$ in the formula (14).

The phosphorus-containing sulfonic acid amide compound represented by the formula (14) is produced, for example, by reacting bromoacetic acid with trialkyl phosphite, followed by reaction with chlorosulfonic acid, and further reacting the resulting product with an amine.

For example, a phosphorus-containing sulfonic acid amide compound represented by the formula (15) in which $R^{16}$ is ethyl, $R^{17}$ is ethyl, $R^{18}$ is methylene, $R^{19}$ is methylene, $X^9$ is methyl, $X^{10}$ is methyl, and $Y^1$ is hydrogen is produced by reacting bromoacetic acid with triethyl phosphite, followed by reaction with chlorosulfonic acid, and reacting the resulting product with N,N'-diethylmethylenediamine.

Further, a phosphorus-containing sulfonic acid amide compound represented by the formula (16) in which $R^{16}$ is ethyl, $R^{17}$ is ethyl, $R^{18}$ is methylene, $R^{19}$ is methylene, $R^{23}$ is methyl, $R^{24}$ is methyl, $X^9$ is phenyl, $X^{10}$ is phenyl, and $Y^1$ is hydrogen is produced by reacting bromoacetic acid with triethyl phosphite, followed by reaction with chlorosulfonic acid, and reacting the resulting product with benzylmethylamine.

For example, when $LiPF_6$ is used as an electrolyte, use of an additive for a non-aqueous electrolyte solution formed from the phosphorus-containing sulfonic acid amide compound represented by the formula (14) suppresses generation of gas derived from $PF_5$ generated by decomposition of $LiPF_6$. Although the reasons are not known, $PF_5$ is coordinated to >P=O contained in the phosphorus-containing sulfonic acid amide compound represented by the formula (14) to be less activated, which may further improve cell performance more.

The compound represented by the formula (2) is preferably a disulfonic acid amide compound represented by the formula (17):

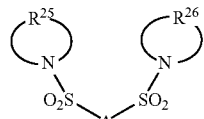

(17)

wherein $R^{25}$ and $R^{26}$ each independently represent a C1-C6 alkylene group or a C1-C6 alkylene group having an oxygen atom, a nitrogen atom which may have a substituent, or a sulfur atom, in a carbon chain or at an end of a chain, A represents $C_mH_{(2m-n)}Z_n$, m being an integer of 1 to 6, n being an integer of 0 to 12, Z representing a substituted or unsubstituted C1-C4 alkyl group, a silyl group, a phosphonic acid ester group, an acyl group, a cyano group, or a nitro group.

The "C1-C6 alkylene group having an oxygen atom, a nitrogen atom which may have a substituent, or a sulfur atom, in a carbon chain or at an end of a chain" represented by $R^{25}$ or $R^{26}$ is a group in which an oxygen atom, a nitrogen atom which may have a substituent, or a sulfur atom is contained in a carbon chain or at an end of a chain of "the C1-C6 alkylene group". Examples of such a group include —O—$CH_2$—, —O—$(CH_2)_2$—, —O—$(CH_2)_3$—, —O—$(CH_2)_4$—, —O—$(CH_2)_5$—, —O—$(CH_2)_6$—, —$CH_2$—O—$CH_2$—, —$CH_2$—O—$(CH_2)_2$—, —$CH_2$—O—$(CH_2)_3$—, —$CH_2$—O—$(CH_2)_4$—, —$CH_2$—O—$(CH_2)_5$—, —$(CH_2)_2$—O—$(CH_2)_2$—, —$(CH_2)_2$—O—$(CH_2)_3$—, —$(CH_2)_2$—O—$(CH_2)_4$—, —$(CH_2)_3$—O—$(CH_2)_3$—, —N—$CH_2$—, —N—$(CH_2)_2$—, —N—$(CH_2)_3$—, —N—$(CH_2)_4$—, —N—$(CH_2)_5$—, —N—$(CH_2)_6$—, —$CH_2$—N—$CH_2$—, —$CH_2$—N—$(CH_2)_2$—, —$CH_2$—N—$(CH_2)_3$—, —$CH_2$—N—$(CH_2)_4$—, —$CH_2$—N—$(CH_2)_5$—, —$(CH_2)_2$—N—$(CH_2)_2$—, —$(CH_2)_2$—N—$(CH_2)_3$—, —$(CH_2)_2$—N—$(CH_2)_4$—, —$(CH_2)_3$—N—$(CH_2)_3$—, —$N(CH_3)$—$CH_2$—, —$N(CH_3)$—$(CH_2)_2$—, —$N(CH_3)$—$(CH_2)_3$—, —$N(CH_3)$—$(CH_2)_4$—, —$N(CH_3)$—$(CH_2)_5$—, —$N(CH_3)$—$(CH_2)_6$—, —$CH_2$—$N(CH_3)$—$CH_2$—, —$CH_2$—$N(CH_3)$—$(CH_2)_2$—, —$CH_2$—$N(CH_3)$—$(CH_2)_3$—, —$CH_2$—$N(CH_3)$—$(CH_2)_4$—, —$CH_2$—$N(CH_3)$—$(CH_2)_5$—, —$(CH_2)_2$—$N(CH_3)$—$(CH_2)_2$—, —$(CH_2)_2$—$N(CH_3)$—$(CH_2)_3$—, —$(CH_2)_2$—$N(CH_3)$—$(CH_2)_4$—, —$(Ch_2)_3$—$N(CH_3)$—$(CH_2)_3$—, —S—$CH_2$—, —S—$(CH_2)_2$—, —S—$(CH_2)_3$—, —S—$(Ch_2)_4$—, —S—$(CH_2)_5$—, —S—$(CH_2)_6$—, —$CH_2$—S—$CH_2$—, —$CH_2$—S—$(CH_2)_2$—, —$CH_2$—S—$(CH_2)_3$—, —$CH_2$—S—$(CH_2)_4$—, —$CH_2$—S—$(CH_2)_5$—, —$(CH_2)_2$—S—$(CH_2)_2$—, —$(CH_2)_2$—S—$(CH_2)_3$—, —$(CH_2)_2$—S—$(CH_2)_4$—, or —$(CH_2)_3$—S—$(CH_2)_3$—. Preferred are C2-C4 alkylene groups having an oxygen atom, a nitrogen atom which may have a substituent, or a sulfur atom, in a carbon chain or at an end of a chain, and more preferred are groups having —$(CH_2)_2$—O—$(CH_2)_2$—, —$(CH_2)_2$—N—$(CH_2)_2$—, —$(CH_2)_2$—$N(CH_3)$—$(CH_2)_2$—, or —$(CH_2)_2$—S—$(CH_2)_2$.

In the formula (17), a ring formed by $R^{25}$ and a nitrogen atom bonded to a sulfonyl group and a ring formed by $R^{26}$ and a nitrogen atom bonded to a sulfonyl group are each preferably a five- or six-membered ring. If the ring is a three- or four-membered ring, the compound represented by the formula (17) may be less likely to be produced. If the ring is a seven- or more membered ring, the compound represented by the formula (17) may become less soluble in a non-aqueous solvent.

In the formula (17), A represents $C_mH_{(2m-n)}Z_n$ in which m is an integer of 1 to 6, n is an integer of 0 to 12, and Z represents a substituted or unsubstituted alkyl group, a silyl group, a phosphonic acid ester group, an acyl group, a cyano group, or a nitro group. m is preferably up to 4 and more preferably up to 2. A is preferably methylene or ethylene. In cases where Z is a substituted alkyl group, at least one or all of the hydrogen atoms of the alkyl group are preferably replaced by a fluorine atom.

Examples of the disulfonic acid amide compound represented by the formula (17) include methanedisulfonic acid bispyrrolidine, methanedisulfonic acid bispiperidine, methanedisulfonic acid bismorpholine, methanedisulfonic acid bisthiomorpholine, 1,2-ethanedisulfonic acid bismorpholine, methanedisulfonic acid bis(1-methylpiperazine), 1,1-ethanedisulfonic acid bismorpholine, ethane-1,1-disulfonic acid bispyrrolidine, ethane-1,1-disulfonic acid bispiperidine, propane-1,1-disulfonic acid bispyrrolidine, propane-1,1-disulfonic acid bispiperidine, propane-1,1-disulfonic acid bismorpholine, 2-oxopropane-1,1-disulfonic acid bispyrrolidine, 2-oxopropane-1,1-disulfonic acid bismorpholine, 2-oxo-2-phenyl-ethane-1,1-disulfonic acid bispyrrolidine, 2-oxo-2-phenyl-ethane-1,1-disulfonic acid bismorpholine, bis(morpholine-sulfonyl) diethyl methyl phosphate, and trimethyl silanyl-methanedisulfonic acid bismorpholine. In particular, preferred are methanedisulfonic acid bispyrrolidine, methanedisulfonic acid bispiperidine, methanedisulfonic acid bismorpholine, methanedisulfonic acid bisthiomorpholine, 1,2-ethanedisulfonic acid bismorpholine, and methanedisulfonic acid bis(1-methylpiperazine) because they are easily produced and have excellent storage stability.

The disulfonic acid amide compound represented by the formula (17) is produced, for example, by reacting a cyclic secondary amine including $R^{25}$ and a NH group, a cyclic secondary amine including $R^{26}$ and a NH group ($R^{25}$ and $R^{26}$ are the same as those in the formula (17)), a compound having a group represented by A (A is the same as that in the formula (17)) between two chlorosulfonyl groups.

For example, methanedisulfonic acid bispyrrolidine is produced by adding methanedisulfonyl chloride dropwise to pyrrolidine, followed by dropwise addition of triethylamine, stirring them to complete the reaction, extracting a target compound into an organic phase, and recovering the crystalized compound by filtration. In the production of the compound, a reaction solvent such as 1,2-dimethoxyethane may be optionally used.

The disulfonyl compound according to the present invention is preferably a compound represented by the formula (18):

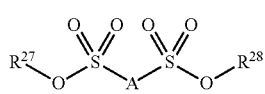

(18)

wherein A represents $C_mH_{(2m-n)}Z_n$, m being an integer of 1 to 6, n being an integer of 0 to 12, Z representing a substituted or unsubstituted alkyl group, a silyl group, a phosphonic acid ester group, an acyl group, a cyano group, or a nitro group; and $R^{27}$ and $R^{28}$ each independently represent a hydrogen atom, a substituted or unsubstituted C1-C10 alkyl group, a substituted or unsubstituted C2-C10 alkenyl group, a substituted or unsubstituted phenyl group, or a substituted or unsubstituted phenoxy group, or $R^{27}$ and $R^{28}$ may form a ring together and represent a substituted or unsubstituted C1-C6 alkylene group or a substituted or unsubstituted phenylene group.

The compound represented by the formula (18) is preferably a halogen-containing disulfonic acid ester compound represented by the formula (19):

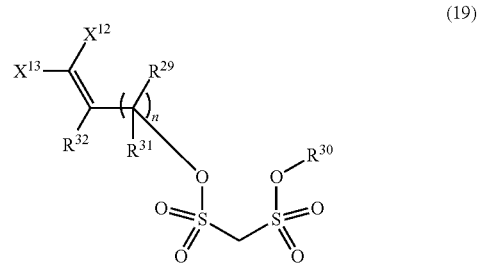

(19)

wherein $R^{29}$, $R^{31}$, and $R^{32}$ each independently represent a hydrogen atom, a substituted or unsubstituted C1-C5 alkyl group, a halogen atom, or a substituted or unsubstituted phenyl group, $R^{30}$ represents a hydrogen atom, a substituted or unsubstituted C1-C10 alkyl group, a substituted or unsubstituted C2-C10 alkenyl group, or a substituted or unsubstituted phenyl group, $X^{12}$ and $X^{13}$ each independently represent a halogen atom, and n represents an integer of 0 to 5.

In the formula (19), in cases where at least one of $R^{29}$, $R^{31}$, and $R^{32}$ is a substituted or unsubstituted alkyl group, if the alkyl group is an alkyl group having six or more carbon atoms, the compound represented by the formula (19) may become less soluble in a non-aqueous solvent. The number of carbon atoms of the alkyl group is preferably up to 3.

In cases where the alkyl group is a substituted alkyl group, the substituted alkyl group preferably has a halogen atom and more preferably has a fluorine atom as a substituent.

In the formula (19), in cases where at least one of $R^{29}$, $R^{31}$, and $R^{32}$ is a substituted or unsubstituted phenyl group, examples of the substituted or unsubstituted phenyl group include phenyl, 2-methylphenyl, 3-methylphenyl, 4-methylphenyl, 2-ethylphenyl, 3-ethylphenyl, 4-ethylphenyl, 2-methoxyphenyl, 3-methoxyphenyl, 4-methoxyphenyl, 2-ethoxyphenyl, 3-ethoxyphenyl, 4-ethoxyphenyl, 2-(dimethylamino)phenyl, 3-(dimethylamino)phenyl, 4-(dimethylamino)phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, and 4-bromophenyl. In particular, preferred are phenyl, 2-fluorophenyl, 3-fluorophenyl, and 4-fluorophenyl because they provide a compound with a low LUMO energy susceptible to electrochemical reduction.

In the formula (19), $R^{30}$ represents a hydrogen atom, a substituted or unsubstituted C1-010 alkyl group, a substituted or unsubstituted C2-C10 alkenyl group, or a substituted or unsubstituted phenyl group.

In the formula (19), in cases where $R^{30}$ is a substituted or unsubstituted alkyl group, if the alkyl group has 11 or more carbon atoms, the compound represented by the formula

(19) may become less soluble in a non-aqueous solvent. The number of carbon atoms of the alkyl group is preferably up to 4.

In cases where the alkyl group is a substituted alkyl group, the substituted alkyl group preferably has a halogen atom and more preferably has a fluorine atom as a substituent.

In the formula (19), in cases where $R^{30}$ is a substituted or unsubstituted alkenyl group, if the alkenyl group has 11 or more carbon atoms, the compound represented by the formula (19) may become less soluble in a non-aqueous solvent. The number of carbon atoms of the alkenyl group is preferably up to 4.

In cases where the alkenyl group is a substituted alkenyl group, the substituted alkenyl group preferably has a halogen atom and more preferably has a fluorine atom as a substituent.

In the formula (19), in cases where $R^{30}$ is a substituted or unsubstituted phenyl group, examples of the substituted or unsubstituted phenyl group include the same groups listed above as $R^{29}$, $R^{31}$, and $R^{32}$. In particular, preferred are phenyl, 2-fluorophenyl, 3-fluorophenyl, and 4-fluorophenyl because they provide a compound with a low LUMO energy susceptible to electrochemical reduction.

In the formula (19), the halogen atom represented by $X^{12}$ or $X^{13}$ is, for example, a fluorine atom, a chlorine atom, a bromine atom, or an iodine atom. In particular, a fluorine atom is preferred.

In the formula (19), n represents an integer of 0 to 5. In particular, n is preferably not more than 2 and more preferably not more than 1 in view of the solubility in a non-aqueous solvent In particular, the halogen-containing disulfonic acid ester compound represented by the formula (19) is preferably a halogen-containing disulfonic acid ester compound represented by any of the formulas (20) to (23) and more preferably a halogen-containing disulfonic acid ester compound represented by any of the formulas (21) and (23) because of its low LUMO energy.

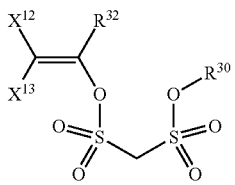

(20)

$R^{30}$, $R^{32}$, $X^{12}$, and $X^{13}$ in the formula (20) are the same as $R^{30}$, $R^{32}$, $X^{12}$, and $X^{13}$ in the formula (19), respectively.

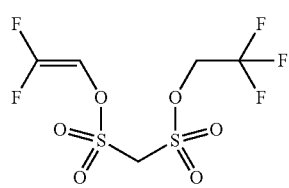

(21)

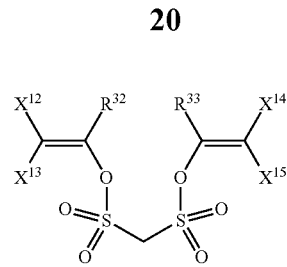

(22)

$R^{32}$, $X^{12}$, and $X^{13}$ in the formula (22) are the same as $R^{32}$, $X^{12}$ and $X^{13}$ in the formula (19), respectively. $R^{33}$ represents a hydrogen atom, a substituted or unsubstituted C1-C5 alkyl group, or a substituted or unsubstituted phenyl group. $X^{14}$ and $X^{15}$ each independently represent a halogen atom.

The formula (22) represents a compound represented by the formula (19) in which n is 0 and $R^{30}$ is a substituted or unsubstituted ethylenyl group. Therefore, in the formula (22), the total of the number of carbon atoms of $R^{33}$ and the number of carbon atoms of an ethylenyl group bonded to $R^{33}$ is set to a number not exceeding the number of carbon atoms of $R^{30}$ in the formula (19).

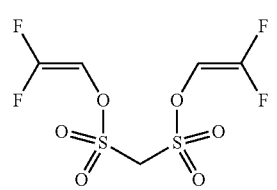

(23)

The halogen-containing disulfonic acid ester compound represented by the formula (19) is produced, for example, by reacting methanedisulfonyl chloride with a trihalogenated alcohol and then carrying out the vinylation.

For example, the halogen-containing disulfonic acid ester compound represented by the formula (21) is produced as follows. Methanedisulfonyl chloride is added dropwise to trifluoroethanol, followed by dropwise addition of triethylamine, they are reacted, methanedisulfonic acid bis(2,2,2-trifluoroethyl ester) is crystallized, the resulting methanedisulfonic acid bis(2,2,2-trifluoroethyl ester) is dissolved into a solvent, a n-butyllithium-hexane solution is added dropwise to the solution in an amount of 4 mole equivalent for the methanedisulfonic acid bis(2,2,2-trifluoroethyl ester), and the solution is reacted.

Further, the halogen-containing disulfonic acid ester compound represented by the formula (23) is produced by the same as the halogen-containing disulfonic acid ester compound represented by the formula (21) except that the amount of the n-butyllithium-hexane solution is 8 mole equivalent for the methanedisulfonic acid bis(2,2,2-trifluoroethyl ester).

In the production of the compound, a base such as tributylamine may be used instead of triethylamine, or a base such as t-butyllithium may be used instead of n-butyllithium, if necessary.

The compound represented by the formula (18) is preferably a phosphorus-containing sulfonic acid ester compound represented by the formula (24):

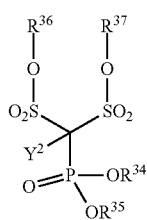

(24)

wherein $R^{34}$ and $R^{35}$ each independently represent a substituted or unsubstituted C1-C6 alkyl group or a substituted or unsubstituted phenyl group; and $R^{36}$ and $R^{37}$ each independently represent a substituted or unsubstituted C1-C6 alkyl group, a substituted or unsubstituted phenyl group, or a substituted or unsubstituted phenoxy group, or $R^{36}$ and $R^{37}$ may form a ring together and represent a substituted or unsubstituted C1-C6 alkylene group or a substituted or unsubstituted phenylene group; and $Y^2$ represents a hydrogen atom, a substituted or unsubstituted C1-C6 alkyl group, a substituted or unsubstituted phenyl group, or a halogen atom.

In the formula (24), $R^{34}$ and $R^{35}$ each independently represent a substituted or unsubstituted C1-C6 alkyl group or a substituted or unsubstituted phenyl group.

In the formula (24), in cases where at least one of $R^{34}$ and $R^{35}$ is an alkyl group, if the alkyl group represented by $R^{34}$ or $R^{35}$ is an alkyl group having seven or more carbon atoms, the compound represented by the formula (24) may become less soluble in a non-aqueous solvent. The number of carbon atoms of the alkyl group represented by $R^{34}$ or $R^{35}$ is preferably up to 3.

In the formula (24), examples of the C1-C6 alkyl group represented by $R^{34}$ or $R^{35}$ include methyl, ethyl, n-propyl, isopropyl, n-butyl, 1-methyl ethyl, n-pentyl, and n-hexyl. In particular, ethyl is preferred.

In cases where $R^{34}$ and $R^{35}$ are each a substituted alkyl group, the alkyl group preferably has a halogen atom and more preferably has a fluorine atom as a substituent.

In the formula (24), in cases where at least one of $R^{34}$ and $R^{35}$ is a substituted or unsubstituted phenyl group, examples of the substituted or unsubstituted phenyl group include phenyl, 2-methylphenyl, 3-methylphenyl, 4-methylphenyl, 2-ethylphenyl, 3-ethylphenyl, 4-ethylphenyl, 2-methoxyphenyl, 3-methoxyphenyl, 4-methoxyphenyl, 2-ethoxyphenyl, 3-ethoxyphenyl, 4-ethoxyphenyl, 2-(dimethylamino)phenyl, 3-(dimethylamino)phenyl, 4-(dimethylamino)phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, and 4-bromophenyl. In particular, preferred are phenyl, 2-fluorophenyl, 3-fluorophenyl, and 4-fluorophenyl because they provide a compound with a low LUMO energy susceptible to electrochemical reduction.

In the formula (24), $R^{36}$ and $R^{37}$ each independently represent a substituted or unsubstituted C1-C6 alkyl group, a substituted or unsubstituted phenyl group, or a substituted or unsubstituted phenoxy group; or $R^{36}$ and $R^{37}$ may form a ring together and represent a substituted or unsubstituted C1-C6 alkylene group or a substituted or unsubstituted phenylene group.

In the formula (24), in cases where at least one of $R^{36}$ and $R^{37}$ is a substituted or unsubstituted alkyl group, if the alkyl group represented by $R^{36}$ or $R^{37}$ is an alkyl group having seven or more carbon atoms, the compound represented by the formula (24) may become less soluble in a non-aqueous solvent. The number of carbon atoms of the alkyl group represented by $R^{36}$ or $R^{37}$ is preferably up to 3.

In the formula (24), examples of the C1-C6 alkyl group represented by $R^{36}$ or $R^{37}$ include the same groups listed above as $R^{34}$ and $R^{35}$.

Further, in cases where the alkyl group represented by $R^{36}$ or $R^{37}$ is a substituted alkyl group, the alkyl group preferably has a halogen atom and more preferably has a fluorine atom as a substituent.

In the formula (24), in cases where at least one of $R^{36}$ and $R^{37}$ is a substituted or unsubstituted phenyl group, examples of the substituted or unsubstituted phenyl group include the same groups listed above as $R^{34}$ and $R^{35}$. In particular, preferred are phenyl, 2-fluorophenyl, 3-fluorophenyl, and 4-fluorophenyl because they provide a compound with a low LUMO energy susceptible to electrochemical reduction.

In the formula (24), in cases where at least one of $R^{36}$ and $R^{37}$ is a substituted or unsubstituted phenoxy group, examples of the substituted or unsubstituted phenoxy group include phenoxy, 2-methylphenoxy, 3-methylphenoxy, 4-methylphenoxy, 2-ethylphenoxy, 3-ethylphenoxy, 4-ethylphenoxy, 2-methoxyphenoxy, 3-methoxyphenoxy, 4-methoxyphenoxy, 2-ethoxyphenoxy, 3-ethoxyphenoxy, 4-ethoxyphenoxy, 2-(dimethylamino)phenoxy, 3-(dimethylamino)phenoxy, 4-(dimethylamino)phenoxy, 2-fluorophenoxy, 3-fluorophenoxy, 4-fluorophenoxy, 2-chlorophenoxy, 3-chlorophenoxy, 4-chlorophenoxy, 2-bromophenoxy, 3-bromophenoxy, and 4-bromophenoxy. In particular, preferred are phenoxy, 2-fluorophenoxy, 3-fluorophenoxy, and 4-fluorophenoxy because they provide a compound with a low LUMO energy susceptible to electrochemical reduction.

In the formula (24), in cases where $R^{36}$ and $R^{37}$ together represent a substituted or unsubstituted alkylene group, if the alkylene group has seven or more carbon atoms, the compound represented by the formula (24) may become less soluble in a non-aqueous solvent. The number of carbon atoms of the alkylene group is preferably up to 2.

Examples of the alkylene group include methylene, ethylene, n-propylene, isopropylene, n-butylene, 1-methylethylene, 1-ethylethylene, n-pentylene, and n-hexylene. In particular, methylene is preferred.

In cases where the alkylene group is a substituted alkylene group, the alkylene group preferably has a halogen atom and more preferably has a fluorine atom as a substituent.

In the formula (24), $R^{36}$ and $R^{37}$ together represent a substituted phenylene group, the phenylene group preferably has a halogen atom and more preferably has a fluorine atom as a substituent.

In the formula (24), $Y^2$ represents a hydrogen atom, a substituted or unsubstituted C1-C6 alkyl group, a substituted or unsubstituted phenyl group, or a halogen atom.

Examples of the C1-C6 alkyl group represented by $Y^2$ include the same groups listed above as $R^{34}$ and $R^{35}$.

In addition, in cases where the alkyl group represented by $Y^2$ is a substituted alkyl group, the alkyl group preferably has a halogen atom and more preferably has a fluorine atom as a substituent.

In the formula (24), in cases where $Y^2$ is a substituted or unsubstituted phenyl group, examples of the substituted or unsubstituted phenyl group include the same groups listed above as $R^{34}$ and $R^{35}$. In particular, preferred are phenyl, 2-fluorophenyl, 3-fluorophenyl, and 4-fluorophenyl because they provide a compound with a low LUMO energy susceptible to electrochemical reduction.

In the formula (24), in cases where $Y^2$ is a halogen atom, the halogen atom is preferably a fluorine atom.

The phosphorus-containing sulfonic acid ester compound represented by the formula (24) is preferably a phosphorus-containing sulfonic acid ester compound represented by any of the formulas (25) and (26) because such a compound is chemically stable, forms an SEI film to prevent cell degradation due to decomposition of an electrolyte solution or the like, and shows a low LUMO energy.

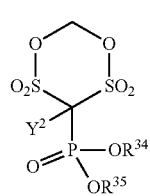

(25)

$R^{34}$, $R^{35}$, and $Y^2$ in the formula (25) are the same as $R^{34}$, $R^{35}$, and $Y^2$ in the formula (24), respectively.

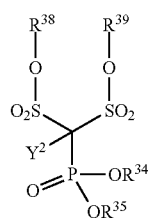

(26)

$R^{34}$, $R^{35}$, and $Y^2$ in the formula (26) are the same as $R^{34}$, $R^{35}$, and $Y^2$ in the formula (24), respectively. $R^{38}$ and $R^{39}$ each independently represent a substituted or unsubstituted C1-C6 alkyl group, a substituted or unsubstituted phenyl group, or a substituted or unsubstituted phenoxy group.

Examples of the substituted or unsubstituted C1-C6 alkyl group, the substituted or unsubstituted phenyl group, and the substituted or unsubstituted phenoxy group represented by $R^{38}$ or $R^{39}$ in the formula (26) include the same groups listed above as $R^{36}$ and $R^{37}$ in the formula (24).

The phosphorus-containing sulfonic acid ester compound represented by the formula (24) is produced, for example, by reacting bromoacetic acid with a trialkyl phosphite, followed by reaction with chlorosulfonic acid, and further reacting the resulting product with paraformaldehyde; or by reacting bromoacetic acid with a trialkyl phosphite, followed by reaction with chlorosulfonic acid, and further reacting the resulting product with an alcohol.

For example, the phosphorus-containing sulfonic acid ester compound represented by the formula (25) in which $R^{34}$ is ethyl, $R^{35}$ is ethyl, and $Y^2$ is hydrogen is produced by reacting bromoacetic acid with triethyl phosphite, followed by reaction with chlorosulfonic acid, hydrolyzing the resulting product, and reacting the hydrolyzed product with paraformaldehyde.

The phosphorus-containing sulfonic acid ester compound represented by the formula (26) in which $R^{34}$ is ethyl, $R^{35}$ is ethyl, $R^{38}$ is ethyl, $R^{39}$ is ethyl, and $Y^2$ is hydrogen is produced by reacting bromoacetic acid with triethyl phosphite, followed by reaction with chlorosulfonic acid, and reacting the resulting product with ethanol.

For example, when $LiPF_6$ is used as an electrolyte, use of an additive for a non-aqueous electrolyte solution formed from the phosphorus-containing sulfonic acid amide compound represented by the formula (24) suppresses generation of gas derived from $PF_5$ generated by decomposition of $LiPF_6$. Although the details of the reasons are not clear, $PF_5$ is coordinated to >P=O contained in the phosphorus-containing sulfonic acid amide compound represented by the formula (24) to be less activated, which may further improve cell performance.

Further, the disulfonyl compound according to the present invention is preferably a silyl sulfonic acid ester compound represented by the formula (27).

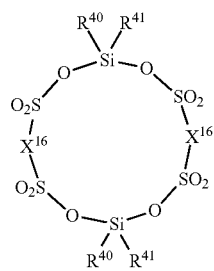

(27)

In the formula (27), $R^{40}$ and $R^{41}$ each independently represent a substituted or unsubstituted C1-C6 alkyl group, a substituted or unsubstituted phenyl group, or a substituted or unsubstituted phenoxy group. $X^{16}$ represents a substituted or unsubstituted C1-C6 alkylene group.

The silyl sulfonic acid ester compound represented by the formula (27) has two Si atoms per molecule as an active center, and therefore easily forms a stable SEI containing more silyl groups. As a result, a cycle performance can be improved or internal resistance can be reduced. Further, the silyl sulfonic acid ester compound represented by the formula (27) has a larger ring than conventional silyl-containing additives, and is therefore less likely to be decomposed by moisture in an electrolyte solution or the air, which provides industrial advantages in production.

In the formula (27), $R^{40}$ and $R^{41}$ each independently represent a substituted or unsubstituted C1-C6 alkyl group, a substituted or unsubstituted phenyl group, or a substituted or unsubstituted phenoxy group.

In the formula (27), in cases where at least one of $R^{40}$ and $R^{41}$ is a substituted or unsubstituted alkyl group, if the alkyl group represented by $R^{40}$ or $R^{41}$ is an alkyl group having seven or more carbon atoms, the compound represented by the formula (27) may become less soluble in a non-aqueous solvent. The number of carbon atoms of the alkyl group represented by $R^{40}$ or $R^{41}$ is preferably up to 3.

In the formula (27), examples of the C1-C6 alkyl group represented by $R^{40}$ or $R^{41}$ include methyl, ethyl, n-propyl, isopropyl, n-butyl, 1-methyl ethyl, n-pentyl, and n-hexyl. In particular, preferred are methyl, ethyl, n-propyl, and isopropyl.

In cases where the alkyl group represented by $R^{40}$ or $R^{41}$ is a substituted alkyl group, the alkyl group preferably has a halogen atom and more preferably has a fluorine atom as a substituent.

In the formula (27), in cases where at least one of $R^{40}$ and $R^{41}$ is a substituted or unsubstituted phenyl group, examples of the substituted or unsubstituted phenyl group include phenyl, 2-methylphenyl, 3-methylphenyl, 4-methylphenyl, 2-ethylphenyl, 3-ethylphenyl, 4-ethylphenyl, 2-methoxyphenyl, 3-methoxyphenyl, 4-methoxyphenyl, 2-ethoxyphenyl, 3-ethoxyphenyl, 4-ethoxyphenyl, 2-(dimethylamino) phenyl, 3-(dimethylamino)phenyl, 4-(dimethylamino) phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, and 4-bromophenyl. In particular, preferred are phenyl, 2-fluorophenyl, 3-fluorophenyl, and 4-fluorophenyl because they provide a compound with a low LUMO energy susceptible to electrochemical reduction.

In the formula (27), in cases where at least one of $R^{40}$ and $R^{41}$ is a substituted or unsubstituted phenoxy group, examples of the substituted or unsubstituted phenoxy group include phenoxy, 2-methylphenoxy, 3-methylphenoxy, 4-methylphenoxy, 2-ethylphenoxy, 3-ethylphenoxy, 4-ethylphenoxy, 2-methoxyphenoxy, 3-methoxyphenoxy, 4-methoxyphenoxy, 2-ethoxyphenoxy, 3-ethoxyphenoxy, 4-ethoxyphenoxy, 2-(dimethylamino)phenoxy, 3-(dimethylamino)phenoxy, 4-(dimethylamino)phenoxy, 2-fluorophenoxy, 3-fluorophenoxy, 4-fluorophenoxy, 2-chlorophenoxy, 3-chlorophenoxy, 4-chlorophenoxy, 2-bromophenoxy, 3-bromophenoxy, and 4-bromophenoxy. In particular, preferred are phenoxy, 2-fluorophenoxy, 3-fluorophenoxy, and 4-fluorophenoxy because they provide a compound with a low LUMO energy susceptible to electrochemical reduction.

In the formula (27), $X^{16}$ represents a substituted or unsubstituted C1-C6 alkylene group. If the alkylene group represented by $X^{16}$ is an alkylene group having seven or more carbon atoms, the compound represented by the formula (27) may become less soluble in a non-aqueous solvent. The number of carbon atoms of the alkylene group represented by $X^{16}$ is preferably up to 2.

In the formula (27), examples of the C1-C6 alkylene group represented by $X^{16}$ include methylene, ethylene, n-propylene, isopropylene, n-butylene, 1-methylethylene, 1-ethylethylene, n-pentylene, and n-hexylene. In particular, preferred are methylene and ethylene.

Further, in cases where the alkylene group represented by $X^{16}$ is a substituted alkylene group, the alkylene group preferably has a C1-C6 alkoxy group, a halogen atom, a substituted or unsubstituted phenyl group, or a substituted or unsubstituted phenoxy group as a substituent. In particular, preferred are a halogen atom and a substituted or unsubstituted phenyl group.

In the formula (27), in cases where the alkylene group represented by $X^{16}$ has an alkoxy group as a substituent, if the alkoxy group had seven or more carbon atoms, the compound represented by the formula (27) may become less soluble in a non-aqueous solvent. The number of carbon atoms of the alkoxy group is preferably up to 6.

Examples of the alkoxy group include methoxy, ethoxy, n-propyloxy, isopropyloxy, n-butyloxy, 1-methyl ethoxy, pentyloxy, and hexyloxy. In particular, methoxy is preferred.

In the formula (27), in cases where the alkylene group represented by $X^{16}$ has a halogen atom as a substituent, the halogen atom is preferably a fluorine atom.

In the formula (27), in cases where the alkylene group represented by $X^{16}$ has a substituted or unsubstituted phenyl group as a substituent, examples of the substituted or unsubstituted phenyl group include the same groups listed above as $R^{40}$ and $R^{41}$. In particular, preferred are phenyl, 2-fluorophenyl, 3-fluorophenyl, and 4-fluorophenyl because they provide a compound with a low LUMO energy susceptible to electrochemical reduction.

In the formula (27), in cases where the alkylene group represented by $X^{16}$ has a substituted or unsubstituted phenoxy group as a substituent, examples of the substituted or unsubstituted phenoxy group include the same groups listed above as $R^{4o}$ and $R^{41}$. In particular, preferred are phenoxy, 2-fluorophenoxy, 3-fluorophenoxy, and 4-fluorophenoxy because they provide a compound with a low LUMO energy susceptible to electrochemical reduction.

The silyl sulfonic acid ester compound represented by the formula (27) is preferably a silyl sulfonic acid ester compound represented by the formula (28) because it is chemically stable and shows a low LUMO energy.

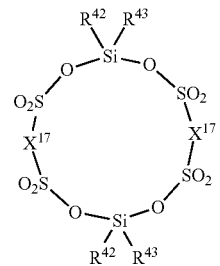

(28)

In the formula (28), $R^{42}$ and $R^{43}$ each independently represent a substituted or unsubstituted C1-C3 alkyl group. $X^{17}$ represents a substituted or unsubstituted C1-C2 alkylene group.

In the formula (28), examples of the C1-C3 alkyl group represented by $R^{42}$ or $R^{43}$ include methyl, ethyl, n-propyl, and isopropyl. In particular, methyl is preferred.

The alkyl group represented by $R^{42}$ or $R^{43}$ is a substituted alkyl group, the alkyl group preferably has a halogen atom and more preferably has a fluorine atom as a substituent.

In the formula (28), examples of the C1-C2 alkylene group represented by $X^{17}$ include methylene and ethylene. In particular, methylene is preferred.

Further, in cases where the alkylene group represented by $X^{17}$ is a substituted alkylene group, the alkylene group preferably has a halogen atom or a substituted or unsubstituted phenyl group.

In the formula (28), in cases where the alkylene group represented by $X^{17}$ has a substituted or unsubstituted phenyl group as a substituent, examples of the substituted or unsubstituted phenyl group include the same groups listed above as $R^{40}$ and $R^{41}$. In particular, preferred are phenyl, 2-fluorophenyl, 3-fluorophenyl, and 4-fluorophenyl because they provide a compound with a low LUMO energy susceptible to electrochemical reduction.

The silyl sulfonic acid ester compound represented by the formula (27) is produced, for example, by reacting a metal salt of a disulfonic acid with a silyl halide compound.

Specifically, in the formula (27), the silyl sulfonic acid ester compound in which $R^{40}$ is methyl, $R^{41}$ is methyl, and $X^{16}$ is methylene is produced by adding a silver salt of methanedisulfonic acid to dichlorodimethylsilane and reacting them with stirring.

The disulfonyl compound according to the present invention has a LUMO (lowest unoccupied molecular orbital) energy of not less than −3.0 eV and not more than 0.4 eV. If the LUMO energy is less than −3.0 eV, the compound is excessively decomposed and a film that shows high resistance may be formed on an electrode. If the LUMO energy is more than 0.4 eV, a stable SEI cannot be formed on the surface of an electrode of non-aqueous electrolyte solution secondary cells or the like. The LUMO energy is preferably not less than −2.0 eV and not more than 0.3 eV and more preferably not less than −1.5 eV and not more than 0.0 eV.

The "LUMO (lowest unoccupied molecular orbital) energy" is calculated by combination of semi-empirical molecular orbital calculation (PM3) and density-functional theory calculation (B3LYP). In the present invention, specifically, the LUMO energy is calculated by Gaussian 03 (Revision B.03, software produced by Gaussian, Inc.).

The disulfonyl compound according to the present invention has a standard enthalpy of formation (H) of not less than −220 kcal/mol and not more than −40 kcal/mol. If the standard enthalpy of formation is less than −220 kcal/mol, the disulfonyl compound may exist in a non-aqueous electrolyte solution in a less stable state. If the standard enthalpy of formation is more than −40 kcal/mol, the compound added to a non-aqueous electrolyte solution and used for an electrical storage device may be less susceptible to electrochemical reduction decomposition. The standard enthalpy of formation is preferably not less than −200 kcal/mol and preferably not more than −50 kcal/mol, and more preferably not less than −180 kcal/mol and more preferably not more than −60 kcal/mol.

The "standard enthalpy of formation" is calculated based on semi-empirical molecular orbital calculation (PM3). Specifically, in the present invention, the standard enthalpy of formation is calculated by MOPAC calculation software (molecular orbital calculation software), MOPAC 97, produced by FUJITSU, in CS Chem3D (R) Version 4.0 produced by Cambridge Soft Corporation.

The disulfonyl compound according to the present invention has an enthalpy change (ΔH) with hydrolysis reaction of not less than −5 kcal/mol and not more than 5 kcal/mol. If the enthalpy change with hydrolysis reaction is less than −5 kcal/mol, the compound becomes less stable against moisture to be possibly easily hydrolized. If the enthalpy change with hydrolysis reaction is more than 5 kcal/mol, the stability of the compound against moisture is increased, but the compound added to a non-aqueous electrolyte solution and used for an electrical storage device may be less susceptible to electrochemical reduction decomposition. The enthalpy change with hydrolysis reaction is preferably not less than −4.5 kcal/mol and preferably not more than 3.0 kcal/mol, and more preferably not less than −4.0 kcal/mol and not more than 1.5 kcal/mol.

The "enthalpy change with hydrolysis reaction" is represented by the following formula, and is calculated by combination of semi-empirical molecular orbital calculation (PM3) and density-functional theory calculation (B3PW91). Specifically, in the present invention, the enthalpy change with hydrolysis reaction is calculated using Gaussian 03 (Revision B.03, software produced by Gaussian, Inc.).
"Enthalpy change (ΔH) with hydrolysis reaction"="Enthalpy of products after hydrolysis"−"Enthalpy of reactants before hydrolysis"

The disulfonyl compound according to the present invention shows a low LUMO energy so that the compound is susceptible to electrochemical reduction. Therefore, when added to a non-aqueous electrolyte solution and used for electrical storage devices such as non-aqueous electrolyte solution secondary cells, the additive for a non-aqueous electrolyte solution of the present invention formed from the compound forms a stable SEI on the surface of an electrode to improve cell performance such as a cycle performance, a discharge/charge capacity, and internal resistance. Further, the disulfonyl compound according to the present invention is stable to moisture and temperature change. Therefore, the additive for a non-aqueous electrolyte solution of the present invention formed from such a compound can be stored at room temperature for a long time. Accordingly, a non-aqueous electrolyte solution containing the additive for a non-aqueous electrolyte solution can also be stored and used for a long time.

Another aspect of the present invention is a non-aqueous electrolyte solution containing an additive for a non-aqueous electrolyte solution of the present invention, a non-aqueous solvent, and an electrolyte.

The amount of the additive for a non-aqueous electrolyte solution of the present invention in the non-aqueous electrolyte solution of the present invention (that is, the amount of the disulfonyl compound according to the present invention) is not particularly limited, and preferably not less than 0.005% by mass and not more than 10% by mass. If the amount of the additive for a non-aqueous electrolyte solution of the present invention is less than 0.005% by mass, the additive may not sufficiently form a stable SEI by electrochemical reduction on the surface of an electrode when used for non-aqueous electrolyte solution secondary cells or the like. If the amount of the additive for a non-aqueous electrolyte solution of the present invention is more than 10% by mass, the additive is less soluble and makes the non-aqueous electrolyte solution more viscous to prevent securing of sufficient ion mobility. As a result, the conductivity of an electrolyte solution may not be sufficiently secured, which may cause a problem in discharge/charge characteristics of electrical storage devices such as non-aqueous electrolyte solution secondary cells. The amount of the additive for a non-aqueous electrolyte solution of the present invention is more preferably not less than 0.01% by mass. The additive for a non-aqueous electrolyte solution of the present invention may be used alone or two or more of these may be used in combination. When two or more of the compounds are used, the total amount of the compounds is preferably not less than 0.005% by mass and preferably not more than 10% by mass.

Further, general additives such as vinylene carbonate (VC), fluoroethylene carbonate (FEC), and 1,3-propane sultone (PS) may optionally be added to the non-aqueous electrolyte solution together with the additive for a non-aqueous electrolyte solution.

The non-aqueous solvent is preferably an aprotic solvent because it can provide a low viscous non-aqueous electrolyte solution. The low viscous non-aqueous electrolyte solution preferably contains at least one selected from the group consisting of cyclic carbonates, chain carbonates, aliphatic carboxylic acid esters, lactones, lactams, cyclic ethers, chain ethers, sulfones, and halogen derivatives thereof. In particular, cyclic carbonates and chain carbonates are preferably used.

Examples of the cyclic carbonate include ethylene carbonate, propylene carbonate, and butylene carbonate.

Examples of the chain carbonate include dimethyl carbonate, diethyl carbonate, and ethyl methyl carbonate.

Examples of the aliphatic carboxylic acid ester include methyl acetate, ethyl acetate, methyl propionate, ethyl propionate, methyl butyrate, methyl isobutyrate, and methyl trimethylacetate.

Examples of the lactone include γ-butyrolactone.

Examples of the lactam include ε-caprolactam and N-methylpyrrolidone.

Examples of the cyclic ether include tetrahydrofuran, 2-methyltetrahydrofuran, tetrahydropyran, and 1,3-dioxolan.

Examples of the chain ether include 1,2-diethoxyethane and ethoxymethoxyethane.

Examples of the sulfone include sulfolane.

Examples of the halogen derivatives include 4-fluoro-1,3-dioxolan-2-one, 4-chloro-1,3-dioxolan-2-one, and 4,5-difluoro-1,3-dioxolan-2-one.

These non-aqueous solvents may be used alone or two or more of these may be used in combination.

These non-aqueous solvents are preferably used, for example, for non-aqueous electrolyte solution secondary cells such as lithium-ion batteries or electric double layer capacitors such as lithium ion capacitors.

The electrolyte is preferably a lithium salt as a source of lithium ions. Specifically, the lithium salt is preferably at least one selected from the group consisting of $LiAlCl_4$, $LiBF_4$, $LiPF_6$, $LiClO_4$, $LiAsF_6$, and $LiSbF_6$. $LiBF_4$ and $LiPF_6$ are more preferred because they have high degree of dissociation to increase the ion conductivity of the electrolyte solution and they also have oxidation-reduction resistance to suppress degradation of a performance of electrical storage device after long-term use. Such electrolytes may be used alone or two or more of these may be used in combination. When the $LiBF_4$ or $LiPF_6$ is used, a mixture of at least one cyclic carbonate and at least one chain carbonate is preferably prepared as a non-aqueous solvent, and a mixture of ethylene carbonate and diethyl carbonate is preferred.

The concentration of the electrolyte in the non-aqueous electrolyte solution of the present invention is not particularly limited, and is preferably not less than 0.1 mol/L and preferably not more than 2.0 mol/L. If the concentration of the electrolyte is less than 0.1 mol/L, the conductivity of the non-aqueous electrolyte solution or the like is not sufficiently secured, which may cause a problem in discharge/charge characteristics of the electrical storage devices such as non-aqueous electrolyte solution secondary cells. If the concentration of the electrolyte is more than 2.0 mol/L, the viscosity increases not to sufficiently secure the ion mobility, and the conductivity or the like of the non-aqueous electrolyte solution cannot be sufficiently secured, which may cause a problem in discharge/charge characteristics of the electrical storage devices such as non-aqueous electrolyte solution secondary cells. The concentration of the electrolyte is more preferably not less than 0.5 mol/L and more preferably not more than 1.5 mol/L.

Another aspect of the present invention is an electrical storage device including the non-aqueous electrolyte solution of the present invention, a cathode, and an anode. Examples of the electrical storage device include non-aqueous electrolyte solution secondary cells and electric double layer capacitors. In particular, lithium-ion batteries and lithium ion capacitors are preferred.

FIG. 1 is a cross section schematically showing an example of the non-aqueous electrolyte solution secondary cell according to the electrical storage device of the present invention.

In FIG. 1, the non-aqueous electrolyte solution secondary cell 1 includes a cathode plate 4 in which a cathode active material layer 3 is disposed on one surface of a cathode current collector 2, and an anode plate 7 in which an anode active material layer 6 is disposed on one surface of an anode current collector 5. The cathode plate 4 and the anode plate 7 are disposed facing each other, and the non-aqueous electrolyte solution 8 of the present invention and a separator 9 in the non-aqueous electrolyte solution 8 are disposed between the plates 4 and 7.

In the non-aqueous electrolyte solution secondary cell according to the electrical storage device of the present invention, the cathode current collector 2 and the anode current collector 5 are, for example, foil made of aluminum, copper, nickel, stainless steel, or the like.

In the non-aqueous electrolyte solution secondary cell according to the electrical storage device of the present invention, a cathode active material for the cathode active material layer 3 is preferably a lithium-containing composite oxide. Examples of the lithium-containing composite oxide include $LiMnO_2$, $LiFeO_2$, $LiCoO_2$, $LiMn_2O_4$, $Li_2FeSiO_4$, $LiNi_{1/3}CO_{1/3}Mn_{1/3}O_2$, and $LiFePO_4$.

In the non-aqueous electrolyte solution secondary cell according to the electrical storage device of the present invention, an anode active material for the anode active material layer 6 may be, for example, materials capable of intercalating/deintercalating lithium ions. Examples of the materials include carbon materials such as graphite and amorphous carbon and oxide materials such as indium oxide, silicon oxide, tin oxide, zinc oxide, and oxide lithium.

The anode active material may be a lithium metal or a metal material capable of forming an alloy with lithium. Examples of the metal capable of forming an alloy with lithium include Cu, Sn, Si, Co, Mn, Fe, Sb, and Ag. A binary alloy and a ternary alloy including these metals and lithium may be used.

These anode active materials may be used alone or two or more of these may be used in combination.

In the non-aqueous electrolyte solution secondary cell according to the electrical storage device of the present invention, the separator 9 may be formed from a porous film that is made of, for example, polyethylene, polypropylene, and a fluorine resin.

Advantageous Effects of Invention

The present invention can provide an additive for a non-aqueous electrolyte solution with excellent storage stability capable of forming a stable SEI on the surface of an electrode to improve cell performance such as a cycle performance, a discharge/charge capacity, and internal resistance, when used for an electrical storage device such as a non-aqueous electrolyte solution secondary cell and electric double layer capacitor. The present invention can also provide a non-aqueous electrolyte solution containing the additive for a non-aqueous electrolyte solution and an electrical storage device using the non-aqueous electrolyte solution.

BRIEF DESCRIPTION OF DRAWINGS

FIG. 1 is a cross section schematically showing an example of the non-aqueous electrolyte solution secondary cell according to the electrical storage device of the present invention.

DESCRIPTION OF EMBODIMENTS

The present invention will be described in more detail below based on examples. The present invention is not limited to those examples.

EXAMPLE 1

Preparation of methanedisulfonic acid bis(phenylamide) (compound 1)

A 200-mL four-necked flask equipped with a stirrer, a condenser, a thermometer, and a dropping funnel was charged with N-phenyl amine (10.2 g) (0.11 mol) and 1,2-dimethoxyethane (70.0 g), and a solution of methanedisulfonyl chloride (10.7 g) (0.05 mol) dissolved in 1,2-dimethoxyethane (20.0 g) was added dropwise thereto over 20 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bis(phenylamide) (5.0 g) (0.015 mol). The yield of the methanedisulfonic acid bis(phenylamide) was 30.4% based on the amount of the methanedisulfonyl chloride.

The resulting methanedisulfonic acid bis(phenylamide) was identified by its properties described below.

$^1$H-nuclear magnetic resonance spectrum (solvent: $CDCl_3$) δ (ppm): 7.62 (s, 2H), 7.28-7.45 (m, 10H), 4.28 (s, 2H)

EXAMPLE 2

Preparation of methanedisulfonic acid bis(methyl phenyl amide) (compound 2)

A 200-mL four-necked flask equipped with a stirrer, a condenser, a thermometer, and a dropping funnel was charged with N,N-methylphenyl amine (11.8 g) (0.11 mol) and 1,2-dimethoxyethane (70.0 g), and a solution of methanedisulfonyl chloride (10.7 g) (0.05 mol) dissolved in 1,2-dimethoxyethane (20.0 g) was added dropwise thereto over 20 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bis(methyl phenyl amide) (11.1 g) (0.031 mol). The yield of the methanedisulfonic acid bis(methyl phenyl amide) was 62.5% based on the amount of the methanedisulfonyl chloride.

The resulting methanedisulfonic acid bis(methyl phenyl amide) was identified by its properties described below.

$^1$H-nuclear magnetic resonance spectrum (solvent: $CDCl_3$) δ (ppm): 7.30-7.41 (m, 10H), 4.32 (s, 2H), 3.46 (s, 6H)

EXAMPLE 3

Preparation of methanedisulfonic acid bis(benzyl methyl amide) (compound 3)

A 200-mL four-necked flask equipped with a stirrer, a condenser, a thermometer, and a dropping funnel was charged with N,N-benzylmethylamine (13.3 g) (0.11 mol) and 1,2-dimethoxyethane (70.0 g), and a solution of methanedisulfonyl chloride (10.7 g) (0.05 mol) dissolved in 1,2-dimethoxyethane (20.0 g) was added dropwise thereto over 20 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and the solvent was removed from the organic phase by reduced pressure distillation at 25° C. Subsequently, toluene (40.0 g) was added, followed by dropwise addition of methanol (10.0 g), whereby crystals were obtained. The crystals were filtered and dried to give methanedisulfonic acid bis(benzyl methyl amide) (2.5 g) (0.007 mol). The yield of the methanedisulfonic acid bis(benzyl methyl amide) was 13.1% based on the amount of the methanedisulfonyl chloride.

The resulting methanedisulfonic acid bis(benzyl methyl amide) was identified by its properties described below.

$^1$H-nuclear magnetic resonance spectrum (solvent: $CD_3CN$) δ (ppm): 7.33-7.44 (m, 10H), 4.66 (s, 2H), 4.41 (s, 4H), 2.82 (s, 6H)

EXAMPLE 4

Preparation of methanedisulfonic acid bis(dibenzylamide (compound 4)

A 200-mL four-necked flask equipped with a stirrer, a condenser, a thermometer, and a dropping funnel was charged with N,N-dibenzylamine (21.7 g) (0.11 mol) and 1,2-dimethoxyethane (70.0 g), and a solution of methanedisulfonyl chloride (10.7 g) (0.05 mol) dissolved in 1,2-dimethoxyethane (20.0 g) was added dropwise thereto over 50 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added dropwise over 50 minutes, followed by stirring over night at the same temperature.

After the completion of the reaction, the reaction solution was filtered, and toluene (100.0 g) and water (50.0 g) were added to the filtrate. Then, an organic phase was separated from the aqueous phase, and the solvent was removed from the organic phase by reduced pressure distillation at 25° C. Subsequently, methanol (35.0 g) was added, whereby crystals were obtained. The crystals were filtered and dried to give methanedisulfonic acid bis(dibenzylamide) (10.2 g) (0.019 mol). The yield of the methanedisulfonic acid bis(dibenzylamide) was 38.2% based on the amount of the methanedisulfonyl chloride.

The resulting methanedisulfonic acid bis(dibenzylamide) was identified by its properties described below.

$^1$H-nuclear magnetic resonance spectrum (solvent: $CDCl_3$) δ (ppm): 7.27-7.33 (m, 20H), 4.40 (s, 8H), 4.15 (s, 2H)

EXAMPLE 5

Preparation of methanedisulfonic acid bis(4-fluoro phenyl amide) (compound 5)

A 200-mL four-necked flask equipped with a stirrer, a condenser, a thermometer, and a dropping funnel was charged with N-(4-fluorophenyl)amine (12.2 g) (0.11 mol) and 1,2-dimethoxyethane (70.0 g), and a solution of methanedisulfonyl chloride (10.7 g) (0.05 mol) dissolved in 1,2-dimethoxyethane (20.0 g) was added dropwise thereto over 20 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added dropwise over 11 hours, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bis(4-fluoro phenyl amide) (9.6 g) (0.027 mol). The yield of the methanedisulfonic acid bis(4-fluoro phenyl amide) was 53.0% based on the amount of the methanedisulfonyl chloride.

The resulting methanedisulfonic acid bis(4-fluoro phenyl amide) was identified by its properties described below.

$^1$H-nuclear magnetic resonance spectrum (solvent: $CDCl_3$) δ (ppm): 7.34-7.39 (m, 4H), 7.26 (s, 2H), 7.08-7.14 (m, 4H), 4.21 (s, 2H)

EXAMPLE 6

Preparation of methanedisulfonic acid bis(2-fluoro phenyl amide) (compound 6)

A 200-mL four-necked flask equipped with a stirrer, a condenser, a thermometer, and a dropping funnel was charged with N-(2-fluorophenyl)amine (12.2 g) (0.11 mol) and 1,2-dimethoxyethane (70.0 g), and a solution of methanedisulfonyl chloride (10.7 g) (0.05 mol) dissolved in 1,2-dimethoxyethane (20.0 g) was added dropwise thereto over 20 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bis(2-fluoro phenyl amide) (4.6 g) (0.013 mol). The yield of the methanedisulfonic acid bis(2-fluoro phenyl amide) was 25.4% based on the amount of the methanedisulfonyl chloride.

The resulting methanedisulfonic acid bis(2-fluoro phenyl amide) was identified by its properties described below.

$^1$H-nuclear magnetic resonance spectrum (solvent: $CDCl_3$) δ (ppm): 7.52-7.58 (m, 2H), 7.49 (d, 2H), 7.14-7.28 (m, 6H), 4.51 (s, 2H)

EXAMPLE 7

Preparation of methanedisulfonic acid bis(4-fluorobenzyl amide) (compound 7)

A 200-mL four-necked flask equipped with a stirrer, a condenser, a thermometer, and a dropping funnel was charged with N-(4-fluorobenzyl)amine (13.8 g) (0.11 mol) and 1,2-dimethoxyethane (70.0 g), and a solution of methanedisulfonyl chloride (10.7 g) (0.05 mol) dissolved in 1,2-dimethoxyethane (20.0 g) was added dropwise thereto over 20 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added over 1 hour, followed by stirring over night at the same temperature.

After the completion of the reaction, the reaction solution was filtered, and to the resulting filtrate were added toluene (150.0 g), water (80.0 g), and 1,2-dimethoxyethane (70.0 g). Then, an organic phase was separated from the aqueous phase, and part of the solvent was removed from the organic phase by reduced pressure distillation at 25° C., whereby crystals were obtained. The crystals were filtered and dried to give methanedisulfonic acid bis(4-fluorobenzyl amide) (5.6 g) (0.014 mol). The yield of the methanedisulfonic acid bis(4-fluorobenzyl amide) was 28.7% based on the amount of the methanedisulfonyl chloride.

The resulting methanedisulfonic acid bis(4-fluorobenzyl amide) was identified by its properties described below.

$^1$H-nuclear magnetic resonance spectrum (solvent: Acetone-$D_6$) δ (ppm): 7.43-7.50 (m, 4H), 7.20-7.27 (m, 4H), 6.9 (s, 2H), 4.79 (s, 2H), 4.39 (d, 4H)

EXAMPLE 8

Preparation of 1,1-ethanedisulfonic acid bis(methyl phenyl amide) (compound 8)

A 200-mL four-necked flask equipped with a stirrer, a condenser, a thermometer, and a dropping funnel was charged with N,N-methylphenyl amine (11.8 g) (0.11 mol) and 1,2-dimethoxyethane (70.0 g), and a solution of 1,1-ethane disulfonyl chloride (11.4 g) (0.05 mol) dissolved in 1,2-dimethoxyethane (20.0 g) was added dropwise thereto over 20 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give 1,1-ethanedisulfonic acid bis (methyl phenyl amide) (4.6 g) (0.013 mol). The yield of the 1,1-ethanedisulfonic acid bis(methyl phenyl amide) was 25.1% based on the amount of the 1,1-ethane disulfonyl chloride.

The resulting 1,1-ethanedisulfonic acid bis(methyl phenyl amide) was identified by its properties described below.

$^1$H-nuclear magnetic resonance spectrum (solvent: $CDCl_3$) δ (ppm): 7.30-7.41 (m, 10H), 4.68 (q, 1H), 2.75 (s, 6H), 1.72 (d, 3H)

EXAMPLE 9

Preparation of 1,1-ethanedisulfonic acid bis(benzyl methyl amide) (compound 9)

A 200-mL four-necked flask equipped with a stirrer, a condenser, a thermometer, and a dropping funnel was charged with N,N-benzylmethylamine (13.3 g) (0.11 mol)

and 1,2-dimethoxyethane (70.0 g), and a solution of 1,1-ethane disulfonyl chloride (11.4 g) (0.05 mol) dissolved in 1,2-dimethoxyethane (20.0 g) was added dropwise thereto over 20 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give 1,1-ethanedisulfonic acid bis(benzyl methyl amide) (5.4 g) (0.014 mol). The yield of the 1,1-ethanedisulfonic acid bis(benzyl methyl amide) was 27.0% based on the amount of the 1,1-ethane disulfonyl chloride.

The resulting 1,1-ethanedisulfonic acid bis(benzyl methyl amide) was identified by its properties described below.

$^1$H-nuclear magnetic resonance spectrum (solvent: $CDCl_3$) δ (ppm): 7.06-7.14 (m, 10H), 4.67 (q, 1H), 3.81 (s, 4H), 2.69 (s, 6H), 1.70 (d, 3H)

EXAMPLE 10

Preparation of 1,2-ethanedisulfonic acid bis(methyl phenyl amide) (compound 10)

A 200-mL four-necked flask equipped with a stirrer, a condenser, a thermometer, and a dropping funnel was charged with N,N-methylphenyl amine (11.8 g) (0.11 mol) and 1,2-dimethoxyethane (70.0 g), and a solution of 1,2-ethane disulfonyl chloride (11.4 g) (0.05 mol) dissolved in 1,2-dimethoxyethane (20.0 g) was added dropwise thereto over 20 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give 1,2-ethanedisulfonic acid bis(methyl phenyl amide) (6.0 g) (0.016 mol). The yield of the 1,2-ethanedisulfonic acid bis(methyl phenyl amide) was 32.3% based on the amount of the 1,2-ethane disulfonyl chloride.

The resulting 1,2-ethanedisulfonic acid bis(methyl phenyl amide) was identified by its properties described below.

$^1$H-nuclear magnetic resonance spectrum (solvent: $CDCl_3$) δ (ppm): 7.19-7.26 (m, 10H), 3.97 (d, 4H), 2.80 (s, 6H)

EXAMPLE 11

Preparation of 2-oxopropane-1,1-disulfonic acid bis(methyl phenyl amide) (compound 11)

A 200-mL four-necked flask equipped with a stirrer, a condenser, a thermometer, and a dropping funnel was charged with methanedisulfonic acid bis(methyl phenyl amide) (17.9 g) (0.05 mol) prepared by the same manner as in Example 2 and dichloromethane (70.0 g), and 60% by mass sodium hydride (2.2 g) (0.055 mol) was added thereto at 0° C. The contents were allowed to stand for 1 hour. Subsequently, while maintaining the temperature at 0° C., to the contents were added dropwise triethylamine (10.6 g) (0.10 mol) and a solution of acetyl chloride (0.5 g) (0.06 mol) dissolved in dichloromethane (20.0 g) over 1 hour, followed by stirring over night at the same temperature.

After the completion of the reaction, the reaction solution was filtered, and dichloromethane (50.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give 2-oxopropane-1,1-disulfonic acid bis(methyl phenyl amide) (3.9 g) (0.010 mol). The yield of the 2-oxopropane-1,1-disulfonic acid bis(methyl phenyl amide) was 19.5% based on the amount of the methanedisulfonic acid bis(methyl phenyl amide).

The resulting 2-oxopropane-1,1-disulfonic acid bis(methyl phenyl amide) was identified by its properties described below.

$^1$H-nuclear magnetic resonance spectrum (solvent: $CDCl_3$) δ (ppm): 6.89-7.27 (m, 10H), 5.35 (s, 1H), 2.81 (s, 6H), 2.09 (s, 3H)

EXAMPLE 12

Preparation of α,α-bis((methylphenylamino)sulfonyl)acetophenone (compound 12)

A 200-mL four-necked flask equipped with a stirrer, a condenser, a thermometer, and a dropping funnel was charged with methanedisulfonic acid bis(methyl phenyl amide) (17.9 g) (0.05 mol) prepared by the same manner as in Example 2 and dichloromethane (70.0 g), and 60% by mass sodium hydride (2.2 g) (0.055 mol) was added at 0° C. The contents were allowed to stand for 1 hour. Subsequently, while maintaining the temperature at 0° C., to the contents were added dropwise triethylamine (10.6 g) (0.10 mol) and a solution of benzoyl chloride (8.4 g) (0.06 mol) dissolved in dichloromethane (20.0 g) over 1 hour, followed by stirring over night at the same temperature.

After the completion of the reaction, the reaction solution was filtered, and dichloromethane (50.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give α,α-bis(methylphenylamino sulfonyl)acetophenone (6.0 g) (0.013 mol). The yield of the α,α-bis(methylphenylamino sulfonyl)acetophenone was 26.3% based on the amount of the methanedisulfonic acid bis(methyl phenyl amide).

The resulting (α,α-bis((methylphenylamino)sulfonyl)acetophenone was identified by its properties described below.

$^1$H-nuclear magnetic resonance spectrum (solvent: $CDCl_3$) δ (ppm): 6.84-7.86 (m, 15H), 6.10 (s, 1H), 2.79 (s, 6H)

EXAMPLE 13

Preparation of 2,2-bis((methylphenylamino)sulfonyl)acetonitrile (compound 13)

To a 200-mL four-necked flask equipped with a stirrer, a condenser, a thermometer, and a dropping funnel was added dropwise chlorosulfonic acid (23.3 g) (0.2 mol) mixed with phosphoryl chloride (46 g) over 1 hour, followed by dropwise addition of cyanoacetic acid (0.85 g) (0.1 mol) over 1 hour. The contents were heated to 100° C. over 2 hours, and stirred for 20 hours at the same temperature. Then, normal pressure distillation was carried out to remove phosphoryl chloride, and reduced pressure distillation was carried out to prepare cyano methanedisulfonyl chloride (14.2 g).

Next, a 200-mL four-necked flask equipped with a stirrer, a condenser, a thermometer, and a dropping funnel was charged with N,N-methylphenyl amine (11.8 g) (0.11 mol) and 1,2-dimethoxyethane (70.0 g), and a solution of cyano methanedisulfonyl chloride (11.9 g) (0.05 mol) dissolved in 1,2-dimethoxyethane (20.0 g) was added dropwise over 20 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give 2,2-bis(methylphenylamino sulfonyl)acetonitrile (5.4 g) (0.014 mol). The yield of the 2,2-bis(methylphenylamino sulfonyl)acetonitrile was 28.5% based on the amount of the cyano methanedisulfonyl chloride.

The resulting 2,2-bis((methylphenylamino)sulfonyl)acetonitrile was identified by its properties described below.

$^1$H-nuclear magnetic resonance spectrum (solvent: CDCl$_3$) δ (ppm): 6.93-7.24 (m, 10H), 5.50 (s, 1H), 2.78 (s, 6H)

EXAMPLE 14

Preparation of bis((methylphenylamino)sulfonyl)nitromethane (compound 14)

To a 200-mL four-necked flask equipped with a stirrer, a condenser, a thermometer, and a dropping funnel was added dropwise chlorosulfonic acid (23.3 g) (0.2 mol) mixed with phosphoryl chloride (46 g) over 1 hour, followed by dropwise addition of nitro-acetic acid (10.5 g) (0.1 mol) over 1 hour. The contents were heated to 100° C. over 2 hours, and stirred for 20 hours at the same temperature. Then, normal pressure distillation was carried out to remove phosphoryl chloride, and reduced pressure distillation was carried out to prepare nitro methanedisulfonyl chloride (15.5 g).

Next, a 200-mL four-necked flask equipped with a stirrer, a condenser, a thermometer, and a dropping funnel was charged with N,N-methylphenyl amine (11.8 g) (0.11 mol) and 1,2-dimethoxyethane (70.0 g), and a solution of nitro methanedisulfonyl chloride (12.9 g) (0.05 mol) dissolved in 1,2-dimethoxyethane (20.0 g) was added dropwise thereto over 20 minutes while maintaining the temperature at 0° C. Subsequently, while maintaining the temperature at 0° C., a solution of triethylamine (10.6 g) (0.10 mol) dissolved in 1,2-dimethoxyethane (20.0 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give bis(methylphenylamino sulfonyl) nitromethane (5.1 g) (0.013 mol). The yield of the bis (methylphenylamino sulfonyl)nitromethane was 25.4% based on the amount of the nitro methanedisulfonyl chloride.

The resulting bis((methylphenylamino)sulfonyl)nitromethane was identified by its properties described below.

$^1$H-nuclear magnetic resonance spectrum (solvent: CDCl$_3$) δ (ppm): 6.88-7.15 (m, 10H), 5.89 (s, 1H), 2.77 (s, 6H)

EXAMPLE 15

Preparation of trimethyl bis((methylphenylamino)sulfonyl)methylsilane (compound 15)

A 200-mL four-necked flask equipped with a stirrer, a condenser, a thermometer, and a dropping funnel was charged with methanedisulfonic acid bis(methyl phenyl amide) (17.9 g) (0.05 mol) prepared by the same manner as in Example 2 and dichloromethane (70.0 g), and 60% by mass sodium hydride (2.2 g) (0.055 mol) was added thereto at 0° C. The contents were allowed to stand for 1 hour. Subsequently, while maintaining the temperature at 0° C., to the contents were added dropwise triethylamine (10.6 g) (0.10 mol) and a solution of trimethyl silyl chloride (6.5 g) (0.06 mol) dissolved in dichloromethane (20.0 g) over 1 hour, followed by stirring over night at the same temperature.

After the completion of the reaction, the reaction solution was filtered, and dichloromethane (50.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give trimethyl bis(methylphenylamino sulfonyl)methylsilane (4.5 g) (0.011 mol). The yield of the trimethyl bis(methylphenylamino sulfonyl) methylsilane was 20.1% based on the amount of the methanedisulfonic acid bis(methyl phenyl amide).

The resulting trimethyl bis((methylphenylamino)sulfonyl)methylsilane was identified by its properties described below.

$^1$H-nuclear magnetic resonance spectrum (solvent: CDCl$_3$) δ (ppm): 6.99-7.27 (m, 10H), 5.85 (s, 1H), 2.74 (s, 6H), 0.00 (s, 9H)

COMPARATIVE EXAMPLE 1

Preparation of methanedisulfonic acid bis(ethylamide) (compound 16)

A 200-mL four-necked flask equipped with a stirrer, a condenser, a thermometer, and a dropping funnel was charged with ethyl amine (5.0 g) (0.11 mol) and 1,2-dimethoxyethane (70.0 g), and a solution of methanedisulfonyl chloride (10.7 g) (0.05 mol) dissolved in 1,2-dimethoxyethane (20.0 g) was added dropwise over 20 minutes while maintaining the temperature at 0° C. Subsequently, while maintaining the temperature at 0° C., triethylamine (10.6 g) (0.10 mol) mixed with 1,2-dimethoxyethane (20.0 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the resulting organic phase by reduced pressure distillation at 25° C., whereby crystals were obtained. The crystals were filtered and dried to give methanedisulfonic acid bis(ethylamide) (2.5 g) (0.011 mol). The yield of the methanedisulfonic acid bis(ethylamide) was 21.4% based on the amount of the methanedisulfonyl chloride.

COMPARATIVE EXAMPLE 2

Preparation of methanedisulfonic acid bis(n-propylamide) (compound 17)

Comparative Example 2 was performed in the same manner as in Comparative Example 1 except that n-propyl amine (6.5 g) (0.11 mol) was used instead of ethyl amine (5.0 g) (0.11 mol). Thus, methanedisulfonic acid bis(n-propylamide) (4.3 g) (0.017 mol, yield of 33.4%) was obtained.

COMPARATIVE EXAMPLE 3

Preparation of methanedisulfonic acid bis(isopropylamide) (compound 18)

Comparative Example 3 was performed in the same manner as in Comparative Example 1 except that diisopropyl amine (11.1 g) (0.11 mol) was used instead of ethyl amine (5.0 g) (0.11 mol). Thus, methanedisulfonic acid bis(isopropylamide) (5.1 g) (0.015 mol, yield of 30.0%) was obtained.

COMPARATIVE EXAMPLE 4

Preparation of methanedisulfonic acid bis(n-butyramide) (compound 19)

Comparative Example 4 was performed in the same manner as in Comparative Example 1 except that n-butyl amine (8.0 g) (0.11 mol) was used instead of ethyl amine (5.0 g) (0.11 mol). Thus, methanedisulfonic acid bis(n-butyramide) (4.2 g) (0.015 mol, yield of 29.1%) was obtained.

COMPARATIVE EXAMPLE 5

Fluoroethylene carbonate (FEC), which is commonly used as an additive for lithium-ion batteries and the like, was prepared as an additive for a non-aqueous electrolyte solution.

<Evaluation>
(LUMO energy, standard enthalpy of formation (H), enthalpy change ($\Delta H$) with hydrolysis reaction)

The LUMO (lowest unoccupied molecular orbital) energies of the compounds 1 to 15 obtained in Examples 1 to 15, respectively, and the compounds 16 to 19 obtained in Comparative Examples 1 to 4, respectively, were derived using the Gaussian 03 software. The results are shown in Tables 1 and 2.

Further, the standard enthalpies of formation (H) of the compounds 1 to 15 obtained in Examples 1 to 15, respectively, and the compounds 16 to 19 obtained in Comparative Examples 1 to 4, respectively, were derived using the MOPAC 97 software. The results are shown in Tables 1 and 2.

Further, the enthalpy changes ($\Delta H$) with hydrolysis reaction of the compounds 1 to 15 obtained in Examples 1 to 15, respectively, and the compounds 16 to 19 obtained in Comparative Examples 1 to 4, respectively, were derived using the Gaussian 03 software. The results are shown in Tables 1 and 2.

TABLE 1

| Cpd. | Structure | LUMO energy (eV) | H (kcal/mol) | $\Delta H$ (kcal/mol) |
|---|---|---|---|---|
| 1 | 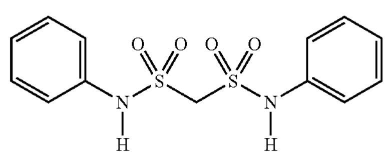 [SMILES: O=S(=O)(CS(=O)(=O)Nc1ccccc1)Nc1ccccc1] | −0.62 | −74.6 | −4.7 |
| 2 | 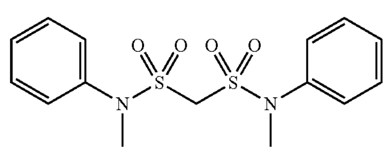 [SMILES: CN(c1ccccc1)S(=O)(=O)CS(=O)(=O)N(C)c1ccccc1] | −0.63 | −56.2 | −3.0 |
| 3 | 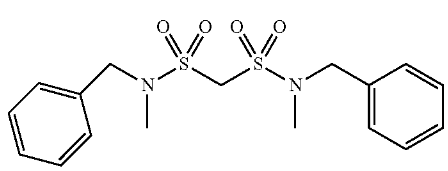 [SMILES: CN(Cc1ccccc1)S(=O)(=O)CS(=O)(=O)N(C)Cc1ccccc1] | −0.47 | −90.6 | −1.7 |

TABLE 1-continued

| Cpd. | Structure | LUMO energy (eV) | H (kcal/mol) | ⊿H (kcal/mol) |
|---|---|---|---|---|
| 4 | 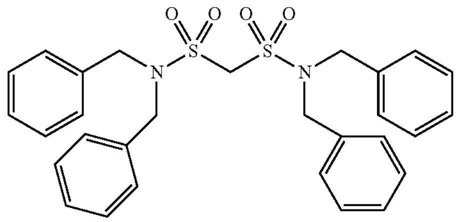 [SMILES: O=S(=O)(CS(=O)(=O)N(Cc1ccccc1)Cc1ccccc1)N(Cc1ccccc1)Cc1ccccc1] | −0.65 | −59.3 | −2.5 |
| 5 | 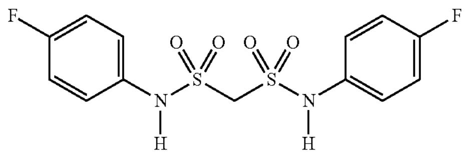 [SMILES: O=S(=O)(CS(=O)(=O)Nc1ccc(F)cc1)Nc1ccc(F)cc1] | −0.71 | −75.6 | −4.3 |
| 6 | 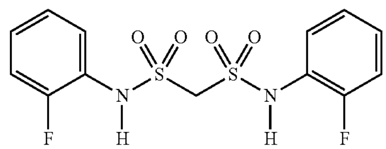 [SMILES: O=S(=O)(CS(=O)(=O)Nc1ccccc1F)Nc1ccccc1F] | −0.76 | −68.3 | −4.5 |
| 7 | 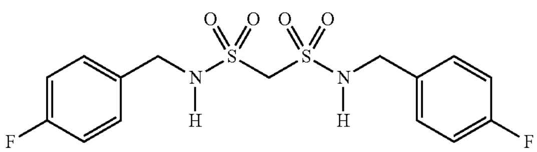 [SMILES: O=S(=O)(CS(=O)(=O)NCc1ccc(F)cc1)NCc1ccc(F)cc1] | −0.50 | −95.3 | −3.6 |
| 8 | 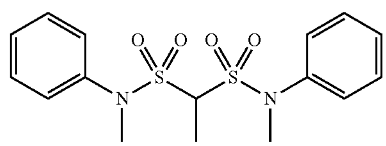 [SMILES: CC(S(=O)(=O)N(C)c1ccccc1)S(=O)(=O)N(C)c1ccccc1] | −0.73 | −58.3 | −2.3 |
| 9 | 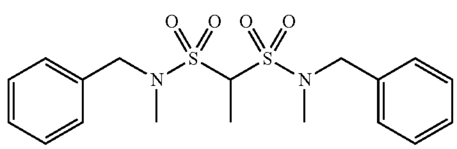 [SMILES: CC(S(=O)(=O)N(C)Cc1ccccc1)S(=O)(=O)N(C)Cc1ccccc1] | −0.45 | −62.3 | −2.0 |
| 10 | 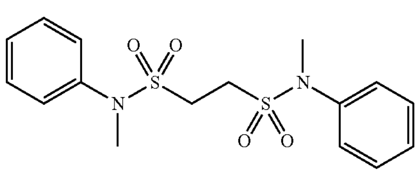 [SMILES: CN(c1ccccc1)S(=O)(=O)CCS(=O)(=O)N(C)c1ccccc1] | −0.61 | −90.4 | −2.6 |
| 11 | 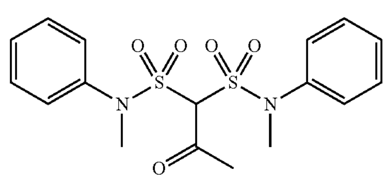 [SMILES: CC(=O)C(S(=O)(=O)N(C)c1ccccc1)S(=O)(=O)N(C)c1ccccc1] | −1.51 | −78.6 | −2.1 |
| 12 | 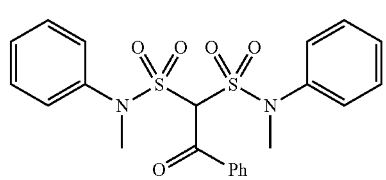 [SMILES: CN(c1ccccc1)S(=O)(=O)C(C(=O)c1ccccc1)S(=O)(=O)N(C)c1ccccc1] | −2.34 | −86.3 | −3.8 |

TABLE 1-continued

| Cpd. | Structure | LUMO energy (eV) | H (kcal/mol) | ΔH (kcal/mol) |
|---|---|---|---|---|
| 13 | (PhN(Me)SO₂-CH(CN)-SO₂N(Me)Ph) | −1.12 | −98.1 | −2.5 |
| 14 | (PhN(Me)SO₂-CH(NO₂)-SO₂N(Me)Ph) | −2.84 | −85.7 | −3.4 |
| 15 | (PhN(Me)SO₂-CH(SiMe₃)-SO₂N(Me)Ph) | −0.70 | −102.8 | −4.1 |

TABLE 2

| Cpd. | Structure | LUMO energy (eV) | H (kcal/mol) | ΔH (kcal/mol) |
|---|---|---|---|---|
| 16 | Et-NH-SO₂-CH₂-SO₂-NH-Et | 0.61 | −154.7 | −3.0 |
| 17 | n-Pr-NH-SO₂-CH₂-SO₂-NH-n-Pr | 0.63 | −170.2 | −2.7 |
| 18 | i-Pr-N(i-Pr)-SO₂-CH₂-SO₂-N(i-Pr)-i-Pr | 0.48 | −178.9 | −3.4 |
| 19 | n-Bu-NH-SO₂-CH₂-SO₂-NH-n-Bu | 0.62 | −176.3 | −2.4 |

Table 1 shows that the disulfonic acid amide compounds (compounds 1 to 15) represented by the formula (3) have a negative LUMO energy of about −0.45 eV to about −2.84 eV, and these disulfonic acid amide compounds according to the additive for a non-aqueous electrolyte solution of the present invention have a low LUMO energy. Therefore, in cases where the compounds 1 to 15 are used as an additive for a non-aqueous electrolyte solution for electrical storage devices such as non-aqueous electrolyte solution secondary cells, the compounds 1 to 15 are electrochemically reduced prior to electrochemical reduction of solvents of non-aqueous electrolyte solutions (for example, cyclic carbonate and chain carbonate: LUMO energy of about 1.2 eV) and an SEI is formed on an electrode, whereby decomposition of solvent molecules in an electrolyte solution can be suppressed. As a result, a high resistant film produced by decomposition of the solvent is less likely to be formed on an electrode to probably improve cell performance.

On the other hand, Table 2 shows that the disulfonic acid amide compounds (compounds 16 to 19) other than the disulfonic acid amide compounds represented by the formula (3) have a high LUMO energy of about 0.48 eV to about 0.63 eV. Therefore, the compounds 16 to 19 are relatively stable to electrochemical reduction and an SEI is less likely to be formed on an electrode.

Table 1 shows that the disulfonic acid amide compounds (compounds 1 to 15) represented by the formula (3) have a standard enthalpy of formation (H) of about −56.2 kcal/mol to about −102.8 kcal/mol. That is, the compounds 1 to 15 according to the present invention have excellent storage stability in a non-aqueous electrolyte solution. Further, in cases where such a non-aqueous electrolyte solution is used for electrical storage devices such as secondary batteries, the compounds subjected to electrochemical reduction decomposition enables formation of an SEI on the surface of an electrode. As a result, decomposition of solvent molecules in an electrolyte solution can be suppressed.

Table 1 further shows that the disulfonic acid amide compounds (compounds 1 to 15) represented by the formula (3) have an enthalpy change (ΔH) with hydrolysis reaction of about −1.7 kcal/mol to about −4.7 kcal/mol. That is, the compounds 1 to 15 according to the present invention are also stable to moisture. Further, in cases where such a non-aqueous electrolyte solution is used for electrical storage devices such as secondary batteries, the compounds subjected to electrochemical reduction decomposition enables formation of an SEI on an electrode. As a result, decomposition of solvent molecules in an electrolyte solution can be suppressed.

Thus, the disulfonic acid amide compounds represented by the formula (3) according to the additive for a non-aqueous electrolyte solution of the present invention have a sufficiently low LUMO energy, excellent storage stability when contained in a non-aqueous electrolyte solution as an additive for a non-aqueous electrolyte solution, and excellent stability to moisture. This shows that such compounds are effective as a novel additive for a non-aqueous electrolyte solution capable of forming a stable SEI on an electrode of electrical storage devices such as non-aqueous electrolyte solution secondary cells.

(Evaluation of Stability)

The compounds 1 to 15 obtained in Examples 1 to 15, respectively, the compounds 16 to 19 obtained in Comparative Examples 1 to 4, respectively, and fluoroethylene carbonate (FEC) of Comparative Example 5 were subjected to a storage test for 90 days under constant temperature and humidity conditions of a temperature of 40±2° C. and humidity of 75±5%. The degradability of each compound was measured with $^1$H-nuclear magnetic resonance spectrum ($^1$H-NMR) and evaluated. Table 3 shows the results.
Good: There is no change in peaks in $^1$H-NMR before and after storage.
Fair: There is a slight change in peaks in $^1$H-NMR before and after storage.
Poor: There is an obvious change in peaks in $^1$H-NMR before and after storage.

TABLE 3

| | Additive | Stability |
|---|---|---|
| Example 1 | Compound 1 | Good |
| Example 2 | Compound 2 | Good |
| Example 3 | Compound 3 | Good |
| Example 4 | Compound 4 | Good |
| Example 5 | Compound 5 | Good |
| Example 6 | Compound 6 | Good |
| Example 7 | Compound 7 | Good |
| Example 8 | Compound 8 | Good |
| Example 9 | Compound 9 | Good |
| Example 10 | Compound 10 | Good |
| Example 11 | Compound 11 | Good |
| Example 12 | Compound 12 | Good |
| Example 13 | Compound 13 | Good |
| Example 14 | Compound 14 | Good |
| Example 15 | Compound 15 | Good |
| Comparative Example 1 | Compound 16 | Fair |
| Comparative Example 2 | Compound 17 | Fair |
| Comparative Example 3 | Compound 18 | Fair |
| Comparative Example 4 | Compound 19 | Fair |
| Comparative Example 5 | FEC | Poor |

As shown in Table 3, fluoroethylene carbonate (FEC) of Comparative Example 5 is partly hydrolyzed and has poor stability. On the other hand, little change is observed in the disulfonic acid amide compounds obtained in Examples 1 to 15 and such compounds have excellent stability.

(Measurement of LSV (Linear Sweep Voltammetry))

Ethylene carbonate (EC) and diethyl carbonate (DEC) were mixed in a volume ratio of EC:DEC=30:70 to prepare a non-aqueous solvent mixture. $LiPF_6$ was dissolved as an electrolyte in the mixture so as to prepare a 1.0 mol/L $LiPF_6$ solution, and a compound of each of the examples and comparative examples was added thereto as an additive for a non-aqueous electrolyte solution in an amount of 1.0% by mass of the total weight of the solution containing the non-aqueous solvent mixture and the electrolyte. Thus, a non-aqueous electrolyte solution was prepared. Polarization was measured in a potential scanning rate of 5 mV/sec using the resulting non-aqueous electrolyte solution, a disk electrode made from glassy carbon as an electrode, and platinum as a counter electrode. A reduction starting voltage was calculated using a silver electrode as a reference electrode, in which the potential with respect to the reference electrode when 100 μA of current flows was defined as oxidation potential and the potential with respect to the reference electrode when −100 μA of current flows was defined as reduction potential. Further, as Reference Example 1, a reduction starting voltage was similarly calculated using a non-aqueous electrolyte solution prepared without adding an additive for a non-aqueous electrolyte solution. Table 4 shows the results.

TABLE 4

| | Electrolyte | Solvent | Additive | LSV Reduction starting voltage (V) |
|---|---|---|---|---|
| Example 1 | $LiPF_6$ 1.0 mol/L | EC/DEC (30/70) vol % | Compound 1 1.0% by mass | −3.2 |
| Example 2 | $LiPF_6$ 1.0 mol/L | EC/DEC (30/70) vol % | Compound 2 1.0% by mass | −3.1 |
| Example 3 | $LiPF_6$ 1.0 mol/L | EC/DEC (30/70) vol % | Compound 3 1.0% by mass | −3.2 |
| Example 4 | $LiPF_6$ 1.0 mol/L | EC/DEC (30/70) vol % | Compound 4 1.0% by mass | −3.0 |
| Example 5 | $LiPF_6$ 1.0 mol/L | EC/DEC (30/70) vol % | Compound 5 1.0% by mass | −2.7 |
| Example 6 | $LiPF_6$ 1.0 mol/L | EC/DEC (30/70) vol % | Compound 6 1.0% by mass | −2.9 |
| Example 7 | $LiPF_6$ 1.0 mol/L | EC/DEC (30/70) vol % | Compound 7 1.0% by mass | −2.8 |
| Example 8 | $LiPF_6$ 1.0 mol/L | EC/DEC (30/70) vol % | Compound 8 1.0% by mass | −2.8 |
| Example 9 | $LiPF_6$ 1.0 mol/L | EC/DEC (30/70) vol % | Compound 9 1.0% by mass | −2.9 |
| Example 10 | $LiPF_6$ 1.0 mol/L | EC/DEC (30/70) vol % | Compound 10 1.0% by mass | −2.8 |
| Example 11 | $LiPF_6$ 1.0 mol/L | EC/DEC (30/70) vol % | Compound 11 1.0% by mass | −2.7 |
| Example 12 | $LiPF_6$ 1.0 mol/L | EC/DEC (30/70) vol % | Compound 12 1.0% by mass | −2.7 |
| Example 13 | $LiPF_6$ 1.0 mol/L | EC/DEC (30/70) vol % | Compound 13 1.0% by mass | −2.9 |
| Example 14 | $LiPF_6$ 1.0 mol/L | EC/DEC (30/70) vol % | Compound 14 1.0% by mass | −3.0 |
| Example 15 | $LiPF_6$ 1.0 mol/L | EC/DEC (30/70) vol % | Compound 15 1.0% by mass | −2.8 |
| Comparative Example 1 | $LiPF_6$ 1.0 mol/L | EC/DEC (30/70) vol % | Compound 16 1.0% by mass | −3.6 |
| Comparative Example 2 | $LiPF_6$ 1.0 mol/L | EC/DEC (30/70) vol % | Compound 17 1.0% by mass | −3.5 |
| Comparative Example 3 | $LiPF_6$ 1.0 mol/L | EC/DEC (30/70) vol % | Compound 18 1.0% by mass | −3.6 |
| Comparative Example 4 | $LiPF_6$ 1.0 mol/L | EC/DEC (30/70) vol % | Compound 19 1.0% by mass | −3.6 |
| Comparative Example 5 | $LiPF_6$ 1.0 mol/L | EC/DEC (30/70) vol % | FEC 1.0% by mass | −3.3 |
| Reference Example 1 | $LiPF_6$ 1.0 mol/L | EC/DEC (30/70) vol % | None | −3.6 |

Table 4 shows that the non-aqueous electrolyte solutions each containing a disulfonic acid amide compound obtained in each of the examples have a higher reduction starting voltage than the non-aqueous electrolyte solutions each containing a compound of each of the comparative examples. Therefore, in cases where a non-aqueous electrolyte solution containing an additive for a non-aqueous electrolyte solution formed from a disulfonic acid amide compound prepared in each of the examples is used for electrical storage devices such as non-aqueous electrolyte solution secondary cells, the disulfonic acid amide compound according to the present invention is electrochemically reduced prior to electrochemical reduction of the non-aqueous electrolyte solution of Reference Example 1 and non-aqueous electrolyte solutions each containing a compound of each of the comparative examples, and a stable SEI is easily formed on the surface of an electrode of electrical storage devices such as non-aqueous electrolyte solution secondary cells.

(Preparation of Cell)

Each of the cathode active materials according to Tables 5 to 8 and a carbon black as a conductivity imparting agent were dry mixed, and the mixture was uniformly dispersed in N-methyl-2-pyrrolidone (NMP) in which polyvinylidene fluoride (PVDF) was dissolved as a binder to prepare a slurry. The resulting slurry was applied to an aluminum foil (square, thickness of 20 μm) that is to be a cathode current collector, and the NMP was dried off to prepare a cathode sheet. The resulting cathode sheet had a solid mass ratio of cathode active material:conductivity imparting agent: PVDF=80:10:10.

On the other hand, a commercially available graphite-coated electrode sheet (produced by Hohsen Corp.) was used as an anode sheet.

Ethylene carbonate (EC) and diethyl carbonate (DEC) were mixed in a volume ratio of EC:DEC=30:70 to prepare a non-aqueous solvent mixture. $LiPF_6$ as an electrolyte was dissolved in the mixture so as to prepare a 1.0 mol/L $LiPF_6$ solution. A compound of each of the examples and comparative examples was added thereto as an additive for a non-aqueous electrolyte solution in an amount of 1.0% by mass of the total weight of the solution containing the non-aqueous solvent mixture and the electrolyte. Thus, a non-aqueous electrolyte solution was prepared.

A cylindrical secondary battery was prepared in such a way that an anode sheet and a cathode sheet were laminated and a polyethylene separator was disposed between the sheets in the resulting non-aqueous electrolyte solution. Further, as Reference Example 1, a cylindrical secondary battery was similarly prepared using a non-aqueous electrolyte solution prepared without adding an additive for a non-aqueous electrolyte solution.

(Evaluation of Cycle Performance)

The resulting cylindrical secondary batteries were subjected to a charge/discharge cycle test under the conditions of a temperature of 25° C., a charging rate of 0.3 C, a discharging rate of 0.3 C, a charge termination voltage of 4.2 V, and a discharge termination voltage of 2.5 V. Tables 5 to 8 show discharge capacity retentions (%) after 200 cycles.

The "discharge capacity retention (%) after 200 cycles" was determined by dividing the discharge capacity (mAh) after 200 cycles of the cycle test by the discharge capacity (mAh) after 10 cycles of the cycle test and multiplying the resulting value by 100.

TABLE 5

| | Cathode active material | Additive | Discharge capacity retention (%) |
|---|---|---|---|
| Example 1 | $LiMn_2O_4$ | Compound 1 | 90 |
| Example 2 | $LiMn_2O_4$ | Compound 2 | 91 |
| Example 3 | $LiMn_2O_4$ | Compound 3 | 92 |
| Example 4 | $LiMn_2O_4$ | Compound 4 | 91 |
| Example 5 | $LiMn_2O_4$ | Compound 5 | 90 |
| Example 6 | $LiMn_2O_4$ | Compound 6 | 90 |
| Example 7 | $LiMn_2O_4$ | Compound 7 | 90 |
| Example 8 | $LiMn_2O_4$ | Compound 8 | 92 |
| Example 9 | $LiMn_2O_4$ | Compound 9 | 92 |
| Example 10 | $LiMn_2O_4$ | Compound 10 | 91 |
| Example 11 | $LiMn_2O_4$ | Compound 11 | 90 |
| Example 12 | $LiMn_2O_4$ | Compound 12 | 93 |
| Example 13 | $LiMn_2O_4$ | Compound 13 | 90 |
| Example 14 | $LiMn_2O_4$ | Compound 14 | 93 |

TABLE 5-continued

| | Cathode active material | Additive | Discharge capacity retention (%) |
|---|---|---|---|
| Example 15 | $LiMn_2O_4$ | Compound 15 | 91 |
| Comparative Example 1 | $LiMn_2O_4$ | Compound 16 | 78 |
| Comparative Example 2 | $LiMn_2O_4$ | Compound 17 | 77 |
| Comparative Example 3 | $LiMn_2O_4$ | Compound 18 | 80 |
| Comparative Example 4 | $LiMn_2O_4$ | Compound 19 | 76 |
| Comparative Example 5 | $LiMn_2O_4$ | FEC | 82 |
| Reference Example 1 | $LiMn_2O_4$ | None | 74 |

TABLE 6

| | Cathode active material | Additive | Discharge capacity retention (%) |
|---|---|---|---|
| Example 1 | $LiCoO_2$ | Compound 1 | 91 |
| Example 2 | $LiCoO_2$ | Compound 2 | 92 |
| Example 3 | $LiCoO_2$ | Compound 3 | 92 |
| Example 4 | $LiCoO_2$ | Compound 4 | 93 |
| Example 5 | $LiCoO_2$ | Compound 5 | 88 |
| Example 6 | $LiCoO_2$ | Compound 6 | 90 |
| Example 7 | $LiCoO_2$ | Compound 7 | 89 |
| Example 8 | $LiCoO_2$ | Compound 8 | 90 |
| Example 9 | $LiCoO_2$ | Compound 9 | 92 |
| Example 10 | $LiCoO_2$ | Compound 10 | 92 |
| Example 11 | $LiCoO_2$ | Compound 11 | 94 |
| Example 12 | $LiCoO_2$ | Compound 12 | 90 |
| Example 13 | $LiCoO_2$ | Compound 13 | 88 |
| Example 14 | $LiCoO_2$ | Compound 14 | 94 |
| Example 15 | $LiCoO_2$ | Compound 15 | 89 |
| Comparative Example 1 | $LiCoO_2$ | Compound 16 | 73 |
| Comparative Example 2 | $LiCoO_2$ | Compound 17 | 74 |
| Comparative Example 3 | $LiCoO_2$ | Compound 18 | 79 |
| Comparative Example 4 | $LiCoO_2$ | Compound 19 | 73 |
| Comparative Example 5 | $LiCoO_2$ | FEC | 81 |
| Reference Example 1 | LiCoO2 | None | 71 |

TABLE 7

| | Cathode active material | Additive | Discharge capacity retention (%) |
|---|---|---|---|
| Example 1 | $LiNi_{1/3}Co_{1/3}Mn_{1/3}O_2$ | Compound 1 | 90 |
| Example 2 | $LiNi_{1/3}Co_{1/3}Mn_{1/3}O_2$ | Compound 2 | 92 |
| Example 3 | $LiNi_{1/3}Co_{1/3}Mn_{1/3}O_2$ | Compound 3 | 91 |
| Example 4 | $LiNi_{1/3}Co_{1/3}Mn_{1/3}O_2$ | Compound 4 | 91 |
| Example 5 | $LiNi_{1/3}Co_{1/3}Mn_{1/3}O_2$ | Compound 5 | 89 |
| Example 6 | $LiNi_{1/3}Co_{1/3}Mn_{1/3}O_2$ | Compound 6 | 90 |
| Example 7 | $LiNi_{1/3}Co_{1/3}Mn_{1/3}O_2$ | Compound 7 | 88 |
| Example 8 | $LiNi_{1/3}Co_{1/3}Mn_{1/3}O_2$ | Compound 8 | 89 |
| Example 9 | $LiNi_{1/3}Co_{1/3}Mn_{1/3}O_2$ | Compound 9 | 91 |
| Example 10 | $LiNi_{1/3}Co_{1/3}Mn_{1/3}O_2$ | Compound 10 | 92 |
| Example 11 | $LiNi_{1/3}Co_{1/3}Mn_{1/3}O_2$ | Compound 11 | 93 |
| Example 12 | $LiNi_{1/3}Co_{1/3}Mn_{1/3}O_2$ | Compound 12 | 92 |
| Example 13 | $LiNi_{1/3}Co_{1/3}Mn_{1/3}O_2$ | Compound 13 | 91 |
| Example 14 | $LiNi_{1/3}Co_{1/3}Mn_{1/3}O_2$ | Compound 14 | 90 |
| Example 15 | $LiNi_{1/3}Co_{1/3}Mn_{1/3}O_2$ | Compound 15 | 88 |
| Comparative Example 1 | $LiNi_{1/3}Co_{1/3}Mn_{1/3}O_2$ | Compound 16 | 69 |
| Comparative Example 2 | $LiNi_{1/3}Co_{1/3}Mn_{1/3}O_2$ | Compound 17 | 67 |

TABLE 7-continued

| | Cathode active material | Additive | Discharge capacity retention (%) |
|---|---|---|---|
| Comparative Example 3 | LiNi$_{1/3}$Co$_{1/3}$Mn$_{1/3}$O$_2$ | Compound 18 | 77 |
| Comparative Example 4 | LiNi$_{1/3}$Co$_{1/3}$Mn$_{1/3}$O$_2$ | Compound 19 | 69 |
| Comparative Example 5 | LiNi$_{1/3}$Co$_{1/3}$Mn$_{1/3}$O$_2$ | FEC | 80 |
| Reference Example 1 | LiNi$_{1/3}$Co$_{1/3}$Mn$_{1/3}$O$_2$ | None | 65 |

TABLE 8

| | Cathode active material | Additive | Discharge capacity retention (%) |
|---|---|---|---|
| Example 1 | LiFePO$_4$ | Compound 1 | 90 |
| Example 2 | LiFePO$_4$ | Compound 2 | 91 |
| Example 3 | LiFePO$_4$ | Compound 3 | 92 |
| Example 4 | LiFePO$_4$ | Compound 4 | 92 |
| Example 5 | LiFePO$_4$ | Compound 5 | 91 |
| Example 6 | LiFePO$_4$ | Compound 6 | 91 |
| Example 7 | LiFePO$_4$ | Compound 7 | 90 |
| Example 8 | LiFePO$_4$ | Compound 8 | 91 |
| Example 9 | LiFePO$_4$ | Compound 9 | 92 |
| Example 10 | LiFePO$_4$ | Compound 10 | 90 |
| Example 11 | LiFePO$_4$ | Compound 11 | 95 |
| Example 12 | LiFePO$_4$ | Compound 12 | 92 |
| Example 13 | LiFePO$_4$ | Compound 13 | 93 |
| Example 14 | LiFePO$_4$ | Compound 14 | 92 |
| Example 15 | LiFePO$_4$ | Compound 15 | 90 |
| Comparative Example 1 | LiFePO$_4$ | Compound 16 | 78 |
| Comparative Example 2 | LiFePO$_4$ | Compound 17 | 80 |
| Comparative Example 3 | LiFePO$_4$ | Compound 18 | 86 |
| Comparative Example 4 | LiFePO$_4$ | Compound 19 | 79 |
| Comparative Example 5 | LiFePO$_4$ | FEC | 83 |
| Reference Example 1 | LiFePO$_4$ | None | 78 |

Tables 5 to 8 show that the cylindrical secondary batteries each using a non-aqueous electrolyte solution containing a disulfonic acid amide compound prepared in each of Examples 1 to 15 have a higher discharge capacity retention in a cycle test than the cylindrical secondary batteries each using the non-aqueous electrolyte solution of Reference Example 1 or a non-aqueous electrolyte solution containing a compound of each of the comparative examples. Therefore, in electrical storage devices such as non-aqueous electrolyte solution secondary cells, the non-aqueous electrolyte solutions each containing an additive for a non-aqueous electrolyte solution formed from a disulfonic acid amide compound obtained in each of the examples provide an SEI with higher stability to charge/discharge cycle on the surface of an electrode than the non-aqueous electrolyte solution of Reference Example 1 and the non-aqueous electrolyte solutions each containing a compound of each of the comparative examples.

EXAMPLE 16

Preparation of 2,5-Diphenyl-[1,6,2,5]dithiadiazepane 1,1,6,6-tetraoxide (compound 20: cyclic cisulfonic acid amide compound represented by the formula (12))

A 300-mL four-necked flask equipped with a stirrer, a condenser, a thermometer, and a dropping funnel was charged with N,N'-diphenylethylenediamine (4.25 g) (0.020 mol) and dichloromethane (120.0 g), and methanedisulfonyl chloride (4.26 g) (0.020 mol) mixed with dichloromethane (40.0 g) was added dropwise over 1 hour while maintaining the temperature at 0° C. Subsequently, while maintaining the temperature at 0° C., a solution of triethylamine (4.5 g) (0.044 mol) dissolved in dichloromethane (40.0 g) was added dropwise over 1 hour, followed by stirring over night at the same temperature.

After the completion of the reaction, the reaction solution was filtered, and toluene (200.0 g) and water (100.0 g) were added to the filtrate. Then, an organic phase was separated from the aqueous phase, and part of the solvent was removed from the organic phase by reduced pressure distillation at 25° C., whereby crystals were obtained. The crystals were filtered and dried. The dried crystals were recrystalized using dichloromethane and heptane, collected by filtration, and dried to give a compound 20 (cyclic disulfonic acid amide compound represented by the formula (12)) (1.8 g) (0.005 mol). The yield of the resulting compound 20 was 25.0% based on the amount of the methanedisulfonyl chloride.

The resulting compound 20 was identified by its properties described below.

$^1$H-nuclear magnetic resonance spectrum (solvent: CDCl$_3$) δ (ppm): 7.63-7.65 (m, 4H), 7.45-7.49 (m, 4H), 7.41-7.42 (m, 2H), 5.20 (s, 2H), 4.18 (s, 4H) LC/MS (m/z [M-H]+): 351

EXAMPLE 17

Preparation of 5,9-Dihydro-6,8-dithia-5,9-diaza-benzocycloheptene 6,6,8,8-tetraoxide (compound 21: cyclic disulfonic acid amide compound represented by the formula (13))

A 500-mL four-necked flask equipped with a stirrer, a condenser, a thermometer, and a dropping funnel was charged with 1,2-dimethoxyethane (140.0 g), and a solution of methanedisulfonyl chloride (21.3 g) (0.10 mol) dissolved in 1,2-dimethoxyethane (80.0 g) and a solution of o-phenylenediamine (11.9 g) (0.11 mol) dissolved in 1,2-dimethoxyethane (80.0 g) were simultaneously added dropwise over 1 hour while maintaining the temperature at −20° C. Subsequently, while maintaining the temperature at −20° C., a solution of triethylamine (21.3 g) (0.21 mol) dissolved in 1,2-dimethoxyethane (50.0 g) was added dropwise over 1 hour, followed by stirring over night at the same temperature.

After the completion of the reaction, the reaction solution was filtered, and toluene (200.0 g) and water (100.0 g) were added to the filtrate. Then, an organic phase was separated from the aqueous phase, and the solvent was removed from the organic phase by reduced pressure distillation at 25° C., whereby crystals were obtained. After repulping with dichloromethane (200.0 g), the crystals were collected by filtration, and dried. The dried crystals were recrystalized with methanol and toluene, collected by filtration, and dried to give a compound 21 (cyclic disulfonic acid amide compound represented by the formula (13)) (4.8 g) (0.019 mol). The yield of the compound 21 was 19.1% based on the amount of the methanedisulfonyl chloride.

The resulting compound 21 was identified by its properties described below.

$^1$H-nuclear magnetic resonance spectrum (solvent: $CD_3CN$) δ (ppm): 8.05 (s, 2H), 7.36-7.37 (m, 2H), 7.26-7.27 (m, 2H), 5.03 (s, 2H) LC/MS (m/z [M-H]+): 247

COMPARATIVE EXAMPLE 6

1,3-propane sultone (PS) (produced by Aldrich) was used as a compound 22.

COMPARATIVE EXAMPLE 7

Preparation of ethylene methanedisulfonate (compound 23)

A compound 23 (ethylene methanedisulfonate) (1.11 g) (0.0055 mol) was prepared in the same manner as in Example 16 except that ethylene glycol (1.24 g) (0.020 mol) was used instead of N,N'-diphenylethylenediamine (4.25 g) (0.020 mol). The yield of the compound 23 was 27.5% based on the amount of the methanedisulfonyl chloride.

COMPARATIVE EXAMPLE 8

Preparation of 2,3-Dimethyl-[1,4,2,3]dithiadiazolidine 1,1,4,4-tetraoxide (compound 24)

A compound 24 (2,3-dimethyl-[1,4,2,3]dithiadiazolidine 1,1,4,4-tetraoxide) (0.88 g) (0.0044 mol) was prepared in the same manner as in Example 16 except that N,N'-dimethylhydrazine (1.20 g) (0.020 mol) was used instead of N,N'-diphenylethylenediamine (4.25 g) (0.020 mol). The yield of the compound 24 was 22.0% based on the amount of the methanedisulfonyl chloride.

<Evaluation>
(LUMO energy, standard enthalpy of formation (H), enthalpy change (ΔH) with hydrolysis reaction)

The LUMO (lowest unoccupied molecular orbital) energies of the compounds 20 to 24 prepared in the examples and comparative examples were derived using the Gaussian 03 software. The results are shown in Table 9.

Further, the standard enthalpies of formation (H) of the compounds 20 to 24 prepared in the examples and comparative examples were derived using the MOPAC 97 software. The results are shown in Table 9.

Further, the enthalpy changes (ΔH) with hydrolysis reaction of the compounds 20 to 24 prepared in the examples and comparative examples were derived using the Gaussian 03 software. The results are shown in Table 9.

TABLE 9

| Structure | LUMO energy (eV) | H (kcal/mol) | ΔH (kcal/mol) |
|---|---|---|---|
| Compound 20 | −0.65 | −56.2 | −4.7 |
| Compound 21 | −1.01 | −129.4 | −2.7 |
| Compound 22 | 0.97 | −120.6 | −2.6 |
| Compound 23 | −0.12 | −233.9 | −5.6 |
| Compound 24 | −0.02 | −79.0 | −6.1 |

Table 9 shows that the cyclic disulfonic acid amide compounds (compounds 20 and 21) represented by the formula (9) have a negative LUMO energy of about −0.65 eV to about −1.01 eV, and these cyclic disulfonic acid amide compounds according to the additive for a non-aqueous electrolyte solution of the present invention have a low LUMO energy. Therefore, in cases where the compounds 20 and 21 are used as an additive for a non-aqueous electrolyte solution in electrical storage devices such as non-aqueous electrolyte solution secondary cells, the compounds 20 and 21 are electrochemically reduced prior to electrochemical reduction of solvents of non-aqueous electrolyte solutions (for example, cyclic carbonate and chain carbonate: LUMO energy of about 1.2 eV), and an SEI is formed on an electrode, whereby decomposition of solvent molecules in an electrolyte solution can be suppressed. As a result, a high resistant film produced by decomposition of the solvent is less likely to be formed on an electrode to probably improve cell performance.

On the other hand, Table 9 shows that commonly used 1,3-propane sultone (PS) (compound 22), ethylene methanedisulfonate (compound 23), and the cyclic disulfonic acid amide compound (compound 24) other than the cyclic disulfonic acid amide compounds represented by the formula (9) has a relatively high LUMO energy of about −0.12 eV to about 0.97 eV. That is, the compounds 22 to 24 are relatively stable to electrochemical reduction, and are less likely to form an SEI on an electrode.

Table 9 shows that the cyclic disulfonic acid amide compounds (compounds 20 and 21) represented by the formula (9) have a standard enthalpy of formation (H) of about −56.2 kcal/mol to about −129.4 kcal/mol. That is, the compounds 20 and 21 according to the present invention have excellent storage stability in a non-aqueous electrolyte solution. Further, in cases where such a non-aqueous electrolyte solution is used for electrical storage devices such as secondary batteries, the compounds subjected to electrochemical reduction decomposition enables formation of an SEI on an electrode. As a result, decomposition of solvent molecules in an electrolyte solution can be suppressed.

Further, Table 9 shows that the cyclic disulfonic acid amide compounds (compounds 20 and 21) represented by the formula (9) have an enthalpy change ($\Delta H$) with hydrolysis reaction of about −2.7 kcal/mol to about −4.7 kcal/mol. That is, the compounds 20 and 21 according to the present invention are also stable to moisture. Further, in cases where such a non-aqueous electrolyte solution is used for electrical storage devices such as secondary batteries, the compounds subjected to electrochemical reduction decomposition enables formation of an SEI on an electrode. As a result, decomposition of solvent molecules in an electrolyte solution can be suppressed.

Thus, the cyclic disulfonic acid amide compounds represented by the formula (9) according to the additive for a non-aqueous electrolyte solution of the present invention have a sufficiently low LUMO energy, excellent storage stability when contained in a non-aqueous electrolyte solution as an additive for a non-aqueous electrolyte solution, and excellent stability to moisture. This shows that such compounds are effective as a novel additive for a non-aqueous electrolyte solution capable of forming a stable SEI on an electrode of electrical storage devices such as non-aqueous electrolyte solution secondary cells.

(Measurement of LSV (linear sweep voltammetry))

Ethylene carbonate (EC) and diethyl carbonate (DEC) were mixed in a volume ratio of EC:DEC=30:70 to prepare a non-aqueous solvent mixture. LiPF$_6$ as an electrolyte was dissolved in the mixture so as to prepare a 1.0 mol/L LiPF$_6$ solution. Each of the compounds 20 to 24 of the examples and comparative examples was added thereto as an additive for a non-aqueous electrolyte solution in an amount of 1.0% by mass of the total weight of the solution containing the non-aqueous solvent mixture and the electrolyte. Thus, a non-aqueous electrolyte solution was prepared. Polarization was measured in a potential scanning rate of 5 mV/sec using the resulting non-aqueous electrolyte solution, a disk electrode made from glassy carbon as an electrode, and platinum as a counter electrode. A reduction starting voltage was calculated using a silver electrode as a reference electrode, in which the potential with respect to the reference electrode when 100 µA of current flows was defined as oxidation potential and the potential with respect to the reference electrode when −100 µA of current flows was defined as reduction potential. Further, as Reference Example 2, a reduction starting voltage was similarly calculated using a non-aqueous electrolyte solution prepared without adding an additive for a non-aqueous electrolyte solution. Table 10 shows the results.

TABLE 10

| | Electrolyte | Solvent | Additive | LSV Reduction starting voltage (V) |
|---|---|---|---|---|
| Example 16 | LiPF$_6$ 1.0 mol/L | EC/DEC (30/70) vol % | Compound 20 1.0% by mass | −2.8 |
| Example 17 | LiPF$_6$ 1.0 mol/L | EC/DEC (30/70) vol % | Compound 21 1.0% by mass | −2.4 |
| Comparative Example 6 | LiPF$_6$ 1.0 mol/L | EC/DEC (30/70) vol % | Compound 22 1.0% by mass | −3.5 |
| Comparative Example 7 | LiPF$_6$ 1.0 mol/L | EC/DEC (30/70) vol % | Compound 23 1.0% by mass | −3.2 |
| Comparative Example 8 | LiPF$_6$ 1.0 mol/L | EC/DEC (30/70) vol % | Compound 24 1.0% by mass | −3.3 |
| Reference Example 2 | LiPF$_6$ 1.0 mol/L | EC/DEC (30/70) vol % | None | −3.6 |

Table 10 shows that the non-aqueous electrolyte solutions each containing a disulfonic acid amide compound of each of the examples have a higher reduction starting voltage than the non-aqueous electrolyte solutions each containing a compound of each of the comparative examples or the non-aqueous electrolyte solution of Reference Example 2. Therefore, in cases where a non-aqueous electrolyte solution containing an additive for a non-aqueous electrolyte solution formed from the cyclic disulfonic acid amide compound obtained in Example 16 or 17 is used, in electrical storage devices such as non-aqueous electrolyte solution secondary cells, the cyclic disulfonic acid amide compound according to the present invention is electrochemically reduced prior to electrochemical reduction of the solvent of the non-aqueous electrolyte solution of Reference Example 2 and the non-aqueous electrolyte solutions each containing a compound of each of Comparative Examples 6 to 8, and easily forms a stable SEI on the surface of an electrode of cells such as non-aqueous electrolyte solution secondary cells.

(Preparation of Cell)

LiMn$_2$O$_4$ as a cathode active material and a carbon black as a conductivity imparting agent were dry mixed, and the mixture was uniformly dispersed in N-methyl-2-pyrrolidone (NMP) in which polyvinylidene fluoride (PVDF) was dissolved as a binder to prepare a slurry. The resulting slurry was applied to an aluminum foil (square, thickness of 20 µm) that is to be a cathode current collector, and the NMP was dried off to prepare a cathode sheet. The resulting cathode sheet had a solid mass ratio of cathode active material:conductivity imparting agent:PVDF=80:10:10.

A commercially available graphite-coated electrode sheet (produced by Hohsen Corp.) was used as an anode sheet.

Ethylene carbonate (EC) and diethyl carbonate (DEC) were mixed in a volume ratio of EC:DEC=30:70 to prepare a non-aqueous solvent mixture. LiPF$_6$ was dissolved as an electrolyte in the mixture so as to prepare a 1.0 mol/L LiPF$_6$ solution, a compound of each of the examples and comparative examples was added thereto as an additive for a non-aqueous electrolyte solution in an amount of 1.0% by mass of the total weight of the solution containing the non-aqueous solvent mixture and the electrolyte. Thus, non-aqueous electrolyte solution was prepared.

A cylindrical secondary battery was prepared in such a way that an anode sheet and a cathode sheet were laminated and a polyethylene separator was disposed between the sheets in the resulting non-aqueous electrolyte solution. Further, as Reference Example 2, a cylindrical secondary battery was similarly prepared using the non-aqueous electrolyte solution prepared without adding an additive for a non-aqueous electrolyte.

(Measurement of Discharge Capacity Retention and Internal Resistance Ratio)

The resulting cylindrical secondary batteries were subjected to a charge/discharge cycle test under the conditions of a temperature of 25° C., a charging rate of 0.3 C, a discharging rate of 0.3 C, a charge termination voltage of 4.2

V, and a discharge termination voltage of 2.5 V. Table 11 shows discharge capacity retention (%) and internal resistance ratio after 200 cycles.

The "discharge capacity retention (%)" after 200 cycles was determined by dividing the discharge capacity (mAh) after 200 cycles of the cycle test by the discharge capacity (mAh) after 10 cycles of the cycle test and multiplying the resulting value by 100. Further, the "internal resistance ratio" after 200 cycles was expressed as a value of the resistance after 200 cycles of the cycle test relative to a value of the resistance before the cycle test taken as 1.

TABLE 11

| | Electrolyte | Solvent | Additive | Discharge capacity retention (%) | Internal resistance ratio |
|---|---|---|---|---|---|
| Example 16 | LiPF$_6$ 1.0 mol/L | EC/DEC (30/70) vol % | Compound 20 1.0% by mass | 90 | 1.18 |
| Example 17 | LiPF$_6$ 1.0 mol/L | EC/DEC (30/70) vol % | Compound 21 1.0% by mass | 92 | 1.21 |
| Comparative Example 6 | LiPF$_6$ 1.0 mol/L | EC/DEC (30/70) vol % | Compound 22 1.0% by mass | 77 | 1.68 |
| Comparative Example7 | LiPF$_6$ 1.0 mol/L | EC/DEC (30/70) vol % | Compound 23 1.0% by mass | 81 | 1.69 |
| Comparative Example 8 | LiPF$_6$ 1.0 mol/L | EC/DEC (30/70) vol % | Compound 24 1.0% by mass | 81 | 1.55 |
| Reference Example 2 | LiPF$_6$ 1.0 mol/L | EC/DEC (30/70)vol % | None | 74 | 1.83 |

Table 11 shows that the cylindrical secondary batteries each using a non-aqueous electrolyte solution containing a cyclic disulfonic acid amide compound prepared in each of the examples have a higher discharge capacity retention in a cycle test than the cylindrical secondary batteries each using a non-aqueous electrolyte solution containing a compound of each of the comparative examples or the non-aqueous electrolyte solution of Reference Example 2. Therefore, in cells such as non-aqueous electrolyte solution secondary cells, the non-aqueous electrolyte solutions containing an additive for a non-aqueous electrolyte solution formed from a cyclic disulfonic acid amide compound obtained in each of Examples 16 and 17 provide an SEI with higher stability to charge/discharge cycle on the surface of an electrode of the cells than the non-aqueous electrolyte solution of Reference Example 2 and the non-aqueous electrolyte solutions each containing a compound of each of Comparative Examples 6 to 8.

Further, the non-aqueous electrolyte solutions each containing a cyclic disulfonic acid amide compound obtained in each of the examples have smaller internal resistance than the non-aqueous electrolyte solution of Reference Example 2 and the non-aqueous electrolyte solutions each containing a compound of each of the comparative examples, and therefore suppress an increase in internal resistance during a cycle test.

EXAMPLE 18

Preparation of phosphorus-containing sulfonic acid amide compound (compound 25) represented by the formula (15) in which R$^{16}$ is ethyl, R$^{17}$ is ethyl, R$^{18}$ is methylene, R$^{19}$ is methylene, X$^9$ is methyl, X$^{10}$ is methyl, and Y$^1$ is hydrogen A 200-mL four-necked flask equipped with a stirrer, a condenser, a thermometer, and a dropping funnel was charged with bromoacetic acid (13.9 g) (0.1 mol) and dimethoxyethane (70.0 g), and triethyl phosphite (16.6 g) (0.1 mol) mixed with dimethoxyethane (20.0 g) was added dropwise over 2 hours at 0° C. The temperature was gradually increased to room temperature. The solution was stirred over night and rinsed with water and a saturated saline. The dimethoxyethane was removed by distillation to give a reaction product (30 g).

Next, a 200-mL four-necked flask equipped with a stirrer, a condenser, a thermometer, and a dropping funnel was charged with phosphoryl chloride (46 g), chlorosulfonic acid (23.3 g) (0.2 mol) was added dropwise over 1 hour, followed by dropwise addition of the resulting reaction product (30 g) over 1 hour. Then, the solution was heated to 100° C. over 2 hours and stirred 20 hours at the same temperature. Then, phosphoryl chloride was removed by normal pressure distillation to give an oily reaction product (25 g).

Next, a 200-mL four-necked flask equipped with a stirrer, a condenser, a thermometer, and a dropping funnel was charged with dimethoxyethane (70 g) and N,N'-diethylmethylenediamine (10.2 g) (0.1 mol), followed by cooling to 0° C. The resulting oily reaction product (25 g) was added dropwise thereto over 2 hours, followed by dropwise addition of triethylamine (30.4 g) (0.3 mol) over 2 hours. The contents were further stirred for 10 hours to complete the reaction. The reaction solution was filtered, and toluene (100 g) and water (25 g) were added to the filtrate. Then, an organic phase was separated from the aqueous phase, and the toluene was removed from the organic phase by reduced pressure distillation. Then, the remaining organic phase was cooled to 0° C. Methanol (40 g) was added dropwise thereto over 3 hours to give crystals. The crystals were filtered and dried under reduced pressure to give a phosphorus-containing sulfonic acid amide compound (compound 25) (5 g) represented by the formula (15) in which R$^{16}$ was ethyl, R$^{17}$ was ethyl, R$^{18}$ was methylene, R$^{19}$ was methylene, X$^9$ was methyl, X$^{10}$ was methyl, and Y$^1$ was hydrogen. The yield of the compound 25 was 14% based on the amount of the bromoacetic acid.

(Preparation of Non-Aqueous Electrolyte Solution)

Ethylene carbonate (EC) and diethyl carbonate (DEC) were mixed in a volume ratio of EC:DEC=30:70 to prepare a non-aqueous solvent mixture. LiPF$_6$ was dissolved as an electrolyte in the mixture so as to prepare a 1.0 mol/L LiPF$_6$ solution. The compound 25 prepared as an additive for a non-aqueous electrolyte solution was added thereto in an amount of 0.5% by mass of the total weight of the solution containing the non-aqueous solvent mixture and the electrolyte. Thus, a non-aqueous electrolyte solution was prepared.

EXAMPLE 19

A non-aqueous electrolyte solution was prepared in the same manner as in Example 18 except that the amount of the compound 25 was 1.0% by mass in "Preparation of non-aqueous electrolyte solution".

EXAMPLE 20

Preparation of phosphorus-containing sulfonic acid amide compound (compound 26) represented by the formula (15) in which $R^{16}$ is ethyl, $R^{17}$ is ethyl, $R^{18}$ and $12^{19}$ are omitted as C0 alkylene, $X^9$ is phenyl, $X^{10}$ is phenyl, and $Y^1$ is hydrogen A 200-mL four-necked flask equipped with a stirrer, a condenser, a thermometer, and a dropping funnel was charged with bromoacetic acid (13.9 g) (0.1 mol) and dimethoxyethane (70.0 g), and triethyl phosphite (16.6 g) (0.1 mol) mixed with dimethoxyethane (20.0 g) was added dropwise over 2 hours at 0° C. The contents were gradually heated to room temperature, stirred over night, and rinsed with water and a saturated saline. The dimethoxyethane was removed by distillation to give a reaction product (30 g).

Next, a 200-mL four-necked flask equipped with a stirrer, a condenser, a thermometer, and a dropping funnel was charged with phosphoryl chloride (46 g), and chlorosulfonic acid (23.3 g) (0.2 mol) was added dropwise over 1 hour, followed by drowpise addition of the resulting reaction product (30 g) over 1 hour. Then, the contents were heated to 100° C. over 2 hours, and stirred for 20 hours at the same temperature. Then, phosphoryl chloride was removed by normal pressure distillation to give an oily reaction product (25 g).

Next, a 200-mL four-necked flask equipped with a stirrer, a condenser, a thermometer, and a dropping funnel was charged with dimethoxyethane (70 g) and methylene dianilide (19.8 g) (0.10 mol), and the contents were cooled to 0° C. The resulting oily reaction product (25 g) was added dropwise over 2 hours, followed by dropwise addition of triethylamine (22.3 g) (0.22 mol) over 2 hours. The contents were stirred for 10 hours to complete the reaction. The reaction solution was filtered, and toluene (100 g) and water (25 g) were added to the filtrate. Then, an organic phase was separated from the aqueous phase, and the toluene was removed from the organic phase by reduced pressure distillation. Then, the remaining organic phase was cooled to 0° C. Methanol (40 g) was added dropwise thereto over 3 hours to give crystals. The crystals were filtered and dried under reduced pressure to give a phosphorus-containing sulfonic acid amide compound (compound 26) (5 g) represented by the formula (15) in which $R^{16}$ was ethyl, $R^{17}$ was ethyl, $R^{18}$ and $R^{19}$ were omitted as C0 alkylene, $X^9$ was phenyl, $X^{10}$ was phenyl, and $Y^1$ was hydrogen. The yield of the compound 26 was 11% based on the amount of the bromoacetic acid.

(Preparation of Non-Aqueous Electrolyte Solution)

Ethylene carbonate (EC) and diethyl carbonate (DEC) were mixed in a volume ratio of EC:DEC=30:70 to prepare a non-aqueous solvent mixture. $LiPF_6$ as an electrolyte was dissolved in the mixture so as to prepare a 1.0 mol/L $LiPF_6$ solution. The compound 26 prepared as an additive for a non-aqueous electrolyte solution was added in an amount of 1.0% by mass of the total weight of the solution containing the non-aqueous solvent mixture and the electrolyte. Thus, a non-aqueous electrolyte solution was prepared.

EXAMPLE 21

Preparation of phosphorus-containing sulfonic acid amide compound (compound 27) represented by the formula (16) in which $R^{16}$ is ethyl, $R^{17}$ is ethyl, $R^{18}$ and $R^{19}$ are omitted as C0 alkylene, $R^{23}$ is methyl, $R^{24}$ is methyl, $X^9$ is phenyl, $X^{10}$ is phenyl, and $Y^1$ is hydrogen A 200-mL four-necked flask equipped with a stirrer, a condenser, a thermometer, and a dropping funnel was charged with bromoacetic acid (13.9 g) (0.1 mol) and dimethoxyethane (70.0 g), and triethyl phosphite (16.6 g) (0.1 mol) mixed with dimethoxyethane (20.0 g) was added dropwise over 2 hours at 0° C. The contents were gradually heated to room temperature, stirred over night, and rinsed with water and a saturated saline. The dimethoxyethane was removed by distillation to give a reaction product (30 g).

Next, a 200-mL four-necked flask equipped with a stirrer, a condenser, a thermometer, and a dropping funnel was charged with phosphoryl chloride (46 g), and chlorosulfonic acid (23.3 g) (0.2 mol) was added dropwise over 1 hour, followed by dropwise addition of the resulting reaction product (30 g) over 1 hour. Then, the contents were heated to 100° C. over 2 hours and stirred for 20 hours at the same temperature. Then, phosphoryl chloride was removed by normal pressure distillation to give an oily reaction product (25 g).

Next, a 200-mL four-necked flask equipped with a stirrer, a condenser, a thermometer, and a dropping funnel was charged with dimethoxyethane (70 g) and methylphenyl amine (21.4 g) (0.20 mol), and the contents were cooled to 0° C. The resulting oily reaction product (25 g) was added dropwise thereto over 2 hours, followed by dropwise addition of triethylamine (22.3 g) (0.22 mol) over 2 hours. Further, the contents were stirred for 10 hours to complete the reaction. The reaction solution was filtered, and toluene (100 g) and water (25 g) were added to the filtrate. Then, an organic phase was separated from the aqueous phase, and the toluene was removed from the organic phase by reduced pressure distillation. Then, the remaining organic phase was cooled to 0° C. Methanol (40 g) was added dropwise thereto over 3 hours to give crystals. The crystals were filtered and dried under reduced pressure to give a phosphorus-containing sulfonic acid amide compound (compound 27) (7 g) represented by the formula (16) in which $R^{16}$ was ethyl, $R^{17}$ was ethyl, $R^{18}$ and $R^{19}$ were omitted as C0 alkylene, $R^{23}$ was methyl, $R^{24}$ was methyl, $X^9$ was phenyl, $X^{10}$ was phenyl, and $Y^1$ was hydrogen. The yield of the compound 27 was 14% based on the amount of the bromoacetic acid.

(Preparation of Non-Aqueous Electrolyte Solution)

Ethylene carbonate (EC) and diethyl carbonate (DEC) were mixed in a volume ratio of EC:DEC=30:70 to prepare a non-aqueous solvent mixture. $LiPF_6$ as an electrolyte was dissolved in the mixture so as to prepare a 1.0 mol/L $LiPF_6$ solution. The compound 27 prepared as an additive for a non-aqueous electrolyte solution was added in an amount of 1.0% by mass of the total weight of the solution containing the non-aqueous solvent mixture and the electrolyte. Thus, a non-aqueous electrolyte solution was prepared.

EXAMPLE 22

Preparation of phosphorus-containing sulfonic acid amide compound (compound 28) represented by the formula (16) in which $R^{16}$ is ethyl, $R^{17}$ is ethyl, $R^{18}$ is methylene, $R^{19}$ is methylene, $R^{23}$ is methyl, $R^{24}$ is methyl, $X^9$ is phenyl, $X^{10}$ is phenyl, and $Y^1$ is hydrogen A phosphorus-containing sulfonic acid amide compound (compound 28) (6 g) represented by the formula (16) in which $R^{16}$ was ethyl, $R^{17}$ was ethyl, $R^{18}$ was methylene, $R^{19}$ was methylene, $R^{23}$ was methyl, $R^{24}$ was methyl, $X^9$ was phenyl, $X^{10}$ was phenyl, and $Y^1$ was hydrogen was prepared in the same manner as in Example 21 except that benzylmethylamine (24.2 g) (0.20 mol) was used instead of methylphenyl amine (21.4 g) (0.20 mol). The yield of the compound 28 was 12% based on the amount of the bromoacetic acid.

(Preparation of Non-Aqueous Electrolyte Solution)

Ethylene carbonate (EC) and diethyl carbonate (DEC) were mixed in a volume ratio of EC:DEC=30:70 to prepare a non-aqueous solvent mixture. $LiPF_6$ as an electrolyte was dissolved in the mixture so as to prepare a 1.0 mol/L $LiPF_6$ solution. The compound 28 prepared as an additive for a non-aqueous electrolyte solution was added in an amount of 1.0% by mass of the total weight of the solution containing the non-aqueous solvent mixture and the electrolyte. Thus, a non-aqueous electrolyte solution was prepared.

COMPARATIVE EXAMPLE 9

A non-aqueous electrolyte solution was prepared in the same manner as in Example 18 except that no compound 25 was used.

COMPARATIVE EXAMPLE 10

A non-aqueous electrolyte solution was prepared in the same manner as in Example 19 except that 1,3-propane sultone (PS) was used instead of the compound 25.

COMPARATIVE EXAMPLE 11

A non-aqueous electrolyte solution was prepared in the same manner as in Example 19 except that vinylene carbonate (VC) was used instead of the compound 25.

COMPARATIVE EXAMPLE 12

A non-aqueous electrolyte solution was prepared in the same manner as in Comparative Example 11 except that the amount of the vinylene carbonate (VC) was 2.0% by mass.

COMPARATIVE EXAMPLE 13

A non-aqueous electrolyte solution was prepared in the same manner as in Example 19 except that fluoroethylene carbonate (FEC) was used instead of the compound 25.

COMPARATIVE EXAMPLE 14

A non-aqueous electrolyte solution was prepared in the same manner as in Comparative Example 13 except that the amount of the fluoroethylene carbonate (FEC) was 2.0% by mass.

<Evaluation>
(LUMO Energy, Standard Enthalpy of Formation (H), Enthalpy Change ($\Delta H$) with Hydrolysis Reaction)

The LUMO (lowest unoccupied molecular orbital) energies of the compounds 25 to 28 prepared in the examples were derived using the Gaussian 03 software. The results are shown in Table 12.

Further, the standard enthalpies of formation (H) of the compounds 25 to 28 prepared in the examples were derived using the MOPAC 97 software. The results are shown in Table 12.

Further, the enthalpy changes ($\Delta H$) with hydrolysis reaction of the compounds 25 to 28 prepared in the examples were derived using the Gaussian 03 software. The results are shown in Table 12.

TABLE 12

| | Structure | LUMO energy (eV) | H (kcal/mol) | $\Delta H$ (kcal/mol) |
|---|---|---|---|---|
| Compound 25 | (Et, Et structure) | -0.14 | -187.9 | -4.3 |
| Compound 26 | (Ph, Ph structure) | -0.86 | -207.6 | -3.9 |
| Compound 27 | (Me/Ph, Me/Ph structure) | -0.75 | -203.4 | -3.7 |
| Compound 28 | (Me/PhCH2, Me/PhCH2 structure) | -0.5 | -188.3 | -4.1 |

Table 12 shows that the phosphorus-containing sulfonic acid amide compounds (compounds 25 to 28) represented by the formula (14) have a negative LUMO energy of about −0.14 eV to about −0.86 eV, and these phosphorus-containing sulfonic acid amide compounds according to the additive for a non-aqueous electrolyte solution of the present invention have a low LUMO energy. Therefore, in cases where the compounds 25 to 28 are used as an additive for a non-aqueous electrolyte solution for electrical storage devices such as non-aqueous electrolyte solution secondary cells, the compounds 25 to 28 are electrochemically reduced prior to electrochemical reduction of solvents of non-aqueous electrolyte solutions (for example, cyclic carbonate and chain carbonate: LUMO energy of about 1.2 eV), and an SEI is formed on an electrode, whereby decomposition of solvent molecules in an electrolyte solution can be suppressed. As a result, a high resistant film produced by decomposition of the solvent is less likely to be formed on an electrode to probably improve cell performance.

Table 12 shows that the phosphorus-containing sulfonic acid amide compounds (compounds 25 to 28) represented by the formula (14) have a standard enthalpy of formation (H) of about −187.9 kcal/mol to about −207.6 kcal/mol. That is, the compounds 25 to 28 according to the present invention have excellent storage stability in a non-aqueous electrolyte solution. Further, in cases where such a non-aqueous electrolyte solution is used for electrical storage devices such as secondary batteries, the compounds subjected to electrochemical reduction decomposition enables formation of an SEI on an electrode.

As a result, decomposition of solvent molecules in an electrolyte solution can be suppressed.

Further, Table 12 shows that the phosphorus-containing sulfonic acid amide compounds (compounds 25 to 28) represented by the formula (14) have an enthalpy change ($\Delta H$) with hydrolysis reaction of about −3.7 kcal/mol to about −4.3 kcal/mol. That is, the compounds 25 to 28 according to the present invention are also stable to moisture. Further, in cases where such a non-aqueous electrolyte solution is used for electrical storage devices such as secondary batteries, the compounds subjected to electrochemical reduction decomposition enables formation of an SEI on the surface of an electrode. As a result, decomposition of solvent molecules in an electrolyte solution can be suppressed.

Thus, the phosphorus-containing sulfonic acid amide compounds represented by the formula (14) according to the additive for a non-aqueous electrolyte solution of the present invention have a sufficiently low LUMO energy, excellent storage stability when contained in a non-aqueous electrolyte solution as an additive for a non-aqueous electrolyte solution, and excellent stability to moisture. This shows that such compounds are effective as a novel additive for a non-aqueous electrolyte solution capable of forming a stable SEI on an electrode of electrical storage devices such as non-aqueous electrolyte solution secondary cells.

(Preparation of Cell)

$LiMn_2O_4$ as a cathode active material and a carbon black as a conductivity imparting agent were dry mixed, and the mixture was uniformly dispersed in N-methyl-2-pyrrolidone (NMP) in which polyvinylidene fluoride (PVDF) was dissolved as a binder to prepare a slurry. The resulting slurry was applied to an aluminum foil (square, thickness of 20 μm) that is to be a cathode current collector, and the NMP was dried off to prepare a cathode sheet. The resulting cathode sheet had a solid mass ratio of cathode active material: conductivity imparting agent:PVDF=80:10:10.

A commercially available graphite-coated electrode sheet (produced by Hohsen Corp.) was used as an anode sheet.

A cylindrical secondary battery was prepared in such a way that an anode sheet and a cathode sheet were laminated and a polyethylene separator was disposed between the sheets in a non-aqueous electrolyte solution prepared in each of the examples and comparative examples.

(Measurement of Discharge Capacity Retention and Internal Resistance Ratio)

The resulting cylindrical secondary batteries were subjected to a charge/discharge cycle test under the conditions of a temperature of 25° C., a charging rate of 0.3 C, a discharging rate of 0.3 C, a charge termination voltage of 4.2 V, and a discharge termination voltage of 2.5 V. Table 13 shows discharge capacity retention (%) and internal resistance ratio after 200 cycles. The "discharge capacity retention (%)" after 200 cycles was determined by dividing the discharge capacity (mAh) after 200 cycles of the cycle test by the discharge capacity (mAh) after 10 cycles of the cycle test and multiplying the resulting value by 100. Further, the "internal resistance ratio" after 200 cycles was expressed a value of the resistance after 200 cycles of the cycle test relative to a value of the resistance before the cycle test taken as 1.

TABLE 13

| | Electrolyte | Solvent | Additive | Discharge capacity retention (%) | Internal resistance ratio |
|---|---|---|---|---|---|
| Example 18 | $LiPF_6$ 1.0 mol/L | EC/DEC (30/70) vol % | Compound 25 0.5% by mass | 91 | 1.36 |
| Example 19 | $LiPF_6$ 1.0 mol/L | EC/DEC (30/70) vol % | Compound 25 1.0% by mass | 96 | 1.25 |
| Example 20 | $LiPF_6$ 1.0 mol/L | EC/DEC (30/70) vol % | Compound 26 1.0% by mass | 97 | 1.22 |
| Example 21 | $LiPF_6$ 1.0 mol/L | EC/DEC (30/70) vol % | Compound 27 1.0% by mass | 96 | 1.26 |
| Example 22 | $LiPF_6$ 1.0 mol/L | EC/DEC (30/70) vol % | Compound 28 1.0% by mass | 97 | 1.24 |
| Comparative Example 9 | $LiPF_6$ 1.0 mol/L | EC/DEC (30/70) vol % | None | 74 | 1.83 |
| Comparative Example 10 | $LiPF_6$ 1.0 mol/L | EC/DEC (30/70) vol % | PS 1.0% by mass | 77 | 1.68 |
| Comparative Example 11 | $LiPF_6$ 1.0 mol/L | EC/DEC (30/70) vol % | VC 1.0% by mass | 83 | 1.69 |
| Comparative Example 12 | $LiPF_6$ 1.0 mol/L | EC/DEC (30/70) vol % | VC 2.0% by mass | 84 | 1.53 |
| Comparative Example 13 | $LiPF_6$ 1.0 mol/L | EC/DEC (30/70) vol % | FEC 1.0% by mass | 81 | 1.66 |
| Comparative Example 14 | $LiPF_6$ 1.0 mol/L | EC/DEC (30/70) vol % | FEC 2.0% by mass | 83 | 1.67 |

Table 13 shows that the cylindrical secondary batteries each using a non-aqueous electrolyte solution containing a phosphorus-containing sulfonic acid amide compound prepared in each of the examples have a higher discharge capacity retention in a cycle test than the cylindrical secondary batteries each using a non-aqueous electrolyte solution of each of the comparative examples. Therefore, in cells such as non-aqueous electrolyte solution secondary cells, the non-aqueous electrolyte solutions each containing an additive for a non-aqueous electrolyte solution formed from a phosphorus-containing sulfonic acid amide compound obtained in each of the examples provide an SEI with higher stability to charge/discharge cycle on the surface of an electrode of the cells than the non-aqueous electrolyte solutions of the comparative examples. Further, the non-aqueous electrolyte solutions each containing a phosphorus-containing sulfonic acid amide compound of each of the examples can keep an internal resistance ratio lower than the non-aqueous electrolyte solutions of the comparative examples, and suppress an increase in internal resistance during a cycle test.

EXAMPLE 23

Preparation of methanedisulfonic acid bispyrrolidine (compound 29)

A 200-mL four-necked flask equipped with a stirrer, a condenser, a thermometer, and a dropping funnel was charged with pyrrolidine (7.3 g) (0.103 mol) and 1,2-dimethoxyethane (100 g), and a solution of methanedisulfonyl chloride (10.0 g) (0.047 mol) dissolved in 1,2-dimethoxyethane (10 g) was added dropwise over 20 minutes while maintaining the temperature at 0° C. Subsequently, while maintaining the temperature at 0° C., a solution of triethylamine (11.4 g) (0.112 mol) dissolved in 1,2-dimethoxyethane (10 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bispyrrolidine (6.0 g) (0.021 mol). The yield of the methanedisulfonic acid bispyrrolidine was 45.2% based on the amount of the methanedisulfonyl chloride.

The resulting methanedisulfonic acid bispyrrolidine was identified by its properties described below.

$^1$H-nuclear magnetic resonance spectrum (solvent: $CDCl_3$) δ (ppm): 1.58 ppm (dt, 8H), 2.80 ppm (t, 8H), 5.55 ppm (s, 2H)

(Preparation of Non-Aqueous Electrolyte Solution)

Ethylene carbonate (EC) and diethyl carbonate (DEC) were mixed in a volume ratio of EC:DEC=30:70 to prepare a non-aqueous solvent mixture. $LiPF_6$ as an electrolyte was dissolved in the mixture so as to prepare a 1.0 mol/L $LiPF_6$ solution. The compound 29 shown in Table 14 as an additive for a non-aqueous electrolyte solution was added to the solution in an amount of 0.5% by mass of the total weight of the solution containing the non-aqueous solvent mixture and the electrolyte. Thus, a non-aqueous electrolyte solution was prepared.

EXAMPLE 24

A non-aqueous electrolyte solution was prepared in the same manner as in Example 23 except that the amount of the compound 29 was 1.0% by mass in "Preparation of non-aqueous electrolyte solution".

EXAMPLE 25

Preparation of methanedisulfonic acid bispiperidine (compound 30)

A 200-mL four-necked flask equipped with a stirrer, a condenser, a thermometer, and a dropping funnel was charged with piperidine (8.8 g) (0.103 mol) and 1,2-dimethoxyethane (100 g), and a solution of methanedisulfonyl chloride (10.0 g) (0.047 mol) dissolved in 1,2-dimethoxyethane (10 g) was added dropwise over 20 minutes while maintaining the temperature at 0° C. Subsequently, while maintaining the temperature at 0° C., a solution of triethylamine (11.4 g) (0.112 mol) dissolved in 1,2-dimethoxyethane (10 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bispiperidine (4.5 g) (0.014 mol). The yield of the methanedisulfonic acid bispiperidine was 30.8% based on the amount of the methanedisulfonyl chloride.

The resulting methanedisulfonic acid bispiperidine was identified by its properties described below.

$^1$H-nuclear magnetic resonance spectrum (solvent: $CDCl_3$) δ (ppm): 1.47 ppm (dt, 8H), 1.51 ppm (dt, 4H), 2.66 ppm (t, 8H), 5.73 ppm (s, 2H)

A non-aqueous electrolyte solution was prepared in the same manner as in Example 23 except that the compound 30 was used in an amount of 1.0% by mass instead of the compound 29 in "Preparation of non-aqueous electrolyte solution".

EXAMPLE 26

Preparation of methanedisulfonic acid bismorpholine (compound 31)

A 200-mL four-necked flask equipped with a stirrer, a condenser, a thermometer, and a dropping funnel was charged with morpholine (9.0 g) (0.103 mol) and 1,2-dimethoxyethane (100 g), and a solution of methanedisulfonyl chloride (10.0 g) (0.047 mol) dissolved in 1,2-dimethoxyethane (10 g) was added dropwise over 20 minutes while maintaining the temperature at 0° C. Subsequently, while maintaining the temperature at 0° C., a solution of triethylamine (11.4 g) (0.112 mol) dissolved in 1,2-dimethoxyethane (10 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bismorpholine (8.6 g) (0.027 mol). The yield of the methanedisulfonic acid bismorpholine was 58.2% based on the amount of the methanedisulfonyl chloride.

The resulting methanedisulfonic acid bismorpholine was identified by its properties described below.

$^1$H-nuclear magnetic resonance spectrum (solvent: CDCl$_3$) δ (ppm): 3.25 (t, 8H), 3.64 (t, 8H), 5.12 (s, 2H)

A non-aqueous electrolyte solution was prepared in the same manner as in Example 23 except that the compound 31 was used in an amount of 1.0% by mass instead of the compound 29 in "Preparation non-aqueous electrolyte solution".

EXAMPLE 27

Preparation of methanedisulfonic acid bisthiomorpholine (compound 32)

A 200-mL four-necked flask equipped with a stirrer, a condenser, a thermometer, and a dropping funnel was charged with thiomorpholine (10.6 g) (0.103 mol) and 1,2-dimethoxyethane (100 g), and a solution of methanedisulfonyl chloride (10.0 g) (0.047 mol) dissolved in 1,2-dimethoxyethane (10 g) was added dropwise over 20 minutes while maintaining the temperature at 0° C. Subsequently, while maintaining the temperature at 0° C., a solution of triethylamine (11.4 g) (0.112 mol) dissolved in 1,2-dimethoxyethane (10 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bisthiomorpholine (5.3 g) (0.015 mol). The yield of the methanedisulfonic acid bisthiomorpholine was 32.5% based on the amount of the methanedisulfonyl chloride.

The resulting methanedisulfonic acid bisthiomorpholine was identified by its properties described below.

$^1$H-nuclear magnetic resonance spectrum (solvent: CDCl$_3$) δ (ppm): 3.33 (t, 8H), 3.66 (t, 8H), 5.13 (s, 2H)

A non-aqueous electrolyte solution was prepared in the same manner as in Example 23 except that the compound 32 was used in an amount of 1.0% by mass instead of the compound 29 in "(Preparation of non-aqueous electrolyte solution)".

EXAMPLE 28

Preparation of methanedisulfonic acid bis(1-methylpiperazine) (compound 33)

A 200-mL four-necked flask equipped with a stirrer, a condenser, a thermometer, and a dropping funnel was charged with 1-methylpiperazine (10.3 g) (0.103 mol) and 1,2-dimethoxyethane (100 g), a solution of methanedisulfonyl chloride (10.0 g) (0.047 mol) dissolved in 1,2-dimethoxyethane (10 g) was added dropwise over 20 minutes while maintaining the temperature at 0° C. Subsequently, while maintaining the temperature at 0° C., a solution of triethylamine (11.4 g) (0.113 mol) dissolved in 1,2-dimethoxyethane (10 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bis(1-methylpiperazine) (6.7 g) (0.020 mol). The yield of the methanedisulfonic acid bis(1-methylpiperazine) was 41.9% based on the amount of the methanedisulfonyl chloride.

The resulting methanedisulfonic acid bis(1-methylpiperazine) was identified by its properties described below.

$^1$H-nuclear magnetic resonance spectrum (solvent: CDCl$_3$) δ (ppm): 3.32 (s, 6H), 3.55 (t, 8H), 3.67 (t, 8H), 5.11 (s, 2H)

A non-aqueous electrolyte solution was prepared in the same manner as in Example 23 except that the compound 33 was used in an amount of 1.0% by mass instead of the compound 29 in "(Preparation of non-aqueous electrolyte solution)".

EXAMPLE 29

Preparation of 1,2-ethanedisulfonic acid bismorpholine (compound 34)

A 200-mL four-necked flask equipped with a stirrer, a condenser, a thermometer, and a dropping funnel was charged with morpholine (8.4 g) (0.097 mol) and 1,2-dimethoxyethane (100 g), a solution of 1,2-ethane disulfonyl chloride (10.0 g) (0.044 mol) dissolved in 1,2-dimethoxyethane (10 g) was added dropwise over 20 minutes while maintaining the temperature at 0° C. Subsequently, while maintaining the temperature at 0° C., a solution of triethylamine (10.7 g) (0.106 mol) dissolved in 1,2-dimethoxyethane (10 g) was added dropwise over 1 hour, followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give 1,2-ethanedisulfonic acid bismorpholine (7.6 g) (0.023 mol). The yield of the 1,2-ethanedisulfonic acid bismorpholine was 52.6% based on the amount of the 1,2-ethane disulfonyl chloride.

The resulting 1,2-ethanedisulfonic acid bismorpholine was identified by its properties described below.

$^1$H-nuclear magnetic resonance spectrum (solvent: CDCl$_3$) δ (ppm): 3.34 (t, 8H), 3.65 (t, 8H), 5.02 (s, 4H)

A non-aqueous electrolyte solution was prepared in the same manner as in Example 23 except that the compound 34 was used in an amount of 1.0% by mass instead of the compound 29 in "(Preparation of non-aqueous electrolyte solution)".

COMPARATIVE EXAMPLE 15

A non-aqueous electrolyte solution was prepared in the same manner as in Example 23 except that the compound 29 was not used in "(Preparation of non-aqueous electrolyte solution)" in Example 23.

COMPARATIVE EXAMPLE 16

A non-aqueous electrolyte solution was prepared in the same manner as in Example 23 except that 1,3-propane sultone (PS) was used in an amount of 1.0% by mass instead of the compound 29 in "(Preparation of non-aqueous electrolyte solution)" in Example 23.

COMPARATIVE EXAMPLE 17

A non-aqueous electrolyte solution was prepared in the same manner as in Example 23 except that vinylene carbonate (VC) was used in an amount of 1.0% by mass instead of the compound 29 in "(Preparation of non-aqueous electrolyte solution)" in Example 23.

COMPARATIVE EXAMPLE 18

A non-aqueous electrolyte solution was prepared in the same manner as in Comparative Example 17 except that the amount of the vinylene carbonate (VC) was 2.0% by mass.

COMPARATIVE EXAMPLE 19

A non-aqueous electrolyte solution was prepared in the same manner as in Example 23 except that fluoroethylene carbonate (FEC) was used in an amount of 1.0% by mass instead of the compound 29 in "(Preparation of non-aqueous electrolyte solution)" in Example 23.

COMPARATIVE EXAMPLE 20

A non-aqueous electrolyte solution was prepared in the same manner as in Comparative Example 19 except that the amount of the fluoroethylene carbonate (FEC) was 2.0% by mass.

<Evaluation>

The compounds 29 to 34 prepared in the examples and the non-aqueous electrolyte solutions prepared in the examples and comparative examples were evaluated as follows.

(LUMO Energy, Standard Enthalpy of Formation (H), Enthalpy Change ($\Delta$H) with Hydrolysis Reaction)

The LUMO (lowest unoccupied molecular orbital) energies of the resulting compounds 29 to 34 prepared in the examples were derived using the Gaussian 03 software. The results are shown in Table 14.

Further, the standard enthalpies of formation (H) of the compounds 29 to 34 prepared in the examples were derived using the MOPAC 97 software. The results are shown in Table 14.

Further, the enthalpy changes ($\Delta$H) with hydrolysis reaction of the compounds 29 to 34 prepared in the examples were derived using the Gaussian 03 software. The results are shown in Table 14.

TABLE 14

| Structure | LUMO energy (eV) | H (kcal/mol) | $\Delta$H (kcal/mol) |
|---|---|---|---|
| Compound 29 | 0.29 | −139.9 | −3.2 |
| Compound 30 | 0.27 | −158.5 | −2.6 |

TABLE 14-continued

| Structure | LUMO energy (eV) | H (kcal/mol) | $\Delta$H (kcal/mol) |
|---|---|---|---|
| Compound 31 | 0.15 | −213.5 | −3.0 |
| Compound 32 | 0.21 | −125.8 | −3.5 |
| Compound 33 | 0.32 | −155.8 | −1.9 |
| Compound 34 | 0.36 | −211.0 | −1.8 |

Table 14 shows that the disulfonic acid amide compounds (compounds 29 to 34) represented by the formula (17) have a LUMO energy of about 0.15 eV to about 0.36 eV, and these disulfonic acid amide compounds according to the additive for a non-aqueous electrolyte solution of the present invention have a lower LUMO energy than solvents of commonly used non-aqueous electrolyte solutions (for example, cyclic carbonate and chain carbonate: LUMO energy of about 1.2 eV). Therefore, in cases where the compounds 29 to 34 are used as an additive for a non-aqueous electrolyte solution for electrical storage devices such as non-aqueous electrolyte solution secondary cells, the compounds 29 to 34 are electrochemically reduced prior to electrochemical reduction of solvents of non-aqueous electrolyte solutions, and an SEI is formed on an electrode, whereby decomposition of solvent molecules in an electrolyte solution can be suppressed. As a result, a high resistant film produced by decomposition of the solvent is less likely to be formed on an electrode to probably improve cell performance.

Table 14 shows that the disulfonic acid amide compounds (compounds 29 to 34) represented by the formula (17) have a standard enthalpy of formation (H) of about −125.8 kcal/mol to about −213.5 kcal/mol. That is, the compounds 29 to 34 according to the present invention have excellent storage stability in a non-aqueous electrolyte solution. Further, in cases where such a non-aqueous electrolyte solution is used for electrical storage devices such as secondary batteries, the compounds subjected to electrochemical reduction decomposition enables formation of an SEI on an electrode. As a result, decomposition of solvent molecules in an electrolyte solution can be suppressed.

Further, Table 14 shows that the disulfonic acid amide compounds (compounds 29 to 34) represented by the formula (17) have an enthalpy change (ΔH) with hydrolysis reaction of about −1.8 kcal/mol to about −3.5 kcal/mol. That is, the compounds 29 to 34 according to the present invention are also stable to moisture. Further, in cases where such a non-aqueous electrolyte solution is used for electrical storage devices such as secondary batteries, the compounds subjected to electrochemical reduction decomposition enables formation of an SEI on an electrode. As a result, decomposition of solvent molecules in an electrolyte solution can be suppressed.

Thus, the disulfonic acid amide compounds represented by the formula (17) according to the additive for a non-aqueous electrolyte solution of the present invention have a sufficiently low LUMO energy, excellent storage stability when contained in a non-aqueous electrolyte solution as an additive for a non-aqueous electrolyte solution, and excellent stability to moisture. This shows that such compounds are effective as a novel additive for a non-aqueous electrolyte solution capable of forming a stable SEI on an electrode of electrical storage devices such as non-aqueous electrolyte solution secondary cells.

(Evaluation of Stability)

The compounds 29 to 34 obtained in the examples and commonly used fluoroethylene carbonate (FEC) were subjected to a storage test for 90 days under constant temperature and humidity conditions of a temperature of 40±2° C. and humidity of 75±5%. The degradability of each compound was measured and evaluated with $^1$H-nuclear magnetic resonance spectrum ($^1$H-NMR). Table 15 shows the results.

Good: There is no change in peaks in $^1$H-NMR before and after storage.
Poor: There is a change in peaks in $^1$H-NMR before and after storage.

TABLE 15

| Additive | Stability |
|---|---|
| Compound 29 | Good |
| Compound 30 | Good |
| Compound 31 | Good |
| Compound 32 | Good |
| Compound 33 | Good |
| Compound 34 | Good |
| FEC | Poor |

(Preparation of Cell)

$LiMn_2O_4$ as a cathode active material and a carbon black as a conductivity imparting agent were dry mixed, and the mixture was uniformly dispersed in N-methyl-2-pyrrolidone (NMP) in which polyvinylidene fluoride (PVDF) was dissolved as a binder to prepare a slurry. The resulting slurry was applied to an aluminum foil (square, thickness of 20 μm) that is to be a cathode current collector, and the NMP was dried off to prepare a cathode sheet. The resulting cathode sheet had a solid mass ratio of cathode active material:conductivity imparting agent:PVDF=80:10:10.

A commercially available graphite-coated electrode sheet (produced by Hohsen Corp.) was used as an anode sheet.

A cylindrical secondary battery was prepared in such a way that an anode sheet and a cathode sheet were laminated and a polyethylene separator was disposed between the sheets in a non-aqueous electrolyte solution prepared in each of the examples and comparative examples.

(Measurement of Discharge Capacity Retention and Internal Resistance Ratio)

The resulting cylindrical secondary batteries were subjected to a charge/discharge cycle test under the conditions of a temperature of 25° C., a charging rate of 0.3 C, a discharging rate of 0.3 C, a charge termination voltage of 4.2 V, and a discharge termination voltage of 2.5 V. Table 16 shows discharge capacity retention (%) and internal resistance ratio after 200 cycles.

The "discharge capacity retention (%)" after 200 cycles was determined by dividing the discharge capacity (mAh) after 200 cycles of the cycle test by the discharge capacity (mAh) after 10 cycles of the cycle test and multiplying the resulting value by 100. Further, the "internal resistance ratio" after 200 cycles was expressed as a value of the resistance after 200 cycles of the cycle test relative to a value of the resistance before the cycle test taken as 1.

TABLE 16

| | Electrolyte | Solvent | Additive | Discharge capacity retention (%) | Internal resistance ratio |
|---|---|---|---|---|---|
| Example 23 | $LiPF_6$ 1.0 mol/L | EC/DEC (30/70) vol % | Compound 29 0.5% by mass | 93 | 1.24 |
| Example 24 | $LiPF_6$ 1.0 mol/L | EC/DEC (30/70) vol % | Compound 29 1.0% by mass | 94 | 1.18 |
| Example 25 | $LiPF_6$ 1.0 mol/L | EC/DEC (30/70) vol % | Compound 30 1.0% by mass | 95 | 1.13 |
| Example 26 | $LiPF_6$ 1.0 mol/L | EC/DEC (30/70) vol % | Compound 31 1.0% by mass | 92 | 1.15 |
| Example 27 | $LiPF_6$ 1.0 mol/L | EC/DEC (30/70) vol % | Compound 32 1.0% by mass | 93 | 1.12 |
| Example 28 | $LiPF_6$ 1.0 mol/L | EC/DEC (30/70) vol % | Compound 33 1.0% by mass | 92 | 1.15 |
| Example 29 | $LiPF_6$ 1.0 mol/L | EC/DEC (30/70) vol % | Compound 34 1.0% by mass | 91 | 1.17 |
| Comparative Example 15 | $LiPF_6$ 1.0 mol/L | EC/DEC (30/70) vol % | None | 74 | 1.83 |
| Comparative Example 16 | $LiPF_6$ 1.0 mol/L | EC/DEC (30/70) vol % | PS 1.0% by mass | 77 | 1.68 |

TABLE 16-continued

| | Electrolyte | Solvent | Additive | Discharge capacity retention (%) | Internal resistance ratio |
|---|---|---|---|---|---|
| Comparative Example 17 | LiPF$_6$ 1.0 mol/L | EC/DEC (30/70) vol % | VC 1.0% by mass | 83 | 1.69 |
| Comparative Example 18 | LiPF$_6$ 1.0 mol/L | EC/DEC (30/70) vol % | VC 2.0% by mass | 84 | 1.53 |
| Comparative Example 19 | LiPF$_6$ 1.0 mol/L | EC/DEC (30/70) vol % | FEC 1.0% by mass | 81 | 1.66 |
| Comparative Example 20 | LiPF$_6$ 1.0 mol/L | EC/DEC (30/70) vol % | FEC 2.0% by mass | 83 | 1.67 |

Table 16 shows that the cylindrical secondary batteries each using a non-aqueous electrolyte solution of each of the examples have a higher discharge capacity retention in a cycle test than the cylindrical secondary batteries each using a non-aqueous electrolyte solution of each of the comparative examples. Therefore, in cells such as non-aqueous electrolyte solution secondary cells, the non-aqueous electrolyte solutions of the examples provide an SEI with higher stability to charge/discharge cycle on the surface of an electrode of the cells than the non-aqueous electrolyte solutions of the comparative examples.

Further, the non-aqueous electrolyte solutions of the examples have smaller internal resistance than the non-aqueous electrolyte solutions of the comparative examples, and therefore suppress an increase in internal resistance during a cycle test.

PRODUCTION EXAMPLE 1

A 200-mL four-necked flask equipped with a stirrer, a condenser, a thermometer, and a dropping funnel was charged with 2,2,2-trifluoroethanol (9.4 g) (0.094 mol) and 1,2-dimethoxyethane (40.0 g), and methanedisulfonyl chloride (10.0 g) (0.047 mol) mixed with 1,2-dimethoxyethane (10.0 g) was added dropwise over 20 minutes while maintaining the temperature at 0° C. Triethylamine (9.5 g) (0.094 mol) mixed with 1,2-dimethoxyethane (10.0 g) was added dropwise over 1 hour while maintaining the temperature at 0° C., followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bis(2,2,2-trifluoroethyl ester) (12.0 g) (0.035 mol). The yield of the methanedisulfonic acid bis(2,2,2-trifluoroethyl ester) was 75.2% based on the amount of the methanedisulfonyl chloride. The resulting methanedisulfonic acid bis(2,2,2-trifluoroethyl ester) was identified by its properties described below.

$^1$H-nuclear magnetic resonance spectrum (solvent: CD$_3$CN) δ (ppm): 5.39 (s, 2H), 4.83 (dd, 4H) LC/MS (m/z [M-H]+): 339

PRODUCTION EXAMPLE 2

A 200-mL four-necked flask equipped with a stirrer, a condenser, a thermometer, and a dropping funnel was charged with 1,1,1-trifluoro-2-propanol (10.7 g) (0.094 mol) and 1,2-dimethoxyethane (40.0 g), and methanedisulfonyl chloride (10.0 g) (0.047 mol) mixed with 1,2-dimethoxyethane (10.0 g) was added dropwise over 20 minutes while maintaining the temperature at 0° C. Triethylamine (9.5 g) (0.094 mol) mixed with 1,2-dimethoxyethane (10.0 g) was added dropwise over 1 hour while maintaining the temperature at 0° C., followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bis(2,2,2-trifluoro-1-methyl ethyl ester) (13.4 g) (0.036 mol). The yield of the methanedisulfonic acid bis(2,2,2-trifluoro-1-methyl ethyl ester) was 77.4% based on the amount of the methanedisulfonyl chloride. The resulting methanedisulfonic acid bis(2,2,2-trifluoro-1-methyl ethyl ester) was identified by its properties described below.

$^1$H-nuclear magnetic resonance spectrum (solvent: CDCl$_3$) δ (ppm): 5.78 (q, 2H), 5.53 (s, 2H), 1.49 (d, 6H) LC/MS (m/z [M-H]+): 367

PRODUCTION EXAMPLE 3

A 200-mL four-necked flask equipped with a stirrer, a condenser, a thermometer, and a dropping funnel was charged with 3,3,3-trifluoro-1-propanol (10.7 g) (0.094 mol) and 1,2-dimethoxyethane (40.0 g), and methanedisulfonyl chloride (10.0 g) (0.047 mol) mixed with 1,2-dimethoxyethane (10.0 g) was added dropwise over 20 minutes while maintaining the temperature at 0° C. Triethylamine (9.5 g) (0.094 mol) mixed with 1,2-dimethoxyethane (10.0 g) was added dropwise over 1 hour while maintaining the temperature at 0° C., followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bis(3,3,3-trifluoro propyl ester) (12.8 g) (0.035 mol). The yield of the methanedisulfonic acid bis(3,3,3-trifluoro propyl ester) was 74.4% based on the amount of the methanedisulfonyl chloride. The resulting methanedisulfonic acid bis(3,3,3-trifluoro propyl ester) was identified by its properties described below.

$^1$H-nuclear magnetic resonance spectrum (solvent: CDCl$_3$) δ (ppm): 5.53 (s, 2H), 3.53 (d, 4H), 2.00 (dd, 4H) LC/MS (m/z [M-H]+): 367

PRODUCTION EXAMPLE 4

A 200-mL four-necked flask equipped with a stirrer, a condenser, a thermometer, and a dropping funnel was charged with 4,4,4-trifluoro-1-butanol (12.0 g) (0.094 mol) and 1,2-dimethoxyethane (40.0 g), and methanedisulfonyl chloride (10.0 g) (0.047 mol) mixed with 1,2-dimethoxyethane (10.0 g) was added dropwise over 20 minutes while maintaining the temperature at 0° C. Triethylamine (9.5 g) (0.094 mol) mixed with 1,2-dimethoxyethane (10.0 g) was added dropwise over 1 hour while maintaining the temperature at 0° C., followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid bis(4,4,4-trifluoro butyl ester) (16.2 g) (0.041 mol). The yield of the methanedisulfonic acid bis(4,4,4-trifluoro butyl ester) was 87.2% based on the amount of the methanedisulfonyl chloride. The resulting methanedisulfonic acid bis(4,4,4-trifluoro butyl ester) was identified by its properties described below.

$^1$H-nuclear magnetic resonance spectrum (solvent: $CDCl_3$) δ (ppm): 5.52 (s, 2H), 3.55 (d, 4H), 1.81 (dd, 4H), 1.48 (dd, 4H)
LC/MS (m/z [M-H]+): 395

PRODUCTION EXAMPLE 5

A 200-mL four-necked flask equipped with a stirrer, a condenser, a thermometer, and a dropping funnel was charged with 2,2,2-trifluoroethanol (4.7 g) (0.047 mol) and 1,2-dimethoxyethane (20.0 g), and methanedisulfonyl chloride (10.0 g) (0.047 mol) mixed with 1,2-dimethoxyethane (10.0 g) was added dropwise over 20 minutes while maintaining the temperature at 0° C. Triethylamine (4.8 g) (0.047 mol) mixed with 1,2-dimethoxyethane (5.0 g) was added dropwise over 1 hour while maintaining the temperature at 0° C., followed by stirring for 6 hours at the same temperature. Further, phenol (4.4 g) (0.047 mol) and 1,2-dimethoxyethane (20.0 g) were added dropwise over 20 minutes at 0° C. Triethylamine (4.8 g) (0.047 mol) mixed with 1,2-dimethoxyethane (5.0 g) was added dropwise over 1 hour while maintaining the temperature at 0° C., followed by stirring over night at the same temperature.

After the completion of the reaction, the reaction solution was filtered, and toluene (100.0 g) and water (50.0 g) were added to the filtrate. Then, an organic phase was separated from the aqueous phase, and part of the solvent was removed from the organic phase by reduced pressure distillation at 25° C., whereby crystals were obtained. The crystals were filtered and dried to give methanedisulfonic acid-2,2,2-trifluoroethyl ester phenyl ester (12.7 g) (0.038 mol). The yield of the methanedisulfonic acid-2,2,2-trifluoroethyl ester phenyl ester was 80.8% based on the amount of the methanedisulfonyl chloride.

The resulting methanedisulfonic acid-2,2,2-trifluoroethyl ester phenyl ester was identified by its properties described below.

$^1$H-nuclear magnetic resonance spectrum (solvent: $CDCl_3$) δ (ppm): 7.33 (d, 2H), 7.25 (s, 1H), 7.21 (m, 2H), 5.53 (s, 2H), 4.05 (d, 2H)
LC/MS (m/z [M-H]+): 333

EXAMPLE 30

Preparation of methanedisulfonic acid-2,2-difluoro vinyl ester-2,2,2-trifluoroethyl ester (compound 35: halogen-containing disulfonic acid ester compound represented by the formula (21))

A 500-mL four-necked flask equipped with a stirrer, a condenser, a thermometer, and a dropping funnel was charged with methanedisulfonic acid bis(2,2,2-trifluoroethyl ester) (12.0 g) (0.035 mol) prepared in the same manner as in Production Example 1 and tetrahydrofuran (175.0 mL), and the contents were cooled to −78° C. A 2.6-mol/L n-butyllithium-hexane solution (56.0 mL) (0.15 mol) was added dropwise over 1 hour while maintaining the temperature at −78° C., followed by stirring for 6 hours at the same temperature. After the completion of the reaction, to the reaction solution were added dropwise a tetrahydrofuran-water mixed solution (volume ratio of 1:1) (116.7 mL) and a saturated aqueous ammonium chloride solution (140.0 mL). Next, extraction was repeated three times using ethyl acetate (116.7 mL). Part of the solvent was removed from the resulting organic phase by reduced pressure distillation at 25° C. to give a concentrate. The concentrate was purified by column chromatography (an ethyl acetate-heptane mixed solvent was used as a mobile phase) to give methanedisulfonic acid-2,2-difluoro vinyl ester-2,2,2-trifluoroethyl ester (6.5 g) (0.020 mol). The yield of the methanedisulfonic acid-2,2-difluoro vinyl ester-2,2,2-trifluoroethyl ester was 57.1% based on the amount of the methanedisulfonic acid bis(2,2,2-trifluoroethyl ester).

The resulting methanedisulfonic acid-2,2-difluoro vinyl ester-2,2,2-trifluoroethyl ester was identified by its properties described below.

$^1$H-nuclear magnetic resonance spectrum (solvent: $CDCl_3$) δ (ppm): 6.36 (dd, 1H), 4.93 (s, 2H), 4.72 (dd, 2H)
LC/MS (m/z [M-H]+): 319

EXAMPLE 31

Preparation of methanedisulfonic acid bis(2,2-difluoro vinyl ester) (compound 36: halogen-containing disulfonic acid ester compound represented by the formula (23))

A 500-mL four-necked flask equipped with a stirrer, a condenser, a thermometer, and a dropping funnel was charged with methanedisulfonic acid bis(2,2,2-trifluoroethyl ester) (12.0 g) (0.035 mol) prepared in the same manner as in Production Example 1 and tetrahydrofuran (175.0 mL), and the contents were cooled to −78° C. A 2.6-mol/L n-butyllithium-hexane solution (112.0 mL) (0.30 mol) was added dropwise over 1 hour while maintaining the temperature at −78° C., followed by stirring at the same temperature for 6 hours. The contents were heated to −20° C. and stirred at the same temperature for 2 hours. After the completion of the reaction, to the reaction solution were added dropwise a tetrahydrofuran-water mixed solution (volume ratio of 1:1) (116.7 mL) and a saturated aqueous ammonium chloride solution (140.0 mL). Subsequently, extraction was repeated three times using ethyl acetate (116.7 mL). Part of the solvent was removed from the resulting organic phase by reduced pressure distillation at 25° C. to give a concentrate. The concentrate was purified by column chromatography (an ethyl acetate-heptane mixed solvent was used as a mobile phase) to give methanedisulfonic acid bis(2,2-difluoro vinyl ester) (7.0 g) (0.023 mol). The yield of the methanedisulfonic acid bis(2,2-difluoro vinyl ester) was 66.4% based on the amount of the methanedisulfonic acid bis(2,2,2-trifluoroethyl ester).

The resulting methanedisulfonic acid bis(2,2-difluoro vinyl ester) was identified by its properties described below.

$^1$H-nuclear magnetic resonance spectrum (solvent: CDCl$_3$) δ (ppm): 6.38 (dd, 2H), 4.92 (s, 2H) LC/MS (m/z [M-H]+): 299

EXAMPLE 32

Preparation of methanedisulfonic acid bis(2,2-difluoro-1-methyl vinyl ester) (compound 37)

A 500-mL four-necked flask equipped with a stirrer, a condenser, a thermometer, and a dropping funnel was charged with methanedisulfonic acid bis(2,2,2-trifluoro-1-methyl ethyl ester) (12.9 g) (0.035 mol) prepared in the same manner as in Production Example 2 and tetrahydrofuran (175.0 mL), and the contents were cooled to −78° C. A 2.6-mol/L n-butyllithium-hexane solution (112.0 mL) (0.30 mol) was added dropwise over 1 hour while maintaining the temperature at −78° C., followed by stirring at the same temperature for 6 hours. The contents were heated to −20° C. and stirred at the same temperature for 2 hours. After the completion of the reaction, to the reaction solution were added dropwise a tetrahydrofuran-water mixed solution (volume ratio of 1:1) (116.7 mL) and a saturated aqueous ammonium chloride solution (140.0 mL). Next, extraction was repeated three times using ethyl acetate (116.7 mL). Part of the solvent was removed from the resulting organic phase by reduced pressure distillation at 25° C. to give a concentrate. The concentrate was purified by column chromatography (an ethyl acetate-heptane mixed solvent was used as a mobile phase) to give methanedisulfonic acid bis(2,2-difluoro-1-methyl vinyl ester) (8.5 g) (0.026 mol). The yield of the methanedisulfonic acid bis(2,2-difluoro-1-methyl vinyl ester) was 74.3% based on the amount of the methanedisulfonic acid bis(2,2,2-trifluoro-1-methyl ethyl ester).

The resulting methanedisulfonic acid bis(2,2-difluoro-1-methyl vinyl ester) was identified by its properties described below.

$^1$H-nuclear magnetic resonance spectrum (solvent: CDCl$_3$) δ (ppm): 5.53 (s, 2H), 1.71 (s, 6H) LC/MS (m/z [M-H]+): 327

EXAMPLE 33

Preparation of methanedisulfonic acid bis(3,3-difluoro-2-propenyl ester) (compound 38)

A 500-mL four-necked flask equipped with a stirrer, a condenser, a thermometer, and a dropping funnel was charged with methanedisulfonic acid bis(3,3,3-trifluoro propyl ester) (12.8 g) (0.035 mol) prepared in the same manner as in Production Example 3 and tetrahydrofuran (175.0 mL), and the contents were cooled to −78° C. A 2.6-mol/L n-butyllithium-hexane solution (112.0 mL) (0.30 mol) was added dropwise over 1 hour while maintaining the temperature at −78° C., followed by stirring at the same temperature for 6 hours. The contents were heated to −20° C. and stirred at the same temperature for 2 hours. After the completion of the reaction, to the reaction solution were added dropwise a tetrahydrofuran-water mixed solution (volume ratio of 1:1) (116.7 mL) and a saturated aqueous ammonium chloride solution (140.0 mL). Then, extraction was repeated three times using ethyl acetate (116.7 mL). Part of the solvent was removed from the resulting organic phase by reduced pressure distillation at 25° C. to give a concentrate. The concentrate was purified by column chromatography (an ethyl acetate-heptane mixed solvent was used as a mobile phase) to give methanedisulfonic acid bis(3,3-difluoro-2-propenyl ester) (7.0 g) (0.021 mol). The yield of the methanedisulfonic acid bis(3,3-difluoro-2-propenyl ester) was 60.0% based on the amount of the methanedisulfonic acid bis(3,3,3-trifluoro propyl ester).

The resulting methanedisulfonic acid bis(3,3-difluoro-2-propenyl ester) was identified by its properties described below.

$^1$H-nuclear magnetic resonance spectrum (solvent: CDCl$_3$) δ (ppm): 5.53 (s, 2H), 4.47 (dd, 2H), 4.20 (d, 4H) LC/MS (m/z [M-H]+): 327

EXAMPLE 34

Preparation of methanedisulfonic acid bis(4,4-difluoro-3-butenyl ester) (compound 39)

A 500-mL four-necked flask equipped with a stirrer, a condenser, a thermometer, and a dropping funnel was charged with methanedisulfonic acid bis(4,4,4-trifluoro butyl ester) (13.9 g) (0.035 mol) prepared in the same manner as in Production Example 4 and tetrahydrofuran (175.0 mL), and the contents were cooled to −78° C. A 2.6-mol/L n-butyllithium-hexane solution (112.0 mL) (0.30 mol) was added dropwise over 1 hour while maintaining the temperature at −78° C., followed by stirring at the same temperature for 6 hours. The contents were heated to −20° C. and stirred at the same temperature for 2 hours. After the completion of the reaction, to the reaction solution were added dropwise a tetrahydrofuran-water mixed solution (volume ratio of 1:1) (116.7 mL) and a saturated aqueous ammonium chloride solution (140.0 mL). Subsequently, extraction was repeated three times using ethyl acetate (116.7 mL). Part of the solvent was removed from the resulting organic phase by reduced pressure distillation at 25° C. to give a concentrate. The concentrate was purified by column chromatography (an ethyl acetate-heptane mixed solvent was used as a mobile phase) to give methanedisulfonic acid bis(4,4-difluoro-3-butenyl ester) (6.8 g) (0.019 mol). The yield of the methanedisulfonic acid bis(4,4-difluoro-3-butenyl ester) was 54.3% based on the amount of the methanedisulfonic acid bis(4,4,4-trifluoro butyl ester).

The resulting methanedisulfonic acid bis(4,4-difluoro-3-butenyl ester) was identified by its properties described below.

$^1$H-nuclear magnetic resonance spectrum (solvent: CDCl$_3$) δ (ppm): 5.52 (s, 2H), 4.28 (dd, 2H), 3.57 (d, 4H), 2.15 (d, 4H)
LC/MS (m/z [M-H]+): 355

EXAMPLE 35

Preparation of methanedisulfonic acid-2,2-difluoro vinyl ester phenyl ester) (compound 40)

A 500-mL four-necked flask equipped with a stirrer, a condenser, a thermometer, and a dropping funnel was charged with methanedisulfonic acid-2,2,2-trifluoroethyl ester phenyl ester (11.7 g) (0.035 mol) prepared in the same manner as in Production Example 5 and tetrahydrofuran (175.0 mL), and the contents were cooled to −78° C. A 2.6-mol/L n-butyllithium-hexane solution 56.0 mL (0.15 mol) was added dropwise over 1 hour while maintaining the temperature at −78° C., followed by stirring for 6 hours at the same temperature. After the completion of the reaction, to the reaction solution were added dropwise a tetrahydrofuran-water mixed solution (volume ratio of 1:1) (116.7 mL) and a saturated aqueous ammonium chloride solution (140.0 mL). Subsequently, extraction was repeated three times using ethyl acetate (116.7 mL). Part of the solvent was removed from the resulting organic phase by reduced pressure distillation at 25° C. to give a concentrate. The resulting concentrate was purified by column chromatography (an ethyl acetate-heptane mixed solvent was used as a mobile phase) to give methanedisulfonic acid-2,2-difluoro vinyl ester phenyl ester (6.0 g) (0.019 mol). The yield of the methanedisulfonic acid-2,2-difluoro vinyl ester phenyl ester was 54.2% based on the amount of the methanedisulfonic acid-2,2-trifluoroethyl ester phenyl ester.

The resulting methanedisulfonic acid-2,2-difluoro vinyl ester phenyl ester was identified by its properties described below.

$^1$H-nuclear magnetic resonance spectrum (solvent: CDCl$_3$) δ (ppm): 7.34 (d, 2H), 7.25 (s, 1H), 7.20 (m, 2H), 5.52 (s, 2H), 3.80 (d, 1H)
LC/MS (m/z [M-H]+): 313

COMPARATIVE EXAMPLE 21

Preparation of methanedisulfonic acid bis(2,2,2-trifluoroethyl ester) (compound 41)

Methanedisulfonic acid bis(2,2,2-trifluoroethyl ester) (12.0 g) (0.035 mol) was prepared in the same manner as in Production Example 1.

COMPARATIVE EXAMPLE 22

Preparation of methanedisulfonic acid bis(2,2,2-trichloroethyl ester) (compound 42)

Methanedisulfonic acid bis(2,2,2-trichloroethyl ester) (13.0 g) (0.029 mol) was prepared in the same manner as in Production Example 1 except that 2,2,2-trichloroethanol (14.0 g) (0.094 mol) was used instead of 2,2,2-trifluoroethanol (9.4 g) (0.094 mol). The yield of the methanedisulfonic acid bis(2,2,2-trichloroethyl ester) was 63% based on the amount of the methanedisulfonyl chloride.

COMPARATIVE EXAMPLE 23

Preparation of methanedisulfonic acid bis(3,3,3-trifluoro propyl ester) (compound 43)

Methanedisulfonic acid bis(3,3,3-trifluoro propyl ester) (10.0 g) (0.027 mol) was prepared in the same manner as in Production Example 3.
<Evaluation>
(LUMO energy, standard enthalpy of formation (H), enthalpy change (ΔH) with hydrolysis reaction)

The LUMO (lowest unoccupied molecular orbital) energies of the compounds 35 to 43 prepared in the examples and comparative examples were derived using the Gaussian 03 software. The results are shown in Table 17.

Further, the standard enthalpies of formation (H) of the compounds 35 to 43 prepared in the examples and comparative examples were derived using the MOPAC 97 software. The results are shown in Table 17.

Further, the enthalpy changes (ΔH) with hydrolysis reaction of the compounds 35 to 43 in the examples and comparative examples were derived using the Gaussian 03 software. The results are shown in Table 17.

TABLE 17

| | Structure | LUMO energy (eV) | H (kcal/mol) | ΔH (kcal/mol) |
|---|---|---|---|---|
| Compound 35 | 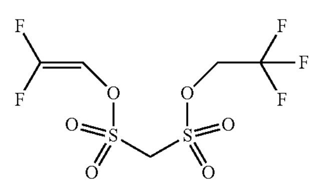 [SMILES: O=S(=O)(CS(=O)(=O)OCC(F)(F)F)OC=C(F)F] | −1.00 | −199.1 | −4.2 |
| Compound 36 | 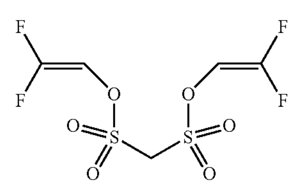 [SMILES: O=S(=O)(CS(=O)(=O)OC=C(F)F)OC=C(F)F] | −1.17 | −211.6 | −4.0 |
| Compound 37 | 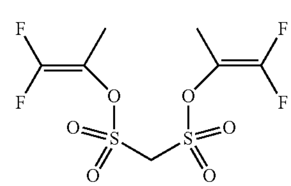 [SMILES: CC(OS(=O)(=O)CS(=O)(=O)OC(C)=C(F)F)=C(F)F] | −1.05 | −209.2 | −3.6 |

TABLE 17-continued

| Structure | LUMO energy (eV) | H (kcal/mol) | ΔH (kcal/mol) |
|---|---|---|---|
| Compound 38 | −1.01 | −189.3 | −3.8 |
| Compound 39 | −1.12 | −190.6 | −3.8 |
| Compound 40 | −1.08 | −215.3 | −3.4 |
| Compound 41 | −0.37 | −246.0 | −4.1 |
| Compound 42 | −0.21 | −258.5 | −4.3 |
| Compound 43 | −0.25 | −252.7 | −5.7 |

Table 17 shows that the halogen-containing disulfonic acid ester compounds (compounds 35 to 40) represented by the formula (19) have a negative LUMO energy of about −1.00 eV to about −1.17 eV, and these halogen-containing disulfonic acid ester compounds according to the additive for a non-aqueous electrolyte solution of the present invention have a low LUMO energy. Therefore, in cases where the compounds 35 to 40 are used as an additive for a non-aqueous electrolyte solution for electrical storage devices such as non-aqueous electrolyte solution secondary cells, the compounds 35 to 40 are electrochemically reduced prior to electrochemical reduction of solvents of non-aqueous electrolyte solutions (for example, cyclic carbonate and chain carbonate: LUMO energy of about 1.2 eV), and an SEI is formed on an electrode, whereby decomposition of solvent molecules in an electrolyte solution can be suppressed. As a result, a high resistant film produced by decomposition of the solvent is less likely to be formed on an electrode to probably improve cell performance.

On the other hand, Table 17 shows that the halogen-containing disulfonic acid ester compounds (compounds 41 to 43) other than the halogen-containing disulfonic acid ester compounds represented by the formula (19) have a relatively high LUMO energy of about −0.37 eV to about −0.21 eV.

That is, the compounds 41 to 43 are relatively stable to electrochemical reduction and are less likely to form an SEI on an electrode.

Table 17 shows that the halogen-containing disulfonic acid ester compounds (compounds 35 to 40) represented by the formula (19) have a standard enthalpy of formation (H) of about −189.3 kcal/mol to about −215.3 kcal/mol. That is, the compounds 35 to 40 according to the present invention have excellent storage stability in a non-aqueous electrolyte solution. Further, in cases where such a non-aqueous electrolyte solution is used for electrical storage devices such as secondary batteries, the compounds subjected to electrochemical reduction decomposition enables formation of an SEI on the surface of an electrode. As a result, decomposition of solvent molecules in an electrolyte solution can be suppressed.

Further, Table 17 shows halogen-containing disulfonic acid ester compounds (compounds 35 to 40) represented by the formula (19) have an enthalpy change (ΔH) with hydrolysis reaction of about −3.4 kcal/mol to about −4.2 kcal/mol. That is, the compounds 35 to 40 according to the present invention are also stable to moisture. Further, in cases where such a non-aqueous electrolyte solution is used for electrical storage devices such as secondary batteries, the compounds subjected to electrochemical reduction decomposition enables formation of an SEI on an electrode. As a result, decomposition of solvent molecules in an electrolyte solution can be suppressed.

Thus, the halogen-containing disulfonic acid ester compounds represented by the formula (19) according to the additive for a non-aqueous electrolyte solution of the present invention have a sufficiently low LUMO energy, excellent storage stability when contained in a non-aqueous electrolyte solution as an additive for a non-aqueous electrolyte solution, and excellent stability to moisture. This shows that such compounds are effective as a novel additive for a non-aqueous electrolyte solution capable of forming a stable SEI on an electrode of electrical storage devices such as non-aqueous electrolyte solution secondary cells.

(Measurement of LSV (linear sweep voltammetry))

Ethylene carbonate (EC) and diethyl carbonate (DEC) were mixed in a volume ratio of EC:DEC=30:70 to prepare a non-aqueous solvent mixture. $LiPF_6$ as an electrolyte was dissolved in the mixture so as to prepare a 1.0 mol/L $LiPF_6$ solution. A halogen-containing disulfonic acid ester compound obtained in each of the examples and comparative examples was added as an additive for a non-aqueous electrolyte solution in an amount of 1.0% by mass of the total weight of the solution containing the non-aqueous solvent mixture and the electrolyte. Polarization was measured in a potential scanning rate of 5 mV/sec using the resulting non-aqueous electrolyte solution, a disk electrode made from glassy carbon as an electrode, and platinum as a counter electrode. A reduction starting voltage was calculated using a silver electrode as a reference electrode, in which the potential with respect to the reference electrode when 100 μA of current flows was defined as oxidation potential and the potential with respect to the reference electrode when 100 μA of current flows was defined as reduction potential. Further, as Reference Example 3, a reduction starting voltage was similarly calculated using a non-aqueous electrolyte solution prepared without adding an additive for a non-aqueous electrolyte solution. Table 18 shows the results.

TABLE 18

| | Electrolyte | Solvent | Additive | LSV Reduction starting voltage (V) |
|---|---|---|---|---|
| Example 30 | $LiPF_6$ 1.0 mol/L | EC/DEC (30/70) vol % | Compound 35 1.0% by mass | −2.8 |
| Example 31 | $LiPF_6$ 1.0 mol/L | EC/DEC (30/70) vol % | Compound 36 1.0% by mass | −2.7 |
| Example 32 | $LiPF_6$ 1.0 mol/L | EC/DEC (30/70) vol % | Compound 37 1.0% by mass | −2.7 |
| Example 33 | $LiPF_6$ 1.0 mol/L | EC/DEC (30/70) vol % | Compound 38 1.0% by mass | −2.6 |
| Example 34 | $LiPF_6$ 1.0 mol/L | EC/DEC (30/70) vol % | Compound 39 1.0% by mass | −2.7 |
| Example 35 | $LiPF_6$ 1.0 mol/L | EC/DEC (30/70) vol % | Compound 40 1.0% by mass | −2.5 |
| Comparative Example 21 | $LiPF_6$ 1.0 mol/L | EC/DEC (30/70) vol % | Compound 41 1.0% by mass | −3.3 |
| Comparative Example 22 | $LiPF_6$ 1.0 mol/L | EC/DEC (30/70) vol % | Compound 42 1.0% by mass | −3.6 |
| Comparative Example 23 | $LiPF_6$ 1.0 mol/L | EC/DEC (30/70) vol % | Compound 43 1.0% by mass | −3.4 |
| Reference Example 3 | $LiPF_6$ 1.0 mol/L | EC/DEC (30/70) vol % | None | −3.6 |

Table 18 shows that the non-aqueous electrolyte solutions each containing a halogen-containing disulfonic acid ester compound obtained in each of the examples have a higher reduction starting voltage than the non-aqueous electrolyte solution of Reference Example 3 and the non-aqueous electrolyte solutions each containing a compound prepared in each of the comparative examples. Therefore, in cases where a non-aqueous electrolyte solution containing an additive for a non-aqueous electrolyte solution made from a halogen-containing disulfonic acid ester compound prepared in each of the examples is used for electrical storage devices such as non-aqueous electrolyte solution secondary cells, the halogen-containing disulfonic acid ester compounds according to the present invention are electrochemically reduced prior to electrochemical reduction of the non-aqueous electrolyte solution of Reference Example 3 and the non-aqueous electrolyte solutions containing the respective compound 41 to 43 prepared in the comparative examples. Further, a stable SEI is easily formed on the surface of an electrode of cells such as non-aqueous electrolyte solution secondary cells.

(Preparation of Cell)

$LiMn_2O_4$ as a cathode active material and a carbon black as a conductivity imparting agent were dry mixed, and the mixture was uniformly dispersed in N-methyl-2-pyrrolidone (NMP) in which polyvinylidene fluoride (PVDF) was dissolved as a binder to prepare a slurry. The resulting slurry was applied to an aluminum foil (square, thickness of 20 μm) that is to be a cathode current collector, and the NMP was dried off to prepare a cathode sheet. The resulting cathode sheet had a solid mass ratio of cathode active material:conductivity imparting agent:PVDF=80:10:10.

A commercially available graphite-coated electrode sheet (produced by Hohsen Corp.) was used as an anode sheet.

Ethylene carbonate (EC) and diethyl carbonate (DEC) were mixed in a volume ratio of EC:DEC=30:70 to prepare a non-aqueous solvent mixture. $LiPF_6$ was dissolved as an electrolyte in the mixture so as to prepare a 1.0 mol/L $LiPF_6$ solution, and a halogen-containing disulfonic acid ester compound prepared in each of the examples and comparative examples was added in an amount of 1.0% by mass as an additive for a non-aqueous electrolyte solution. Thus, a non-aqueous electrolyte solution was prepared.

A cylindrical secondary battery was prepared in such a way that an anode sheet and a cathode sheet were laminated and a polyethylene separator was disposed between the sheets in the resulting non-aqueous electrolyte solution. Further, as Reference Example 3, a cylindrical secondary battery was similarly prepared using the non-aqueous electrolyte solution prepared without adding an additive for a non-aqueous electrolyte solution.

(Measurement of Discharge Capacity Retention and Internal Resistance Ratio)

The resulting cylindrical secondary batteries were subjected to a charge/discharge cycle test under the conditions of a temperature of 25° C., a charging rate of 0.3 C, a discharging rate of 0.3 C, a charge termination voltage of 4.2 V, and a discharge termination voltage of 2.5 V. Table 19 shows discharge capacity retention (%) and internal resistance ratio after 200 cycles.

The "discharge capacity retention (%)" after 200 cycles was determined by dividing the discharge capacity (mAh) after 200 cycles of the cycle test by the discharge capacity (mAh) after 10 cycles of the cycle test and multiplying the resulting value by 100. Further, the "internal resistance ratio" after 200 cycles was expressed as a value of the resistance after 200 cycles of the cycle test relative to a value of the resistance before the cycle test taken as 1.

TABLE 19

| | Electrolyte | Solvent | Additive | Discharge capacity retention (%) | Internal resistance ratio |
|---|---|---|---|---|---|
| Example 30 | LiPF$_6$ 1.0 mol/L | EC/DEC (30/70) vol % | Compound 35 1.0% by mass | 93 | 1.16 |
| Example 31 | LiPF$_6$ 1.0 mol/L | EC/DEC (30/70) vol % | Compound 36 1.0% by mass | 94 | 1.20 |
| Example 32 | LiPF$_6$ 1.0 mol/L | EC/DEC (30/70) vol % | Compound 37 1.0% by mass | 92 | 1.18 |
| Example 33 | LiPF$_6$ 1.0 mol/L | EC/DEC (30/70) vol % | Compound 38 1.0% by mass | 94 | 1.12 |
| Example 34 | LiPF$_6$ 1.0 mol/L | EC/DEC (30/70) vol % | Compound 39 1.0% by mass | 92 | 1.11 |
| Example 35 | LiPF$_6$ 1.0 mol/L | EC/DEC (30/70) vol % | Compound 40 1.0% by mass | 91 | 1.17 |
| Comparative Example 21 | LiPF$_6$ 1.0 mol/L | EC/DEC (30/70) vol % | Compound 41 1.0% by mass | 81 | 1.71 |
| Comparative Example 22 | LiPF$_6$ 1.0 mol/L | EC/DEC (30/70) vol % | Compound 42 1.0% by mass | 83 | 1.65 |
| Comparative Example 23 | LiPF$_6$ 1.0 mol/L | EC/DEC (30/70) vol % | Compound 43 1.0% by mass | 78 | 1.59 |
| Reference Example 3 | LiPF$_6$ 1.0 mol/L | EC/DEC (30/70) vol % | None | 74 | 1.83 |

Table 19 shows that the cylindrical secondary batteries each using a non-aqueous electrolyte solution containing a halogen-containing disulfonic acid ester compound obtained in each of the examples have a higher discharge capacity retention in a cycle test than the cylindrical secondary batteries each using the non-aqueous electrolyte solution of Reference Example 3 or a non-aqueous electrolyte solution containing a halogen-containing disulfonic acid ester compound of each of the comparative examples. Therefore, in cells such as non-aqueous electrolyte solution secondary cells, the non-aqueous electrolyte solutions containing an additive for a non-aqueous electrolyte solution formed from a halogen-containing disulfonic acid ester compound obtained in each of Examples 30 to 35 provide an SEI with higher stability to charge/discharge cycle on the surface of an electrode of the cells than the non-aqueous electrolyte solutions containing an additive for a non-aqueous electrolyte solution formed from a compound obtained in each of Comparative Examples 21 to 23 and the non-aqueous electrolyte solution of Reference Example 3.

Further, the non-aqueous electrolyte solutions each containing a halogen-containing disulfonic acid ester compound obtained in each of the examples have smaller internal resistance than the non-aqueous electrolyte solution of Reference Example 3 and the non-aqueous electrolyte solutions each containing a halogen-containing disulfonic acid ester compound of each of the comparative examples, and therefore suppress an increase in internal resistance during a cycle test.

EXAMPLE 36

Preparation of phosphorus-containing sulfonic acid ester compound (compound 44) represented by the formula (25) in which $R^{34}$ is ethyl, $R^{35}$ is ethyl, and $Y^2$ is hydrogen A 200-mL four-necked flask equipped with a stirrer, a condenser, a thermometer, and a dropping funnel was charged with bromoacetic acid (13.9 g) (0.1 mol) and dimethoxyethane (70.0 g), and triethyl phosphite (16.6 g) (0.1 mol) mixed with dimethoxyethane (20.0 g) was added dropwise at 0° C. over 2 hours. The temperature was gradually increased to room temperature, and the solution was stirred over night and rinsed with water and a saturated saline. The dimethoxyethane was removed by distillation to give a reaction product (30 g).

Next, a 200-mL four-necked flask equipped with a stirrer, a condenser, a thermometer, and a dropping funnel was charged with chlorosulfonic acid (23.3 g) (0.2 mol) mixed with phosphoryl chloride (46 g), and subsequently the reaction product (30 g) prepared above was added dropwise over 1 hour. The reaction product was heated to 100° C. over 2 hours, followed by stirring at the same temperature for 20 hours. Then, phosphoryl chloride was removed by normal pressure distillation, and reduced pressure distillation (2 torr, 160° C.) was carried out to give an oily reaction product (25 g).

Then, water (50 g) was added to the resulting oily reaction product (25 g), followed by stirring at 100° C. for 12 hours. After the completion of the reaction, water was removed by reduced pressure disillation to give a reaction product (20 g).

Subsequently, sulfolane (120 g) was added to the resulting reaction solution (20 g) and heated to 100° C. Then, phosphorus oxide (28 g) (0.2 mol) and paraformaldehyde (6 g) (0.2 mol) were alternately added and the contents were kept warm with stirring for 10 hours. After the completion of the reaction, the solution was cooled to room temperature, water (30 g) and acetonitrile (100 g) were added thereto, and the resulting solution was separated. Acetonitrile was removed by reduced pressure distillation, the remaining solution was cooled to 0° C., and water (160 g) was added dropwise thereto to obtain crystals. The crystals were collected by filtration, rinsed with hexane, and dried to give a phosphorus-containing sulfonic acid ester compound (compound 44) (6 g) represented by the formula (25) in which $R^{34}$ was ethyl, $R^{35}$ was ethyl, and $Y^2$ was hydrogen. The yield of the compound 44 was 19% based on the amount of the bromoacetic acid.

(Preparation of Non-Aqueous Electrolyte Solution)

Ethylene carbonate (EC) and diethyl carbonate (DEC) were mixed in a volume ratio of EC:DEC=30:70 to prepare a non-aqueous solvent mixture. $LiPF_6$ as an electrolyte was dissolved in the mixture so as to prepare a 1.0 mol/L $LiPF_6$ solution. The compound 44 prepared as an additive for a non-aqueous electrolyte solution was added in an amount of 0.5% by mass of the total weight of the solution containing the non-aqueous solvent mixture and the electrolyte. Thus, a non-aqueous electrolyte solution was prepared.

EXAMPLE 37

A non-aqueous electrolyte solution was prepared in the same manner as in Example 36 except that the amount of the compound 44 was 1.0% by mass in "Preparation of non-aqueous electrolyte solution".

EXAMPLE 38

Preparation of phosphorus-containing sulfonic acid ester compound (compound 45) represented by the formula (25) in which $R^{34}$ is propyl, $R^{35}$ is propyl, and $Y^2$ is hydrogen A phosphorus-containing sulfonic acid ester compound (compound 45) (8 g) represented by the formula (25) in which $R^{34}$ was propyl, $R^{35}$ was propyl, and $Y^2$ was hydrogen was prepared in the same manner as in Example 37 except that the phosphite tripropyl (20.8 g) (0.1 mol) was used instead of triethyl phosphite (16.6 g) (0.1 mol). The yield of the compound 45 was 23% based on the amount of the bromoacetic acid.

(Preparation of Non-Aqueous Electrolyte Solution)

Ethylene carbonate (EC) and diethyl carbonate (DEC) were mixed in a volume ratio of EC:DEC=30:70 to prepare a non-aqueous solvent mixture. $LiPF_6$ as an electrolyte was dissolved in the mixture so as to prepare a 1.0 mol/L $LiPF_6$ solution. The compound 45 prepared as an additive for a non-aqueous electrolyte solution was added in an amount of 1.0% by mass of the total weight of the solution containing the non-aqueous solvent mixture and the electrolyte. Thus, a non-aqueous electrolyte solution was prepared.

EXAMPLE 39

Preparation of phosphorus-containing sulfonic acid ester compound (compound 46) represented by the formula (26) in which $R^{34}$ is ethyl, $R^{35}$ is ethyl, $R^{38}$ is ethyl, $R^{39}$ is ethyl, and $Y^2$ is hydrogen A 200-mL four-necked flask equipped with a stirrer, a condenser, a thermometer, and a dropping funnel was charged with bromoacetic acid (13.9 g) (0.1 mol) and dimethoxyethane (70.0 g), and triethyl phosphite (16.6 g) (0.1 mol) mixed with dimethoxyethane (20.0 g) was added dropwise at 0° C. over 2 hours. The contents were gradually heated to room temperature, stirred over night, and rinsed with water and a saturated saline. The dimethoxyethane was removed by distillation to give a reaction product (30 g).

Next, to a 200-mL four-necked flask equipped with a stirrer, a condenser, a thermometer, and a dropping funnel was added dropwise chlorosulfonic acid (23.3 g) (0.2 mol) mixed with phosphoryl chloride (46 g) over 1 hour. Sequentially, the reaction product (30 g) obtained above was added dropwise thereto over 1 hour. Then, the solution was heated to 100° C. over 2 hours, and stirred at the same temperature for 20 hours. The phosphoryl chloride was removed by normal pressure distillation, and reduced pressure distillation (2 torr, 160° C.) was carried out to give an oily reaction product (25 g).

Next, a 200-mL four-necked flask was charged with dimethoxyethane (70 g) and ethanol (13.8 g) (0.3 mol), and the solution was cooled to 0° C. The oily reaction product (25 g) obtained above was added dropwise to the solution over 2 hours, followed by dropwise addition of triethylamine (41 g) (0.4 mol) over 2 hours. The solution was continuously stirred for 10 hours to complete the reaction, the reaction solution was filtered to remove an inorganic salt, and toluene (100 g) and water (25 g) were added to the filtrate. Then, an organic phase was separated from the aqueous phase, and the toluene was removed from the organic phase by reduced pressure distillation. Subsequently, the remaining solution was cooled to 0° C., and methanol (40 g) was added dropwise over 3 hours to give crystals. The crystals were separated by filtration and dried under reduced pressure to give a phosphorus-containing sulfonic acid ester compound (compound 46) (10 g) represented by the formula (26) in which $R^{34}$ was ethyl, $R^{35}$ was ethyl, $R^{38}$ was ethyl, $R^{39}$ was ethyl, and $Y^2$ was hydrogen. The yield of the compound 46 was 26% based on the amount of the bromoacetic acid.

(Preparation of Non-Aqueous Electrolyte Solution)

Ethylene carbonate (EC) and diethyl carbonate (DEC) were mixed in a volume ratio of EC:DEC=30:70 to prepare a non-aqueous solvent mixture. $LiPF_6$ as an electrolyte was dissolved in the mixture so as to prepare a 1.0 mol/L $LiPF_6$ solution. The compound 46 prepared as an additive for a non-aqueous electrolyte solution was added in an amount of 1.0% by mass of the total weight of the solution containing the non-aqueous solvent mixture and the electrolyte. Thus, a non-aqueous electrolyte solution was prepared.

EXAMPLE 40

Preparation of phosphorus-containing sulfonic acid ester compound (compound 47) represented by the formula (26) in which $r^{34}$ is ethyl, $r^{35}$ is ethyl, $r^{38}$ is phenyl, $r^{39}$ is phenyl, and $y^2$ is hydrogen A phosphorus-containing sulfonic acid ester compound (compound 47) (8 g) represented by the formula (26) in which $R^{34}$ was ethyl, $R^{35}$ was ethyl, $R^{38}$ was phenyl, $R^{39}$ was phenyl, and $Y^2$ was hydrogen was prepared in the same manner as in Example 39 except that phenol (28.2 g) (0.3 mol) was used instead of an ethanol (13.8 g) (0.3 mol). The yield of the compound 47 was 18% based on the amount of the bromoacetic acid.

(Preparation of Non-Aqueous Electrolyte Solution)

Ethylene carbonate (EC) and diethyl carbonate (DEC) were mixed in a volume ratio of EC:DEC=30:70 to prepare a non-aqueous solvent mixture. $LiPF_6$ as an electrolyte was dissolved in the mixture so as to prepare a 1.0 mol/L $LiPF_6$ solution. The compound 47 prepared as an additive for a non-aqueous electrolyte solution was added in an amount of 1.0% by mass of the total weight of the solution containing the non-aqueous solvent mixture and the electrolyte. Thus, a non-aqueous electrolyte solution was prepared.

COMPARATIVE EXAMPLE 24

A non-aqueous electrolyte solution was prepared in the same manner as in Example 36 except that no compound 44 was used.

COMPARATIVE EXAMPLE 25

A non-aqueous electrolyte solution was prepared in the same manner as in Example 37 except that 1,3-propane sultone (PS) was used instead of the compound 44.

COMPARATIVE EXAMPLE 26

A non-aqueous electrolyte solution was prepared in the same manner as in Example 37 except that vinylene carbonate (VC) was used instead of the compound 44.

COMPARATIVE EXAMPLE 27

A non-aqueous electrolyte solution was prepared in the same manner as in Comparative Example 26 except that the amount of the vinylene carbonate (VC) was 2.0% by mass.

COMPARATIVE EXAMPLE 28

A non-aqueous electrolyte solution was prepared in the same manner as in Example 37 except that fluoroethylene carbonate (FEC) was used instead of the compound 44.

COMPARATIVE EXAMPLE 29

A non-aqueous electrolyte solution was prepared in the same manner as in Comparative Example 28 except that the amount of the fluoroethylene carbonate (FEC) was 2.0% by mass.

<Evaluation>
(LUMO Energy, Standard Enthalpy of Formation (H), Enthalpy Change (ΔH) with Hydrolysis Reaction)

The LUMO (lowest unoccupied molecular orbital) energies of the compounds 44 to 47 prepared in the examples were derived using the Gaussian 03 software. The results are shown in Table 20.

Further, the standard enthalpies of formation (H) of the compounds 44 to 47 prepared in the examples were derived using the MOPAC 97 software. The results are shown in Table 20.

Further, the enthalpy changes (ΔH) with hydrolysis reaction of the compounds 44 to 47 prepared in the examples were derived using the Gaussian 03 software. The results are shown in Table 20.

TABLE 20

| | Structure | LUMO energy (eV) | H (kcal/mol) | ΔH (kcal/mol) |
|---|---|---|---|---|
| Compound 44 | 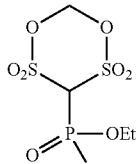 | −0.55 | −172.7 | −2.8 |
| Compound 45 | 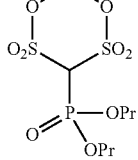 | −0.53 | −178.9 | −3.1 |
| Compound 46 | 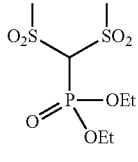 | −0.21 | −156.3 | −3.6 |
| Compound 47 | 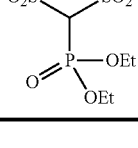 | −0.88 | −173.3 | −3.8 |

Table 20 shows that the phosphorus-containing sulfonic acid ester compounds (compounds 44 to 47) represented by the formula (24) have a negative LUMO energy of about −0.21 eV to about −0.88 eV, and these phosphorus-containing sulfonic acid ester compounds according to the additive for a non-aqueous electrolyte solution of the present invention have a low LUMO energy. Therefore, in cases where the compounds 44 to 47 are used as an additive for a non-aqueous electrolyte solution for electrical storage devices such as non-aqueous electrolyte solution secondary cells, the compounds 44 to 47 are electrochemically reduced prior to electrochemical reduction of solvents of non-aqueous electrolyte solutions (for example, cyclic carbonate and chain carbonate: LUMO energy of about 1.2 eV), and an SEI is formed on an electrode, whereby decomposition of solvent molecules in an electrolyte solution can be suppressed. As a result, a high resistant film produced by decomposition of the solvent is less likely to be formed on an electrode to probably improve cell performance.

Table 20 shows that the phosphorus-containing sulfonic acid ester compounds (compounds 44 to 47) represented by the formula (24) have a standard enthalpy of formation (H) of about −156.3 kcal/mol to about −178.9 kcal/mol. That is, the compounds 44 to 47 according to the present invention have excellent storage stability in a non-aqueous electrolyte solution. Further, in cases where such a non-aqueous electrolyte solution is used for electrical storage devices such as secondary batteries, the compounds subjected to electrochemical reduction decomposition enables formation of an SEI on an electrode. As a result, decomposition of solvent molecules in an electrolyte solution can be suppressed.

Further, Table 20 shows that the phosphorus-containing sulfonic acid ester compounds (compounds 44 to 47) represented by the formula (24) have an enthalpy change (ΔH) with hydrolysis reaction of about −2.8 kcal/mol to about −3.8 kcal/mol. That is, the compounds 44 to 47 according to the present invention are also stable to moisture. Further, in cases where such a non-aqueous electrolyte solution is used for electrical storage devices such as secondary batteries, the compounds subjected to electrochemical reduction decomposition enables formation of an SEI on an electrode. As a result, decomposition of solvent molecules in an electrolyte solution can be suppressed.

Thus, the phosphorus-containing sulfonic acid ester compounds represented by the formula (24) according to the additive for a non-aqueous electrolyte solution of the present invention have a sufficiently low LUMO energy, excellent storage stability when contained in a non-aqueous electrolyte solution as an additive for a non-aqueous electrolyte solution, and excellent stability to moisture. This shows that such compounds are effective as a novel additive for a non-aqueous electrolyte solution capable of forming a stable SEI on an electrode of electrical storage devices such as non-aqueous electrolyte solution secondary cells.

(Preparation of Cell)

$LiMn_2O_4$ as a cathode active material and a carbon black as a conductivity imparting agent were dry mixed, and the mixture was uniformly dispersed in N-methyl-2-pyrrolidone (NMP) in which polyvinylidene fluoride (PVDF) was dissolved as a binder to prepare a slurry. The resulting slurry was applied to an aluminum foil (square, thickness of 20 μm) that is to be a cathode current collector, and the NMP was dried off to prepare a cathode sheet. The resulting cathode sheet had a solid mass ratio of cathode active material:conductivity imparting agent:PVDF=80:10:10.

A commercially available graphite-coated electrode sheet (produced by Hohsen Corp.) was used as an anode sheet.

A cylindrical secondary battery was prepared in such a way that an anode sheet and a cathode sheet were laminated and a polyethylene separator was disposed between the sheets in a non-aqueous electrolyte solution prepared in each of the examples and comparative examples.

(Measurement of Discharge Capacity Retention and Internal Resistance Ratio)

The resulting cylindrical secondary batteries each using a non-aqueous electrolyte solution obtained in each of the examples and comparative examples were subjected to a charge/discharge cycle test under the conditions of a temperature of 25° C., a charging rate of 0.3 C, a discharging rate of 0.3 C, a charge termination voltage of 4.2 V, and a discharge termination voltage of 2.5 V. Table 21 shows discharge capacity retention (%) and internal resistance ratio after 200 cycles.

The "discharge capacity retention (%)" after 200 cycles was determined by dividing the discharge capacity (mAh) after 200 cycles of the cycle test by the discharge capacity (mAh) after 10 cycles of the cycle test and multiplying the resulting value by 100. Further, the "internal resistance ratio" after 200 cycles was expressed as a value of the resistance after 200 cycles of the cycle test relative to a value of the resistance before the cycle test taken as 1.

TABLE 21

| | Electrolyte | Solvent | Additive | Discharge capacity retention (%) | Internal resistance ratio |
|---|---|---|---|---|---|
| Example 36 | $LiPF_6$ 1.0 mol/L | EC/DEC (30/70) vol % | Compound 44 0.5% by mass | 91 | 1.34 |
| Example 37 | $LiPF_6$ 1.0 mol/L | EC/DEC (30/70) vol % | Compound 44 1.0% by mass | 96 | 1.21 |
| Example 38 | $LiPF_6$ 1.0 mol/L | EC/DEC (30/70) vol % | Compound 45 1.0% by mass | 98 | 1.18 |
| Example 39 | $LiPF_6$ 1.0 mol/L | EC/DEC (30/70) vol % | Compound 46 1.0% by mass | 96 | 1.20 |
| Example 40 | $LiPF_6$ 1.0 mol/L | EC/DEC (30/70) vol % | Compound 47 1.0% by mass | 95 | 1.25 |
| Comparative Example 24 | $LiPF_6$ 1.0 mol/L | EC/DEC (30/70) vol % | None | 74 | 1.83 |
| Comparative Example 25 | $LiPF_6$ 1.0 mol/L | EC/DEC (30/70) vol % | PS 1.0% by mass | 77 | 1.68 |
| Comparative Example 26 | $LiPF_6$ 1.0 mol/L | EC/DEC (30/70) vol % | VC 1.0% by mass | 83 | 1.69 |
| Comparative Example 27 | $LiPF_6$ 1.0 mol/L | EC/DEC (30/70) vol % | VC 2.0% by mass | 84 | 1.53 |
| Comparative Example 28 | $LiPF_6$ 1.0 mol/L | EC/DEC (30/70) vol % | FEC 1.0% by mass | 81 | 1.66 |
| Comparative Example 29 | $LiPF_6$ 1.0 mol/L | EC/DEC (30/70) vol % | FEC 2.0% by mass | 83 | 1.67 |

Table 21 shows that the cylindrical secondary batteries each using a non-aqueous electrolyte solution containing a phosphorus-containing sulfonic acid ester compound of each of the examples have a higher discharge capacity retention in a cycle test than the cylindrical secondary batteries each using a non-aqueous electrolyte solution of each of the comparative examples. Therefore, in cells such as non-aqueous electrolyte solution secondary cells, the non-aqueous electrolyte solutions each containing an additive for a non-aqueous electrolyte solution formed from a phosphorus-containing sulfonic acid ester compound of each of the examples provide an SEI with higher stability to charge/discharge cycle on the surface of an electrode of the cells than the non-aqueous electrolyte solutions of the comparative examples. Further, the non-aqueous electrolyte solutions each containing a phosphorus-containing sulfonic acid ester compound of each of the examples can keep an internal resistance ratio lower than the non-aqueous electrolyte solutions of the comparative examples, and can suppress an increase in internal resistance during a cycle test.

EXAMPLE 41

Ethylene carbonate (EC) and diethyl carbonate (DEC) were mixed in a volume ratio of EC:DEC=30:70 to prepare a non-aqueous solvent mixture. $LiPF_6$ as an electrolyte was dissolved in the mixture so as to prepare a 1.0 mol/L $LiPF_6$ solution. The compound 48 shown in Table 22 as an additive for a non-aqueous electrolyte solution was added in an amount of 0.5% by mass of the total weight of the solution containing the non-aqueous solvent mixture and the electrolyte. Thus, a non-aqueous electrolyte solution was prepared.

EXAMPLE 42

A non-aqueous electrolyte solution was prepared in the same manner as in Example 41 except that the amount of the compound 48 was 1.0% by mass.

EXAMPLE 43

A non-aqueous electrolyte solution was prepared in the same manner as in Example 42 except that the compound 49 shown in Table 22 was used instead of the compound 48.

EXAMPLE 44

A non-aqueous electrolyte solution was prepared in the same manner as in Example 42 except that the compound 50 shown in Table 22 was used instead of the compound 48.

EXAMPLE 45

A non-aqueous electrolyte solution was prepared in the same manner as in Example 42 except that the compound 51 shown in Table 22 was used instead of the compound 48.

EXAMPLE 46

A non-aqueous electrolyte solution was prepared in the same manner as in Example 42 except that the compound 52 shown in Table 22 was used instead of the compound 48.

EXAMPLE 47

A non-aqueous electrolyte solution was prepared in the same manner as in Example 42 except that the compound 53 shown in Table 22 was used instead of the compound 48.

COMPARATIVE EXAMPLE 30

A non-aqueous electrolyte solution was prepared in the same manner as in Example 41 except that no compound 48 was used.

COMPARATIVE EXAMPLE 31

A non-aqueous electrolyte solution was prepared in the same manner as in Example 42 except that 1,3-propane sultone (PS) was used instead of the compound 48.

COMPARATIVE EXAMPLE 32

A non-aqueous electrolyte solution was prepared in the same manner as in Example 42 except that vinylene carbonate (VC) was used instead of the compound 48.

COMPARATIVE EXAMPLE 33

A non-aqueous electrolyte solution was prepared in the same manner as in Comparative Example 32 except that the amount of the vinylene carbonate (VC) was 2.0% by mass.

COMPARATIVE EXAMPLE 34

A non-aqueous electrolyte solution was prepared in the same manner as in Example 42 except that fluoroethylene carbonate (FEC) was used instead of the compound 48.

COMPARATIVE EXAMPLE 35

A non-aqueous electrolyte solution was prepared in the same manner as in Comparative Example 34 except that the amount of the fluoroethylene carbonate (FEC) was 2.0% by mass.

<Evaluation>
(LUMO Energy, Standard Enthalpy of Formation (H), Enthalpy Change (ΔH) with Hydrolysis Reaction)

The LUMO (lowest unoccupied molecular orbital) energies of the compounds 48 to 53 shown in Table 22 were derived using the Gaussian 03 software. The results are shown in Table 22.

Further, the standard enthalpies of formation (H) of the compounds 48 to 53 were derived using the MOPAC 97 software. The results are shown in Table 22.

Further, the enthalpy changes (ΔH) with hydrolysis reaction of the compounds 48 to 53 were derived using the Gaussian 03 software. The results are shown in Table 22.

TABLE 22

| | Structure | LUMO energy (eV) | H (kcal/mol) | ΔH (kcal/mol) |
|---|---|---|---|---|
| Compound 48 | (cyclic structure with Me, Me on Si) | −2.23 | −207.8 | −4.6 |
| Compound 49 | (cyclic structure with Et, Et on Si) | −1.99 | −199.3 | −4.8 |
| Compound 50 | (cyclic structure with Pr, Pr on Si) | −2.29 | 183.5 | −4.2 |

TABLE 22-continued

| Structure | LUMO energy (eV) | H (kcal/mol) | ΔH (kcal/mol) |
|---|---|---|---|
| Compound 51 (Me, Et substituents on Si) | −2.01 | −178.7 | −4.0 |
| Compound 52 (Me, Ph substituents on Si) | −2.38 | −210.2 | −3.8 |
| Compound 53 (Et, Ph substituents on Si) | −1.89 | −208.3 | −3.7 |

Table 22 shows that the silyl sulfonic acid ester compounds (compounds 48 to 53) represented by the formula (27) have a LUMO energy of about −1.89 eV to about −2.38 eV, and these silyl sulfonic acid ester compounds according to the additive for a non-aqueous electrolyte solution of the present invention have a low LUMO energy. Therefore, in cases where the compounds 48 to 53 are used as an additive for a non-aqueous electrolyte solution for electrical storage devices such as non-aqueous electrolyte solution secondary cells, the compounds 48 to 53 are electrochemically reduced prior to electrochemical reduction of solvents of non-aqueous electrolyte solutions (for example, cyclic carbonate and chain carbonate: LUMO energy of about 1.2 eV), and an SEI is formed on an electrode, whereby decomposition of solvent molecules in an electrolyte solution can be suppressed. As a result, a high resistant film produced by decomposition of the solvent is less likely to be formed on an electrode to probably improve cell performance.

Table 22 shows that the silyl sulfonic acid ester compounds (compounds 48 to 53) represented by the formula (27) have a standard enthalpy of formation (H) of about −178.7 kcal/mol to about −210.2 kcal/mol. That is, the compounds 48 to 53 according to the present invention have excellent storage stability in a non-aqueous electrolyte solution. Further, in cases where such a non-aqueous electrolyte solution is used for electrical storage devices such as secondary batteries, the compounds subjected to electrochemical reduction decomposition enables formation of an SEI on the surface of an electrode. As a result, decomposition of solvent molecules in an electrolyte solution can be suppressed.

Further, Table 22 shows that the silyl sulfonic acid ester compounds (compounds 48 to 53) represented by the formula (27) have an enthalpy change (ΔH) with hydrolysis reaction of about −3.7 kcal/mol to about −4.8 kcal/mol. That is, the compounds 48 to 53 according to the present invention are also stable to moisture. Further, in cases where such a non-aqueous electrolyte solution is used for electrical storage devices such as secondary batteries, the compounds subjected to electrochemical reduction decomposition enables formation of an SEI on an electrode. As a result, decomposition of solvent molecules in an electrolyte solution can be suppressed.

Thus, the silyl sulfonic acid ester compounds represented by the formula (27) according to the additive for a non-aqueous electrolyte solution of the present invention have a sufficiently low LUMO energy, excellent storage stability when contained in a non-aqueous electrolyte solution as an additive for a non-aqueous electrolyte solution, and excellent stability to moisture. This shows that such compounds are effective as a novel additive for a non-aqueous electrolyte solution capable of forming a stable SEI on an electrode of electrical storage devices such as non-aqueous electrolyte solution secondary cells.

(Preparation of Cell)

$LiMn_2O_4$ as a cathode active material and a carbon black as a conductivity imparting agent were dry mixed, and the mixture was uniformly dispersed in N-methyl-2-pyrrolidone (NMP) in which polyvinylidene fluoride (PVDF) was dissolved as a binder to prepare a slurry. The resulting slurry was applied to an aluminum foil (square, thickness of 20 μm) that is to be a cathode current collector, and the NMP was dried off to prepare a cathode sheet. The resulting cathode sheet had a solid mass ratio of cathode active material:conductivity imparting agent:PVDF=80:10:10.

A commercially available graphite-coated electrode sheet (produced by Hohsen Corp.) was used as an anode sheet.

A cylindrical secondary battery was prepared in such a way that an anode sheet and a cathode sheet were laminated and a polyethylene separator was disposed between the sheets in a non-aqueous electrolyte solutions prepared in each of the examples and comparative examples.

(Evaluation of Discharge Capacity Retention and Internal Resistance Ratio)

The resulting cylindrical secondary batteries each using a non-aqueous electrolyte solution obtained in each of the examples and comparative examples were subjected to a charge/discharge cycle test under the conditions of a temperature of 25° C., a charging rate of 0.3 C, a discharging rate of 0.3 C, a charge termination voltage of 4.2 V, and a discharge termination voltage of 2.5 V. Table 23 shows discharge capacity retention (%) and internal resistance after 200 cycles. The "discharge capacity retention (%)" after 200 cycles was determined by dividing the discharge capacity (mAh) after 200 cycles of the cycle test by the discharge capacity (mAh) after 10 cycles of the cycle test and multiplying the resulting value by 100. Further, the "internal resistance ratio" after 200 cycles was expressed as a value of the resistance after 200 cycles of the cycle test relative to a value of the resistance before the cycle test taken as 1.

TABLE 23

| | Electrolyte | Solvent | Additive | Discharge capacity retention (%) | Internal resistance ratio |
|---|---|---|---|---|---|
| Example 41 | LiPF$_6$ 1.0 mol/L | EC/DEC (30/70) vol % | Compound 48 0.5% by mass | 92 | 1.21 |
| Example 42 | LiPF$_6$ 1.0 mol/L | EC/DEC (30/70) vol % | Compound 48 1.0% by mass | 96 | 1.15 |
| Example 43 | LiPF$_6$ 1.0 mol/L | EC/DEC (30/70) vol % | Compound 49 1.0% by mass | 94 | 1.10 |
| Example 44 | LiPF$_6$ 1.0 mol/L | EC/DEC (30/70) vol % | Compound 50 1.0% by mass | 95 | 1.13 |
| Example 45 | LiPF$_6$ 1.0 mol/L | EC/DEC (30/70) vol % | Compound 51 1.0% by mass | 95 | 1.10 |
| Example 46 | LiPF$_6$ 1.0 mol/L | EC/DEC (30/70) vol % | Compound 52 1.0% by mass | 93 | 1.19 |
| Example 47 | LiPF$_6$ 1.0 mol/L | EC/DEC (30/70) vol % | Compound 53 1.0% by mass | 96 | 1.15 |
| Comparative Example 30 | LiPF$_6$ 1.0 mol/L | EC/DEC (30/70) vol % | None | 74 | 1.83 |
| Comparative Example 31 | LiPF$_6$ 1.0 mol/L | EC/DEC (30/70) vol % | PS 1.0% by mass | 77 | 1.68 |
| Comparative Example 32 | LiPF$_6$ 1.0 mol/L | EC/DEC (30/70) vol % | VC 1.0% by mass | 83 | 1.69 |
| Comparative Example 33 | LiPF$_6$ 1.0 mol/L | EC/DEC (30/70) vol % | VC 2.0% by mass | 84 | 1.53 |
| Comparative Example 34 | LiPF$_6$ 1.0 mol/L | EC/DEC (30/70) vol % | FEC 1.0% by mass | 81 | 1.66 |
| Comparative Example 35 | LiPF$_6$ 1.0 mol/L | EC/DEC (30/70) vol % | FEC 2.0% by mass | 83 | 1.67 |

Table 23 shows that the cylindrical secondary batteries each using a non-aqueous electrolyte solution containing a silyl sulfonic acid ester compound of each of the examples have a higher discharge capacity retention in a cycle test than the cylindrical secondary batteries each using a non-aqueous electrolyte solution of each of the comparative examples. Therefore, in cells such as non-aqueous electrolyte solution secondary cells, the non-aqueous electrolyte solutions each containing an additive for a non-aqueous electrolyte solution formed from a silyl sulfonic acid ester compound of each of the examples provide an SEI with higher stability to charge/discharge cycle on the surface of an electrode of the cells than the non-aqueous electrolyte solutions of the comparative examples. Further, the non-aqueous electrolyte solutions each containing a silyl sulfonic acid ester compound of each of the examples have smaller internal resistance, and therefore suppress an increase in internal resistance during a cycle test.

INDUSTRIAL APPLICABILITY

The present invention can provide an additive for a non-aqueous electrolyte solution with excellent storage stability capable of forming a stable SEI on the surface of an electrode to improve cell performance such as a cycle performance, a discharge/charge capacity, and internal resistance, when the additive is used for electrical storage devices such as non-aqueous electrolyte solution secondary cells and electric double layer capacitors.

Further, the present invention can provide a non-aqueous electrolyte solution that contains the additive for a non-aqueous electrolyte solution and an electrical storage device using the non-aqueous electrolyte solution.

REFERENCE SIGNS LIST

1 Non-aqueous electrolyte solution secondary cell
2 Cathode current collector
3 Cathode active material layer
4 Cathode plate
5 Anode current collector
6 Anode active material layer
7 Anode plate
8 Non-aqueous electrolyte solution
9 Separator

The invention claimed is:
1. A non-aqueous electrolyte solution, comprising:
a non-aqueous solvent;
an electrolyte; and
an additive comprising a compound:
having a lowest unoccupied molecular orbital energy of −3.0 to 0.4 eV, a standard enthalpy of formation of −220 to −40 kcal/mol, and an enthalpy change with hydrolysis reaction of −5 to 5 kcal/mo, and represented by the formula:

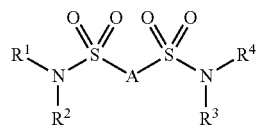

wherein A represents $C_mH_{(2m-n)}Z_n$, m being an integer of 1 to 6, n being an integer of 0 to 12, and Z representing a substituted or unsubstituted alkyl group, a silyl group, a phosphonic acid ester group, an acyl group, a cyano group, or a nitro group; and
$R^1$ is selected from a substituted or unsubstituted C1-C6 alkyl group, a substituted or unsubstituted phenyl group, or —$R^5X^1$ in which $R^5$ represents a substituted or unsubstituted C1-C6 alkylene group and $X^1$ represents a substituted or unsubstituted phenyl group or a substituted or unsubstituted phenoxy group, and $R^2$, $R^3$, and $R^4$ each independently are selected from a hydrogen atom, a substituted or unsubstituted C1-C6 alkyl group, a substituted or unsubstituted phenyl group, or —$R^5X^1$ in which $R^5$ represents a substituted or unsubstituted C1-C6 alkylene group and $X^1$ represents a substituted or unsubstituted phenyl group or a substituted or unsubstituted phenoxy group, $R^2$ and $R^3$ may form a ring together and represent a substituted or unsubstituted C1-C6 alkylene group, a substituted or unsubstituted phenylene group, a carbonyl group, a sulfinyl group, or a C2-C6 divalent group containing alkylene or fluoroalkylene units joined by an ether linkage to each other, and $R^1$ and $R^4$, which form no ring, each represent $-R^6X^2$ in which $R^6$ represents a substituted or unsubstituted C0-C6 alkylene group and $X^2$ represents a hydrogen atom, a halogen atom, a substituted or unsubstituted C1-C6 alkyl group, or a substituted or unsubstituted phenyl group, or a combination of $R^1$ and $R^2$ and a combination of $R^3$ and $R^4$ may form a ring together and represent a C1-C6 alkylene group or a C1-C6 alkylene group optionally having an oxygen atom, a nitrogen atom which may have a substituent, or a sulfur atom, in a carbon chain or at an end of a chain.

2. The non-aqueous electrolyte solution according to claim 1,
wherein the compound is a disulfonic acid amide compound represented by the formula (3):

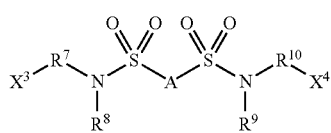

(3)

wherein A represents $C_mH_{(2m-n)}Z_n$, m being an integer of 1 to 6, n being an integer of 0 to 12, Z representing a substituted or unsubstituted C1-C4 alkyl group, a silyl group, an acyl group, a cyano group, or a nitro group; $R^7$ and $R^{10}$ each independently represent a substituted or unsubstituted C0-C6 alkylene group; $X^3$ and $X^4$ each independently represent a substituted or unsubstituted phenyl group; and $R^8$ and $R^9$ each independently represent a hydrogen atom, a substituted or unsubstituted C1-C6 alkyl group, or $-R^{11}X^5$ in which $R^{11}$ represents a substituted or unsubstituted C1-C6 alkylene group and $X^5$ represents a substituted or unsubstituted phenyl group or a substituted or unsubstituted phenoxy group.

3. The non-aqueous electrolyte solution according to claim 1,
wherein the compound is a cyclic disulfonic acid amide compound represented by the formula (9):

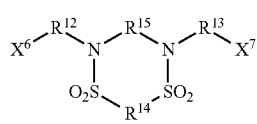

(9)

wherein $R^{12}$ and $R^{13}$ each independently represent a substituted or unsubstituted C0-C6 alkylene group, $R^{14}$ represents a substituted or unsubstituted C1-C5 alkylene group, $R^{15}$ represents a substituted or unsubstituted C1-C5 alkylene group, a substituted or unsubstituted phenylene group, a carbonyl group, a sulfinyl group, or a C2-C6 divalent group containing alkylene or fluoroalkylene units joined by an ether linkage to each other, and $X^6$ and $X^7$ each independently represent a hydrogen atom, a halogen atom, a substituted or unsubstituted C1-C6 alkyl group, or a substituted or unsubstituted phenyl group.

4. The non-aqueous electrolyte solution according to claim 1,
wherein the compound is a phosphorus-containing sulfonic acid amide compound represented by the formula (14):

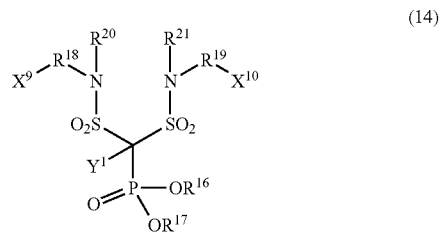

(14)

wherein $R^{16}$ and $R^{17}$ each independently represent a substituted or unsubstituted C1-C6 alkyl group or a substituted or unsubstituted phenyl group, $R^{18}$ and $R^{19}$ each independently represent a substituted or unsubstituted C0-C6 alkylene group, and $X^9$ and $X^{10}$ each independently represent a hydrogen atom, a substituted or unsubstituted C1-C6 alkyl group, or a substituted or unsubstituted phenyl group; and $R^{20}$ and $R^{21}$ each independently represent a hydrogen atom, a substituted or unsubstituted C1-C6 alkyl group, or $-R^{22}X^{11}$ in which $R^{22}$ represents a substituted or unsubstituted C1-C6 alkylene group and $X^{11}$ represents a substituted or unsubstituted phenyl group or a substituted or unsubstituted phenoxy group, or $R^{20}$ and $R^{21}$ may form a ring together and represent a substituted or unsubstituted C1-C6 alkylene group or a substituted or unsubstituted phenylene group, and $Y^1$ represents a hydrogen atom, a substituted or unsubstituted C1-C6 alkyl group, a substituted or unsubstituted phenyl group, or a halogen atom.

5. The non-aqueous electrolyte solution according to claim 1,
wherein the compound is a disulfonic acid amide compound represented by the formula (17):

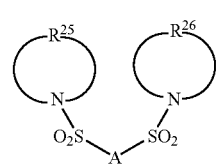

(17)

wherein $R^{25}$ and $R^{26}$ each independently represent a C1-C6 alkylene group or a C1-C6 alkylene group having an oxygen atom, a substituted or unsubstituted nitrogen atom, or a sulfur atom, in a carbon chain or at an end of a chain, A represents $C_mH_{(2m-n)}Z_n$, m being an integer of 1 to 6, n being an integer of 0 to 12, and Z representing a substituted or unsubstituted C1-C4 alkyl group, a silyl group, a phosphonic acid ester group, an acyl group, a cyano group, or a nitro group.

6. The non-aqueous electrolyte solution according to claim 1,
wherein the non-aqueous solvent is an aprotic solvent.

7. The non-aqueous electrolyte solution according to claim 6,
wherein the aprotic solvent is at least one selected from the group consisting of cyclic carbonates, chain carbonates, aliphatic carboxylic acid esters, lactones, lactams, cyclic ethers, chain ethers, sulfones, and halogenated derivatives of these.

8. The non-aqueous electrolyte solution according to claim 1,
wherein the electrolyte includes a lithium salt.

9. The non-aqueous electrolyte solution according to claim 8,
wherein the lithium salt is at least one selected from the group consisting of $LiAlCl_4$, $LiBF_4$, $LiPF_6$, $LiClO_4$, $LiAsF_6$, and $LiSbF_6$.

10. An electrical storage device, comprising:
the non-aqueous electrolyte solution according to claim 1;
a cathode; and
an anode.

11. The electrical storage device according to claim 10, wherein the electrical storage device is a lithium-ion battery.

12. The electrical storage device according to claim 10, wherein the electrical storage device is a lithium ion capacitor.

* * * * *